United States Patent
Friis et al.

(10) Patent No.: US 9,765,318 B2
(45) Date of Patent: *Sep. 19, 2017

(54) GLUCOAMYLASE VARIANTS AND POLYNUCLEOTIDES ENCODING SAME

(71) Applicant: NOVOZYMES A/S, Bagsvaerd (DK)

(72) Inventors: Esben Peter Friis, Herlev (DK); Leonardo De Maria, Frederiksberg (DK); Jesper Vind, Vaerloese (DK); Thomas A. Poulsen, Ballerup (DK); Allan Svendsen, Hoersholm (DK); Steffen Danielsen, Copenhagen Oe (DK); Rolf T. Lenhard, Lyngby (DK); Henrik Friis-Madsen, Ballerup (DK); Lars K. Skov, Ballerup (DK)

(73) Assignee: NOVOZYMES A/S, Bagsvaerd (DK)

( * ) Notice: Subject to any disclaimer, the term of this patent is extended or adjusted under 35 U.S.C. 154(b) by 0 days.

This patent is subject to a terminal disclaimer.

(21) Appl. No.: 15/362,915

(22) Filed: Nov. 29, 2016

(65) Prior Publication Data

US 2017/0073655 A1    Mar. 16, 2017

Related U.S. Application Data

(62) Division of application No. 15/139,050, filed on Apr. 26, 2016, now Pat. No. 9,540,624, which is a division of application No. 14/351,469, filed as application No. PCT/EP2012/070127 on Oct. 11, 2012, now Pat. No. 9,353,362.

(60) Provisional application No. 61/545,628, filed on Oct. 11, 2011.

(51) Int. Cl.
| | |
|---|---|
| *A61K 38/46* | (2006.01) |
| *C12N 9/34* | (2006.01) |
| *C12P 19/20* | (2006.01) |
| *C12P 5/02* | (2006.01) |
| *C12P 7/06* | (2006.01) |
| *C12P 7/54* | (2006.01) |
| *C12P 13/20* | (2006.01) |
| *C12P 37/00* | (2006.01) |
| *C12N 9/30* | (2006.01) |
| *C12P 5/00* | (2006.01) |
| *C12P 7/46* | (2006.01) |
| *C12P 7/48* | (2006.01) |
| *C12P 7/56* | (2006.01) |

(52) U.S. Cl.
CPC ............ *C12N 9/2428* (2013.01); *C12N 9/242* (2013.01); *C12P 5/002* (2013.01); *C12P 5/02* (2013.01); *C12P 7/06* (2013.01); *C12P 7/46* (2013.01); *C12P 7/48* (2013.01); *C12P 7/54* (2013.01); *C12P 7/56* (2013.01); *C12P 13/20* (2013.01); *C12P 19/20* (2013.01); *C12P 37/00* (2013.01); *C12Y 302/01001* (2013.01); *C12Y 302/01003* (2013.01); *Y02E 50/17* (2013.01)

(58) Field of Classification Search
CPC ...................... A61K 38/465; C12Y 301/01034
USPC ......................................................... 435/183
See application file for complete search history.

(56) References Cited

FOREIGN PATENT DOCUMENTS

| WO | 00/04136 A1 | 1/2000 |
|---|---|---|
| WO | 00/34452 A1 | 6/2000 |
| WO | 2011/127802 A1 | 10/2011 |

OTHER PUBLICATIONS

Wu et al, 2003, Guangzhou Food Science and Technology 19(1), 60-62, 84.
Federova et al, 2007—Uniprot Access No. A1DJ85.
Sauer et al, 2000, Biochim et Biophys Acta 1543(2), 275-293.
Yamasaki et al, 1977, Agri Biol Chem 41 (5), 755-762.

*Primary Examiner* — Maryam Monshipouri
(74) *Attorney, Agent, or Firm* — David Fazzolare

(57) ABSTRACT

The present invention relates to glucoamylase variants having improved thermostability. The present invention also relates to polynucleotides encoding the variants; nucleic acid constructs, vectors, and host cells comprising the polynucleotides; and methods of using the variants.

16 Claims, No Drawings

SEQUENCE LISTING

```
<160> NUMBER OF SEQ ID NOS: 10

<210> SEQ ID NO 1
<211> LENGTH: 1851
<212> TYPE: DNA
<213> ORGANISM: Penicillium oxalicum

<400> SEQUENCE: 1
atgcgtctca ctctattatc aggtgtagcc ggcgttctct gcgcaggaca gctgacggcg      60
gcgcgtcctg atcccaaggg tgggaatctg acgccgttca tccacaaaga gggcgagcgg     120
tcgctccaag gcatcttgga caatctcggt gggcgaggta agaaaacacc cggcactgcc     180
gcagggttgt ttattgccag tccaaacaca gagaatccaa actattatta tacatggact     240
cgtgactcag ctttgactgc caagtgcttg atcgacctgt tcgaagactc tcgggcagtc     300
tttccaattg accgcaaata cttggaaaca ggaattcggg actacgtgtc gtcccaagca     360
atcctccaga gtgtgtctaa tccttctgga accctgaagg atggctctgg tctgggtgaa     420
cccaagtttg agattgacct gaatccctt tcgggtgcct ggggtcggcc tcagcgggat     480
ggcccagcgc tgcgagcgac cgctatgatc acctacgcca actacctgat atcccatggt     540
cagaaatcgg atgtgtcaca ggtcatgtgg ccgattattg ccaatgatct agcatatgtt     600
ggtcaatact ggaataatac cggatttgac ctgtgggaag aggtggatgg gtcaagcttt     660
ttcacgattg cggtccagca ccgagcccatt gttgaaggct cgcaactggc gaaaaagctc     720
```

-continued

```
ggcaagtcct gcgatgcctg tgattctcag cctccccaga tattgtgttt cctgcagagt    780
ttctggaacg gaaagtacat cacctccaac atcaacacgc aagcaagccg ctctggtatc    840
gacctggact ctgtcctggg aagcattcat acctttgatc ccgaagcagc ctgtgacgat    900
gcaactttcc agccttgttc tgcccgcgct ctggcgaacc acaaggtcta tgtggattcc    960
ttccgctcta tctacaagat taatgcgggt cttgcagagg gatcggctgc caacgttggc   1020
cgctaccccg aggatgttta ccaaggaggc aatccatggt atctcgccac cctaggcgca   1080
tctgaattgc tttacgacgc cttgtaccag tgggacagac ttggcaaact tgaagtctcg   1140
gagacctcgt tgtcattctt caaagacttt gacgcgaccg tgaaaattgg ctcgtactcg   1200
aggaacagca agacctacaa gaaattgacc cagtccatca agtcgtacgc ggacgggttc   1260
atccagttag tgcagcagta cactccttct aatggatctc tggccgagca atacgatcgc   1320
aatacggctg ctcctctctc tgcaaacgat ctgacttggt catttgcctc tttcttgacg   1380
gctacgcaac gccgcgatgc cgtggttcct ccctcctggg cgcaaagtc ggcaaacaaa    1440
gtcccaacca cttgttcagc ctcccctgtt gtgggtactt ataaggcgcc cacggcaact   1500
ttctcatcca agactaagtg cgtccccgct aaagatattg tgcctatcac gttctacctg   1560
attgagaaca cttactatgg agagaacgtc ttcatgagtg caacattac tgcgctgggt    1620
aactgggacg ccaagaaagg cttcccactc accgcaaacc tctacacgca agatcaaaac   1680
ttgtggttcg ccagtgtcga gttcatccca gcaggcacac cctttgagta caagtactac   1740
aaggtcgagc ccaatggcga tattacttgg gagaagggtc ccaaccgggt gttcgtcgct   1800
cccacgggat gcccagttca gcctcactcc aacgacgtgt ggcagttttg a            1851
```

<210> SEQ ID NO 2
<211> LENGTH: 616
<212> TYPE: PRT
<213> ORGANISM: Penicillium oxalicum

<400> SEQUENCE: 2

```
Met Arg Leu Thr Leu Leu Ser Gly Val Ala Gly Val Leu Cys Ala Gly
 1               5                  10                  15

Gln Leu Thr Ala Ala Arg Pro Asp Pro Lys Gly Asn Leu Thr Pro
             20                  25                  30

Phe Ile His Lys Glu Gly Glu Arg Ser Leu Gln Gly Ile Leu Asp Asn
         35                  40                  45

Leu Gly Arg Gly Lys Lys Thr Pro Gly Thr Ala Ala Gly Leu Phe
     50                  55                  60

Ile Ala Ser Pro Asn Thr Glu Asn Pro Asn Tyr Tyr Tyr Thr Trp Thr
 65                  70                  75                  80

Arg Asp Ser Ala Leu Thr Ala Lys Cys Leu Ile Asp Leu Phe Glu Asp
                 85                  90                  95

Ser Arg Ala Val Phe Pro Ile Asp Arg Lys Tyr Leu Glu Thr Gly Ile
            100                 105                 110

Arg Asp Tyr Val Ser Ser Gln Ala Ile Leu Gln Ser Val Ser Asn Pro
        115                 120                 125

Ser Gly Thr Leu Lys Asp Gly Ser Gly Leu Gly Glu Pro Lys Phe Glu
    130                 135                 140

Ile Asp Leu Asn Pro Phe Ser Gly Ala Trp Gly Arg Pro Gln Arg Asp
145                 150                 155                 160

Gly Pro Ala Leu Arg Ala Thr Ala Met Ile Thr Tyr Ala Asn Tyr Leu
                165                 170                 175
```

```
Ile Ser His Gly Gln Lys Ser Asp Val Ser Gln Val Met Trp Pro Ile
            180                 185                 190
Ile Ala Asn Asp Leu Ala Tyr Val Gly Gln Tyr Trp Asn Asn Thr Gly
        195                 200                 205
Phe Asp Leu Trp Glu Glu Val Asp Gly Ser Ser Phe Phe Thr Ile Ala
    210                 215                 220
Val Gln His Arg Ala Leu Val Glu Gly Ser Gln Leu Ala Lys Lys Leu
225                 230                 235                 240
Gly Lys Ser Cys Asp Ala Cys Asp Ser Gln Pro Gln Ile Leu Cys
                245                 250                 255
Phe Leu Gln Ser Phe Trp Asn Gly Lys Tyr Ile Thr Ser Asn Ile Asn
        260                 265                 270
Thr Gln Ala Ser Arg Ser Gly Ile Asp Leu Asp Ser Val Leu Gly Ser
    275                 280                 285
Ile His Thr Phe Asp Pro Glu Ala Ala Cys Asp Ala Thr Phe Gln
290                 295                 300
Pro Cys Ser Ala Arg Ala Leu Ala Asn His Lys Val Tyr Val Asp Ser
305                 310                 315                 320
Phe Arg Ser Ile Tyr Lys Ile Asn Ala Gly Leu Ala Glu Gly Ser Ala
                325                 330                 335
Ala Asn Val Gly Arg Tyr Pro Glu Asp Val Tyr Gln Gly Gly Asn Pro
            340                 345                 350
Trp Tyr Leu Ala Thr Leu Gly Ala Ser Glu Leu Leu Tyr Asp Ala Leu
        355                 360                 365
Tyr Gln Trp Asp Arg Leu Gly Lys Leu Glu Val Ser Glu Thr Ser Leu
    370                 375                 380
Ser Phe Phe Lys Asp Phe Asp Ala Thr Val Lys Ile Gly Ser Tyr Ser
385                 390                 395                 400
Arg Asn Ser Lys Thr Tyr Lys Lys Leu Thr Gln Ser Ile Lys Ser Tyr
                405                 410                 415
Ala Asp Gly Phe Ile Gln Leu Val Gln Gln Tyr Thr Pro Ser Asn Gly
            420                 425                 430
Ser Leu Ala Glu Gln Tyr Asp Arg Asn Thr Ala Ala Pro Leu Ser Ala
        435                 440                 445
Asn Asp Leu Thr Trp Ser Phe Ala Ser Phe Leu Thr Ala Thr Gln Arg
    450                 455                 460
Arg Asp Ala Val Val Pro Pro Ser Trp Gly Ala Lys Ser Ala Asn Lys
465                 470                 475                 480
Val Pro Thr Thr Cys Ser Ala Ser Pro Val Val Gly Thr Tyr Lys Ala
                485                 490                 495
Pro Thr Ala Thr Phe Ser Ser Lys Thr Lys Cys Val Pro Ala Lys Asp
            500                 505                 510
Ile Val Pro Ile Thr Phe Tyr Leu Ile Glu Asn Thr Tyr Tyr Gly Glu
        515                 520                 525
Asn Val Phe Met Ser Gly Asn Ile Thr Ala Leu Gly Asn Trp Asp Ala
    530                 535                 540
Lys Lys Gly Phe Pro Leu Thr Ala Asn Leu Tyr Thr Gln Asp Gln Asn
545                 550                 555                 560
Leu Trp Phe Ala Ser Val Glu Phe Ile Pro Ala Gly Thr Pro Phe Glu
                565                 570                 575
Tyr Lys Tyr Tyr Lys Val Glu Pro Asn Gly Asp Ile Thr Trp Glu Lys
            580                 585                 590
Gly Pro Asn Arg Val Phe Val Ala Pro Thr Gly Cys Pro Val Gln Pro
```

```
                595                 600                 605
His Ser Asn Asp Val Trp Gln Phe
    610                 615

<210> SEQ ID NO 3
<211> LENGTH: 595
<212> TYPE: PRT
<213> ORGANISM: Penicillium oxalicum

<400> SEQUENCE: 3

Arg Pro Asp Pro Lys Gly Gly Asn Leu Thr Pro Phe Ile His Lys Glu
1               5                   10                  15

Gly Glu Arg Ser Leu Gln Gly Ile Leu Asp Asn Leu Gly Gly Arg Gly
            20                  25                  30

Lys Lys Thr Pro Gly Thr Ala Ala Gly Leu Phe Ile Ala Ser Pro Asn
        35                  40                  45

Thr Glu Asn Pro Asn Tyr Tyr Tyr Thr Trp Thr Arg Asp Ser Ala Leu
    50                  55                  60

Thr Ala Lys Cys Leu Ile Asp Leu Phe Glu Asp Ser Arg Ala Val Phe
65                  70                  75                  80

Pro Ile Asp Arg Lys Tyr Leu Glu Thr Gly Ile Arg Asp Tyr Val Ser
                85                  90                  95

Ser Gln Ala Ile Leu Gln Ser Val Ser Asn Pro Ser Gly Thr Leu Lys
            100                 105                 110

Asp Gly Ser Gly Leu Gly Glu Pro Lys Phe Glu Ile Asp Leu Asn Pro
        115                 120                 125

Phe Ser Gly Ala Trp Gly Arg Pro Gln Arg Asp Gly Pro Ala Leu Arg
    130                 135                 140

Ala Thr Ala Met Ile Thr Tyr Ala Asn Tyr Leu Ile Ser His Gly Gln
145                 150                 155                 160

Lys Ser Asp Val Ser Gln Val Met Trp Pro Ile Ile Ala Asn Asp Leu
                165                 170                 175

Ala Tyr Val Gly Gln Tyr Trp Asn Asn Thr Gly Phe Asp Leu Trp Glu
            180                 185                 190

Glu Val Asp Gly Ser Ser Phe Phe Thr Ile Ala Val Gln His Arg Ala
        195                 200                 205

Leu Val Glu Gly Ser Gln Leu Ala Lys Lys Leu Gly Lys Ser Cys Asp
    210                 215                 220

Ala Cys Asp Ser Gln Pro Pro Gln Ile Leu Cys Phe Leu Gln Ser Phe
225                 230                 235                 240

Trp Asn Gly Lys Tyr Ile Thr Ser Asn Ile Asn Thr Gln Ala Ser Arg
                245                 250                 255

Ser Gly Ile Asp Leu Asp Ser Val Leu Gly Ser Ile His Thr Phe Asp
            260                 265                 270

Pro Glu Ala Ala Cys Asp Asp Ala Thr Phe Gln Pro Cys Ser Ala Arg
        275                 280                 285

Ala Leu Ala Asn His Lys Val Tyr Val Asp Ser Phe Arg Ser Ile Tyr
    290                 295                 300

Lys Ile Asn Ala Gly Leu Ala Glu Gly Ser Ala Ala Asn Val Gly Arg
305                 310                 315                 320

Tyr Pro Glu Asp Val Tyr Gln Gly Gly Asn Pro Trp Tyr Leu Ala Thr
                325                 330                 335

Leu Gly Ala Ser Glu Leu Leu Tyr Asp Ala Leu Tyr Gln Trp Asp Arg
            340                 345                 350
```

```
Leu Gly Lys Leu Glu Val Ser Glu Thr Ser Leu Ser Phe Lys Asp
            355                 360                 365
Phe Asp Ala Thr Val Lys Ile Gly Ser Tyr Ser Arg Asn Ser Lys Thr
    370                 375                 380
Tyr Lys Lys Leu Thr Gln Ser Ile Lys Ser Tyr Ala Asp Gly Phe Ile
385                 390                 395                 400
Gln Leu Val Gln Gln Tyr Thr Pro Ser Asn Gly Ser Leu Ala Glu Gln
                405                 410                 415
Tyr Asp Arg Asn Thr Ala Ala Pro Leu Ser Ala Asn Asp Leu Thr Trp
            420                 425                 430
Ser Phe Ala Ser Phe Leu Thr Ala Thr Gln Arg Arg Asp Ala Val Val
        435                 440                 445
Pro Pro Ser Trp Gly Ala Lys Ser Ala Asn Lys Val Pro Thr Thr Cys
    450                 455                 460
Ser Ala Ser Pro Val Val Gly Thr Tyr Lys Ala Pro Thr Ala Thr Phe
465                 470                 475                 480
Ser Ser Lys Thr Lys Cys Val Pro Ala Lys Asp Ile Val Pro Ile Thr
                485                 490                 495
Phe Tyr Leu Ile Glu Asn Thr Tyr Tyr Gly Glu Asn Val Phe Met Ser
            500                 505                 510
Gly Asn Ile Thr Ala Leu Gly Asn Trp Asp Ala Lys Lys Gly Phe Pro
        515                 520                 525
Leu Thr Ala Asn Leu Tyr Thr Gln Asp Gln Asn Leu Trp Phe Ala Ser
    530                 535                 540
Val Glu Phe Ile Pro Ala Gly Thr Pro Phe Glu Tyr Lys Tyr Tyr Lys
545                 550                 555                 560
Val Glu Pro Asn Gly Asp Ile Thr Trp Glu Lys Gly Pro Asn Arg Val
                565                 570                 575
Phe Val Ala Pro Thr Gly Cys Pro Val Gln Pro His Ser Asn Asp Val
            580                 585                 590
Trp Gln Phe
    595

<210> SEQ ID NO 4
<211> LENGTH: 25
<212> TYPE: DNA
<213> ORGANISM: Artificial
<220> FEATURE:
<223> OTHER INFORMATION: PCR primer

<400> SEQUENCE: 4
atgcgtctca ctctattatc aggtg                                          25

<210> SEQ ID NO 5
<211> LENGTH: 39
<212> TYPE: DNA
<213> ORGANISM: Artificial
<220> FEATURE:
<223> OTHER INFORMATION: PCR primer

<400> SEQUENCE: 5
acacaactgg ggatccacca tgcgtctcac tctattatc                           39

<210> SEQ ID NO 6
<211> LENGTH: 37
<212> TYPE: DNA
<213> ORGANISM: Artificial
<220> FEATURE:
<223> OTHER INFORMATION: PCR primer
```

```
<400> SEQUENCE: 6
agatctcgag aagcttaaaa ctgccacacg tcgttgg                              37

<210> SEQ ID NO 7
<211> LENGTH: 18
<212> TYPE: DNA
<213> ORGANISM: Artificial
<220> FEATURE:
<223> OTHER INFORMATION: PCR primer

<400> SEQUENCE: 7
gcagtctttc caattgac                                                  18

<210> SEQ ID NO 8
<211> LENGTH: 18
<212> TYPE: DNA
<213> ORGANISM: Artificial
<220> FEATURE:
<223> OTHER INFORMATION: PCR primer

<400> SEQUENCE: 8
aattggaaag actgcccg                                                  18

<210> SEQ ID NO 9
<211> LENGTH: 39
<212> TYPE: DNA
<213> ORGANISM: Artificial
<220> FEATURE:
<223> OTHER INFORMATION: PCR primer

<400> SEQUENCE: 9
acacaactgg ggatccacca tgcgtctcac tctattatc                            39

<210> SEQ ID NO 10
<211> LENGTH: 37
<212> TYPE: DNA
<213> ORGANISM: Artificial
<220> FEATURE:
<223> OTHER INFORMATION: PCR primer

<400> SEQUENCE: 10
agatctcgag aagcttaaaa ctgccacacg tcgttgg                              37
```

GLUCOAMYLASE VARIANTS AND POLYNUCLEOTIDES ENCODING SAME

CROSS-REFERENCE TO RELATED APPLICATIONS

This application is a division of U.S. application Ser. No. 15/139,050 filed Apr. 26, 2016, now U.S. Pat. No. 9,540,624, which is a division of U.S. application Ser. No. 14/351,469 filed Apr. 11, 2014, now U.S. Pat. No. 9,353,362, which is a 35 U.S.C. 371 national application of PCT/EP2012/070127 filed Oct. 11, 2012, which claims priority or the benefit under 35 U.S.C. 119 of U.S. provisional application No. 61/545,628 filed Oct. 11, 2011, the contents of which are fully incorporated herein by reference.

REFERENCE TO A SEQUENCE LISTING

This application contains a Sequence Listing in computer readable form, which is incorporated herein by reference.

BACKGROUND OF THE INVENTION

Field of the Invention

The present invention relates to glucoamylase variants, polynucleotides encoding the variants, methods of producing the variants, and methods of using the variants.

Description of the Related Art

Glucoamylase (1,4-alpha-D-glucan glucohydrolase, EC 3.2.1.3) is an enzyme, which catalyzes the release of D-glucose from the non-reducing ends of starch or related oligo- and polysaccharide molecules. Glucoamylases are produced by several filamentous fungi and yeast, with those from *Aspergillus* being commercially most important.

Commercially, glucoamylases are used to convert starchy material, which is already partially hydrolyzed by an alpha-amylase, to glucose. The glucose may then be converted directly or indirectly into a fermentation product using a fermenting organism. Examples of commercial fermentation products include alcohols (e.g., ethanol, methanol, butanol, 1,3-propanediol); organic acids (e.g., citric acid, acetic acid, itaconic acid, lactic acid, gluconic acid, gluconate, lactic acid, succinic acid, 2,5-diketo-D-gluconic acid); ketones (e.g., acetone); amino acids (e.g., glutamic acid); gases (e.g., $H_2$ and $CO_2$), and more complex compounds, including, for example, antibiotics (e.g., penicillin and tetracycline); enzymes; vitamins (e.g., riboflavin, $B_{12}$, beta-carotene); hormones, and other compounds which are difficult to produce synthetically. Fermentation processes are also commonly used in the consumable alcohol (e.g., beer and wine), dairy (e.g., in the production of yogurt and cheese) industries.

The end product may also be syrup. For instance, the end product may be glucose, but may also be converted, e.g., by glucose isomerase to fructose or a mixture composed almost equally of glucose and fructose. This mixture, or a mixture further enriched with fructose, is the most commonly used high fructose corn syrup (HFCS) commercialized throughout the world.

It is an object of the present invention to provide polypeptides having glucoamylase activity and polynucleotides encoding the polypeptides and which provide a high yield in fermentation product production processes, such as ethanol production processes, including one-step ethanol fermentation processes from un-gelatinized raw (or uncooked) starch. Copending patent application, WO2011/127802, discloses a wild type glucoamylase from *Penicillium oxalicum*.

The present invention provides a glucoamylase variant with improved properties compared to its parent.

SUMMARY OF THE INVENTION

In a first aspect the present invention relates to glucoamylase variants, comprising a substitution or deletion at one or more positions corresponding to positions 1, 2, 3, 4, 5, 6, 7, 8, 10, 11, 12, 18, 26, 31, 33, 34, 65, 72, 74, 79, 80, 103, 105, 112, 161, 172, 218, 220, 221, 245, 253, 255, 279, 325, 327, 359, 364, 370, 375, 377, 405, 445, 447, 460, 463, 465, 468, 477, 501, 502, 504, 516, 524, 526, 563, 564, 568, 571 of the polypeptide of SEQ ID NO: 3, wherein the variant has glucoamylase activity.

In a second aspect the present invention relates to a variant glucoamylase catalytic domain comprising a substitution at one or more positions corresponding to positions 10, 11, 12, 18, 26, 31, 33, 34, 65, 72, 74, 79, 80, 103, 105, 112, 161, 172, 218, 220, 221, 245, 253, 255, 279, 325, 327, 359, 364, 370, 375, 377, 405, 445, 447, 460, 463, 465, 468 of the polypeptide of SEQ ID NO: 3, wherein the variant catalytic domain has glucoamylase activity.

In a third aspect the present invention relates to a composition comprising the variant polypeptide of the invention.

In further aspects the present invention also relates to isolated polynucleotides encoding the variants; nucleic acid constructs, vectors, and host cells comprising the polynucleotides; and methods of producing the variants.

The present invention also relates to methods of using the polypeptides of the invention in production of syrup and/or a fermentation product.

Definitions

Glucoamylase: The term glucoamylase (1,4-alpha-D-glucan glucohydrolase, EC 3.2.1.3) is defined as an enzyme, which catalyzes the release of D-glucose from the non-reducing ends of starch or related oligo- and polysaccharide molecules. For purposes of the present invention, glucoamylase activity is determined according to the procedure described in the 'Materials & Methods'-section herein.

The polypeptides of the present invention have at least 20%, preferably at least 40%, preferably at least 45%, more preferably at least 50%, more preferably at least 55%, more preferably at least 60%, more preferably at least 65%, more preferably at least 70%, more preferably at least 75%, more preferably at least 80%, more preferably at least 85%, even more preferably at least 90%, most preferably at least 95%, and even most preferably at least 100% of the glucoamylase activity of the mature polypeptide of SEQ ID NO: 2. In another embodiment the polypeptides of the present invention have at least 20%, preferably at least 40%, preferably at least 45%, more preferably at least 50%, more preferably at least 55%, more preferably at least 60%, more preferably at least 65%, more preferably at least 70%, more preferably at least 75%, more preferably at least 80%, more preferably at least 85%, even more preferably at least 90%, most preferably at least 95%, and even most preferably at least 100% of the glucoamylase activity of the polypeptide of SEQ ID NO: 3.

Allelic variant: The term "allelic variant" means any of two or more alternative forms of a gene occupying the same chromosomal locus. Allelic variation arises naturally through mutation, and may result in polymorphism within populations. Gene mutations can be silent (no change in the encoded polypeptide) or may encode polypeptides having altered amino acid sequences. An allelic variant of a polypeptide is a polypeptide encoded by an allelic variant of a gene.

cDNA: The term "cDNA" means a DNA molecule that can be prepared by reverse transcription from a mature, spliced, mRNA molecule obtained from a eukaryotic or prokaryotic cell. cDNA lacks intron sequences that may be present in the corresponding genomic DNA. The initial, primary RNA transcript is a precursor to mRNA that is processed through a series of steps, including splicing, before appearing as mature spliced mRNA.

Coding sequence: The term "coding sequence" means a polynucleotide, which directly specifies the amino acid sequence of a variant. The boundaries of the coding sequence are generally determined by an open reading frame, which begins with a start codon such as ATG, GTG or TTG and ends with a stop codon such as TAA, TAG, or TGA. The coding sequence may be a genomic DNA, cDNA, synthetic DNA, or a combination thereof.

Control sequences: The term "control sequences" means nucleic acid sequences necessary for expression of a polynucleotide encoding a variant of the present invention. Each control sequence may be native (i.e., from the same gene) or foreign (i.e., from a different gene) to the polynucleotide encoding the variant or native or foreign to each other. Such control sequences include, but are not limited to, a leader, polyadenylation sequence, propeptide sequence, promoter, signal peptide sequence, and transcription terminator. At a minimum, the control sequences include a promoter, and transcriptional and translational stop signals. The control sequences may be provided with linkers for the purpose of introducing specific restriction sites facilitating ligation of the control sequences with the coding region of the polynucleotide encoding a variant.

Expression: The term "expression" includes any step involved in the production of a variant including, but not limited to, transcription, post-transcriptional modification, translation, post-translational modification, and secretion.

Expression vector: The term "expression vector" means a linear or circular DNA molecule that comprises a polynucleotide encoding a variant and is operably linked to control sequences that provide for its expression.

Fragment: The term "fragment" means a polypeptide having one or more (e.g., several) amino acids absent from the amino and/or carboxyl terminus of a mature polypeptide; wherein the fragment has glucoamylase activity. In one aspect, a fragment contains at least 465 amino acid residues (e.g., amino acids 30 to 494 of SEQ ID NO: 2).

High stringency conditions: The term "high stringency conditions" means for probes of at least 100 nucleotides in length, prehybridization and hybridization at 42° C. in 5×SSPE, 0.3% SDS, 200 micrograms/ml sheared and denatured salmon sperm DNA, and 50% formamide, following standard Southern blotting procedures for 12 to 24 hours. The carrier material is finally washed three times each for 15 minutes using 2×SSC, 0.2% SDS at 65° C.

Host cell: The term "host cell" means any cell type that is susceptible to transformation, transfection, transduction, or the like with a nucleic acid construct or expression vector comprising a polynucleotide of the present invention. The term "host cell" encompasses any progeny of a parent cell that is not identical to the parent cell due to mutations that occur during replication.

Improved property: The term "improved property" means a characteristic associated with a variant that is improved compared to the parent. Such improved properties include, but are not limited to, improved thermo-stability.

Isolated: The term "isolated" means a substance in a form or environment which does not occur in nature. Non-limiting examples of isolated substances include (1) any non-naturally occurring substance, (2) any substance including, but not limited to, any enzyme, variant, nucleic acid, protein, peptide or cofactor, that is at least partially removed from one or more or all of the naturally occurring constituents with which it is associated in nature; (3) any substance modified by the hand of man relative to that substance found in nature; or (4) any substance modified by increasing the amount of the substance relative to other components with which it is naturally associated (e.g., multiple copies of a gene encoding the substance; use of a stronger promoter than the promoter naturally associated with the gene encoding the substance). An isolated substance may be present in a fermentation broth sample.

Low stringency conditions: The term "low stringency conditions" means for probes of at least 100 nucleotides in length, prehybridization and hybridization at 42° C. in 5×SSPE, 0.3% SDS, 200 micrograms/ml sheared and denatured salmon sperm DNA, and 25% formamide, following standard Southern blotting procedures for 12 to 24 hours. The carrier material is finally washed three times each for 15 minutes using 2×SSC, 0.2% SDS at 50° C.

Mature polypeptide: The term "mature polypeptide" means a polypeptide in its final form following translation and any post-translational modifications, such as N-terminal processing, C-terminal truncation, glycosylation, phosphorylation, etc. In one aspect, the mature polypeptide is amino acids 22 to 616 of SEQ ID NO: 2 based on the program SignalP (Nielsen et al., 1997, *Protein Engineering* 10: 1-6) that predicts amino acids 1 to 21 of SEQ ID NO: 2 are a signal peptide. It is known in the art that a host cell may produce a mixture of two of more different mature polypeptides (i.e., with a different C-terminal and/or N-terminal amino acid) expressed by the same polynucleotide.

Mature polypeptide coding sequence: The term "mature polypeptide coding sequence" means a polynucleotide that encodes a mature polypeptide having glucoamylase activity. In one aspect, the mature polypeptide coding sequence is nucleotides 64 to 1848 of SEQ ID NO: 1 based on the SignalP (Nielsen et al., 1997, supra) that predicts nucleotides 1 to 63 of SEQ ID NO: 1 encode a signal peptide.

Medium stringency conditions: The term "medium stringency conditions" means for probes of at least 100 nucleotides in length, prehybridization and hybridization at 42° C. in 5×SSPE, 0.3% SDS, 200 micrograms/ml sheared and denatured salmon sperm DNA, and 35% formamide, following standard Southern blotting procedures for 12 to 24 hours. The carrier material is finally washed three times each for 15 minutes using 2×SSC, 0.2% SDS at 55° C.

Medium-high stringency conditions: The term "medium-high stringency conditions" means for probes of at least 100 nucleotides in length, prehybridization and hybridization at 42° C. in 5×SSPE, 0.3% SDS, 200 micrograms/ml sheared and denatured salmon sperm DNA, and either 35% formamide, following standard Southern blotting procedures for 12 to 24 hours. The carrier material is finally washed three times each for 15 minutes using 2×SSC, 0.2% SDS at 60° C.

Mutant: The term "mutant" means a polynucleotide encoding a variant.

Nucleic acid construct: The term "nucleic acid construct" means a nucleic acid molecule, either single- or double-stranded, which is isolated from a naturally occurring gene or is modified to contain segments of nucleic acids in a manner that would not otherwise exist in nature or which is synthetic, which comprises one or more control sequences.

Operably linked: The term "operably linked" means a configuration in which a control sequence is placed at an appropriate position relative to the coding sequence of a polynucleotide such that the control sequence directs expression of the coding sequence.

Parent or parent glucoamylase: The term "parent" or "parent glucoamylase" means a glucoamylase to which an alteration is made to produce the enzyme variants of the present invention. The parent may be a naturally occurring (wild-type) polypeptide or a variant or fragment thereof.

Sequence identity: The relatedness between two amino acid sequences or between two nucleotide sequences is described by the parameter "sequence identity".

For purposes of the present invention, the sequence identity between two amino acid sequences is determined using the Needleman-Wunsch algorithm (Needleman and Wunsch, 1970, *J. Mol. Biol.* 48: 443-453) as implemented in the Needle program of the EMBOSS package (EMBOSS: The European Molecular Biology Open Software Suite, Rice et al., 2000, *Trends Genet.* 16: 276-277), preferably version 5.0.0 or later. The parameters used are gap open penalty of 10, gap extension penalty of 0.5, and the EBLOSUM62 (EMBOSS version of BLOSUM62) substitution matrix. The output of Needle labeled "longest identity" (obtained using the -nobrief option) is used as the percent identity and is calculated as follows:

(Identical Residues×100)/(Length of Alignment−
Total Number of Gaps in Alignment)

For purposes of the present invention, the sequence identity between two deoxyribonucleotide sequences is determined using the Needleman-Wunsch algorithm (Needleman and Wunsch, 1970, supra) as implemented in the Needle program of the EMBOSS package (EMBOSS: The European Molecular Biology Open Software Suite, Rice et al., 2000, supra), preferably version 5.0.0 or later. The parameters used are gap open penalty of 10, gap extension penalty of 0.5, and the EDNAFULL (EMBOSS version of NCBI NUC4.4) substitution matrix. The output of Needle labeled "longest identity" (obtained using the -nobrief option) is used as the percent identity and is calculated as follows:

(Identical Deoxyribonucleotides×100)/(Length of
Alignment−Total Number of Gaps in Alignment)

Subsequence: The term "subsequence" means a polynucleotide having one or more (e.g., several) nucleotides absent from the 5' and/or 3' end of a mature polypeptide coding sequence; wherein the subsequence encodes a fragment having glucoamylase activity. In one aspect, a subsequence contains at least 1395 nucleotides (e.g., nucleotides 88 to 1482 of SEQ ID NO: 1)

Variant: The term "variant" means a polypeptide having glucoamylase activity comprising an alteration, i.e., a substitution, insertion, and/or deletion, at one or more (e.g., several) positions. A substitution means replacement of the amino acid occupying a position with a different amino acid; a deletion means removal of the amino acid occupying a position; and an insertion means adding an amino acid adjacent to and immediately following the amino acid occupying a position. The variants of the present invention have at least 20%, e.g., at least 40%, at least 50%, at least 60%, at least 70%, at least 80%, at least 90%, at least 95%, or at least 100% of the glucoamylase activity of the mature polypeptide of SEQ ID NO: 2. The variants of the present invention have at least 20%, e.g., at least 40%, at least 50%, at least 60%, at least 70%, at least 80%, at least 90%, at least 95%, or at least 100% of the glucoamylase activity of the polypeptide of SEQ ID NO: 3.

Very high stringency conditions: The term "very high stringency conditions" means for probes of at least 100 nucleotides in length, prehybridization and hybridization at 42° C. in 5×SSPE, 0.3% SDS, 200 micrograms/ml sheared and denatured salmon sperm DNA, and 50% formamide, following standard Southern blotting procedures for 12 to 24 hours. The carrier material is finally washed three times each for 15 minutes using 2×SSC, 0.2% SDS at 70° C.

Very low stringency conditions: The term "very low stringency conditions" means for probes of at least 100 nucleotides in length, prehybridization and hybridization at 42° C. in 5×SSPE, 0.3% SDS, 200 micrograms/ml sheared and denatured salmon sperm DNA, and 25% formamide, following standard Southern blotting procedures for 12 to 24 hours. The carrier material is finally washed three times each for 15 minutes using 2×SSC, 0.2% SDS at 45° C.

Wild-type glucoamylase: The term "wild-type" glucoamylase means a glucoamylase expressed by a naturally occurring microorganism, such as a bacterium, yeast, or filamentous fungus found in nature.

Conventions for Designation of Variants

For purposes of the present invention, the mature polypeptide comprised in SEQ ID NO: 2 or the polypeptide consisting of SEQ ID NO: 3 (PE001) is used to determine the corresponding amino acid residue in another glucoamylase. The amino acid sequence of another glucoamylase is aligned with the mature polypeptide disclosed as amino acids 22 to 616 of SEQ ID NO: 2 or amino acids 1-595 Of SEQ ID NO: 3, and based on the alignment, the amino acid position number corresponding to any amino acid residue in the mature polypeptide disclosed in SEQ ID NO: 2 or the polypeptide of SEQ ID NO: 3 is determined using the Needleman-Wunsch algorithm (Needleman and Wunsch, 1970, *J. Mol. Biol.* 48: 443-453) as implemented in the Needle program of the EMBOSS package (EMBOSS: The European Molecular Biology Open Software Suite, Rice et al., 2000, *Trends Genet.* 16: 276-277), preferably version 5.0.0 or later. The parameters used are gap open penalty of 10, gap extension penalty of 0.5, and the EBLOSUM62 (EMBOSS version of BLOSUM62) substitution matrix.

Identification of the corresponding amino acid residue in another glucoamylase can be determined by an alignment of multiple polypeptide sequences using several computer programs including, but not limited to, MUSCLE (multiple sequence comparison by log-expectation; version 3.5 or later; Edgar, 2004, *Nucleic Acids Research* 32: 1792-1797), MAFFT (version 6.857 or later; Katoh and Kuma, 2002, *Nucleic Acids Research* 30: 3059-3066; Katoh et al., 2005, *Nucleic Acids Research* 33: 511-518; Katoh and Toh, 2007, *Bioinformatics* 23: 372-374; Katoh et al., 2009, *Methods in Molecular Biology* 537: 39-64; Katoh and Toh, 2010, *Bioinformatics* 26: 1899-1900), and EMBOSS EMMA employing ClustalW (1.83 or later; Thompson et al., 1994, *Nucleic Acids Research* 22: 4673-4680), using their respective default parameters.

When the other enzyme has diverged from the mature polypeptide of SEQ ID NO: 2 such that traditional sequence-based comparison fails to detect their relationship (Lindahl and Elofsson, 2000, *J. Mol. Biol.* 295: 613-615), other pairwise sequence comparison algorithms can be used. Greater sensitivity in sequence-based searching can be attained using search programs that utilize probabilistic representations of polypeptide families (profiles) to search databases. For example, the PSI-BLAST program generates profiles through an iterative database search process and is capable of detecting remote homologs (Atschul et al., 1997, *Nucleic Acids Res.* 25: 3389-3402). Even greater sensitivity can be achieved if the family or superfamily for the polypeptide has one or more representatives in the protein structure databases. Programs such as GenTHREADER (Jones, 1999, *J. Mol. Biol.* 287: 797-815; McGuffin and Jones, 2003, *Bioinformatics* 19: 874-881) utilize information from a variety of sources (PSI-BLAST, secondary structure prediction, structural alignment profiles, and solvation potentials) as input to a neural network that predicts the structural fold for a query sequence. Similarly, the method of Gough et al., 2000, *J. Mol. Biol.* 313: 903-919, can be used to align a sequence of unknown structure with the superfamily models present in the SCOP database. These alignments can in turn be used to generate homology models for the polypeptide, and such models can be assessed for accuracy using a variety of tools developed for that purpose.

For proteins of known structure, several tools and resources are available for retrieving and generating structural alignments. For example the SCOP superfamilies of proteins have been structurally aligned, and those alignments are accessible and downloadable. Two or more protein structures can be aligned using a variety of algorithms such as the distance alignment matrix (Holm and Sander, 1998, *Proteins* 33: 88-96) or combinatorial extension (Shindyalov and Bourne, 1998, *Protein Engineering* 11: 739-747), and implementation of these algorithms can additionally be utilized to query structure databases with a structure of interest in order to discover possible structural homologs (e.g., Holm and Park, 2000, *Bioinformatics* 16: 566-567).

In describing the variants of the present invention, the nomenclature described below is adapted for ease of reference. The accepted IUPAC single letter or three letter amino acid abbreviation is employed.

Substitutions.

For an amino acid substitution, the following nomenclature is used: Original amino acid, position, substituted amino acid. Accordingly, the substitution of threonine at position 226 with alanine is designated as "Thr226Ala" or "T226A". Multiple mutations are separated by addition marks ("+"), e.g., "Gly205Arg+Ser411Phe" or "G205R+S411F", representing substitutions at positions 205 and 411 of glycine (G) with arginine (R) and serine (S) with phenylalanine (F), respectively.

Deletions.

For an amino acid deletion, the following nomenclature is used: Original amino acid, position, *. Accordingly, the deletion of glycine at position 195 is designated as "Gly195*" or "G195*". Multiple deletions are separated by addition marks ("+"), e.g., "Gly195*+Ser411*" or "G195*+S411*".

Insertions.

For an amino acid insertion, the following nomenclature is used: Original amino acid, position, original amino acid, inserted amino acid. Accordingly the insertion of lysine after glycine at position 195 is designated "Gly195GlyLys" or "G195GK". An insertion of multiple amino acids is designated [Original amino acid, position, original amino acid, inserted amino acid #1, inserted amino acid #2; etc.]. For example, the insertion of lysine and alanine after glycine at position 195 is indicated as "Gly195GlyLysAla" or "G195GKA".

In such cases the inserted amino acid residue(s) are numbered by the addition of lower case letters to the position number of the amino acid residue preceding the inserted amino acid residue(s). In the above example, the sequence would thus be:

| Parent: | Variant: |
|---------|----------|
| 195     | 195 195a 195b |
| G       | G - K - A |

Multiple Alterations.

Variants comprising multiple alterations are separated by addition marks ("+"), e.g., "Arg170Tyr+Gly195Glu" or "R170Y+G195E" representing a substitution of arginine and glycine at positions 170 and 195 with tyrosine and glutamic acid, respectively.

Different Alterations.

Where different alterations can be introduced at a position, the different alterations are separated by a comma, e.g., "Arg170Tyr, Glu" represents a substitution of arginine at position 170 with tyrosine or glutamic acid. Thus, "Tyr167Gly, Ala+Arg170Gly, Ala" designates the following variants:
"Tyr167Gly+Arg170Gly", "Tyr167Gly+Arg170Ala", "Tyr167Ala+Arg170Gly", and "Tyr167Ala+Arg170Ala".

DETAILED DESCRIPTION OF THE INVENTION

The present invention relates to isolated glucoamylase variants, comprising a substitution at one or more positions corresponding to positions 1, 2, 3, 4, 5, 6, 7, 8, 10, 11, 12, 18, 26, 31, 33, 34, 65, 72, 74, 79, 103, 105, 112, 161, 172, 218, 220, 221, 245, 253, 255, 279, 325, 327, 359, 364, 370, 375, 377, 405, 445, 447, 460, 463, 465, 468, 477, 501, 502, 504, 516, 524, 526, 563, 564, 568, 571 of the polypeptide of SEQ ID NO: 3, wherein the variant has glucoamylase activity.

The present invention also relates to isolated glucoamylase variants, comprising a deletion at one or more positions corresponding to positions 80, 502, or 504 of the polypeptide of SEQ ID NO: 3, wherein the variant has glucoamylase activity.

The above mentioned variants having substitutions or deletions should be understood as encompassing all possible combinations of one or more substitutions or deletions at the specified positions.

Variants

The present invention provides glucoamylase variants, comprising a substitution or deletion at one or more positions corresponding to positions 1, 2, 3, 4, 5, 6, 7, 8, 10, 11, 12, 18, 26, 31, 33, 34, 65, 72, 74, 79, 80, 103, 105, 112, 161, 172, 218, 220, 221, 245, 253, 255, 279, 325, 327, 359, 364, 370, 375, 377, 405, 445, 447, 460, 463, 465, 468, 477, 501, 502, 504, 516, 524, 526, 563, 564, 568, 571 of the polypeptide of SEQ ID NO: 3, wherein the variant has glucoamylase activity.

In addition to the specific substitutions or deletions in a further embodiment the variant is selected from the group consisting of:

a) a polypeptide having at least 65% sequence identity to the polypeptide of SEQ ID NO: 3;

b) a polypeptide encoded by a polynucleotide that hybridizes under low stringency conditions with (i) the mature polypeptide coding sequence of SEQ ID NO: 1, or (ii) the full-length complement of (i);

c) a polypeptide encoded by a polynucleotide having at least 65% identity to the mature polypeptide coding sequence of SEQ ID NO: 1; and d) a fragment of the polypeptide of SEQ ID NO: 3, which has glucoamylase activity.

In an embodiment, the variant has sequence identity of at least 65%, at least 70%, at least 75%, at least 80%, at least 85%, at least 90%, at least 91%, at least 92%, at least 93%, at least 94%, at least 95%, at least 96%, at least 97%, at least 98%, or at least 99%, but less than 100%, to the amino acid sequence of the mature parent glucoamylase.

In another embodiment, the variant has at least 65%, at least 70%, at least 75%, at least 80%, at least 85%, at least 90%, at least 91%, at least 92%, at least 93%, at least 94%, at least 95%, such as at least 96%, at least 97%, at least 98%, or at least 99%, but less than 100%, sequence identity to the polypeptide of SEQ ID NO: 3.

In one aspect, the number of alterations in the variants of the present invention is 1-20, e.g., 1-10 and 1-5, such as 1, 2, 3, 4, 5, 6, 7, 8, 9 or 10 alterations.

In another aspect, the variant is encoded by a polynucleotide that hybridizes under very low stringency conditions, low stringency conditions, medium stringency conditions, medium-high stringency conditions, high stringency conditions, or very high stringency conditions with (i) the mature polypeptide coding sequence of SEQ ID NO: 1, or (ii) the full-length complement of (i) (Sambrook et al., 1989, *Molecular Cloning, A Laboratory Manual*, 2d edition, Cold Spring Harbor, N.Y.).

In another aspect, a variant comprises a substitution or deletion at one or more (e.g., several) positions corresponding to positions 1, 2, 3, 4, 5, 6, 7, 8, 10, 11, 12, 18, 26, 31, 33, 34, 65, 72, 74, 79, 80, 103, 105, 112, 161, 172, 218, 220, 221, 245, 253, 255, 279, 325, 327, 359, 364, 370, 375, 377, 405, 445, 447, 460, 463, 465, 468, 477, 501, 502, 504, 516, 524, 526, 563, 564, 568, and 571.

In another aspect, a variant comprises a substitution or deletion at two positions corresponding to any of positions 1, 2, 3, 4, 5, 6, 7, 8, 10, 11, 12, 18, 26, 31, 33, 34, 65, 72, 74, 79, 80, 103, 105, 112, 161, 172, 218, 220, 221, 245, 253, 255, 279, 325, 327, 359, 364, 370, 375, 377, 405, 445, 447, 460, 463, 465, 468, 477, 501, 502, 504, 516, 524, 526, 563, 564, 568, and 571.

In another aspect, a variant comprises a substitution or deletion at three positions corresponding to any of positions 1, 2, 3, 4, 5, 6, 7, 8, 10, 11, 12, 18, 26, 31, 33, 34, 65, 72, 74, 79, 80, 103, 105, 112, 161, 172, 218, 220, 221, 245, 253, 255, 279, 325, 327, 359, 364, 370, 375, 377, 405, 445, 447, 460, 463, 465, 468, 477, 501, 502, 504, 516, 524, 526, 563, 564, 568, and 571.

In another aspect, a variant comprises a substitution or deletion at four positions corresponding to any of positions 1, 2, 3, 4, 5, 6, 7, 8, 10, 11, 12, 18, 26, 31, 33, 34, 65, 72, 74, 79, 80, 103, 105, 112, 161, 172, 218, 220, 221, 245, 253, 255, 279, 325, 327, 359, 364, 370, 375, 377, 405, 445, 447, 460, 463, 465, 468, 477, 501, 502, 504, 516, 524, 526, 563, 564, 568, and 571.

In another aspect, a variant comprises a substitution or deletion at five positions corresponding to any of positions 1, 2, 3, 4, 5, 6, 7, 8, 10, 11, 12, 18, 26, 31, 33, 34, 65, 72, 74, 79, 80, 103, 105, 112, 161, 172, 218, 220, 221, 245, 253, 255, 279, 325, 327, 359, 364, 370, 375, 377, 405, 445, 447, 460, 463, 465, 468, 477, 501, 502, 504, 516, 524, 526, 563, 564, 568, and 571.

In another aspect, a variant comprises a substitution or deletion at six positions corresponding to any of positions 1, 2, 3, 4, 5, 6, 7, 8, 10, 11, 12, 18, 26, 31, 33, 34, 65, 72, 74, 79, 80, 103, 105, 112, 161, 172, 218, 220, 221, 245, 253, 255, 279, 325, 327, 359, 364, 370, 375, 377, 405, 445, 447, 460, 463, 465, 468, 477, 501, 502, 504, 516, 524, 526, 563, 564, 568, and 571.

In another aspect, a variant comprises a substitution or deletion at seven positions corresponding to any of positions 1, 2, 3, 4, 5, 6, 7, 8, 10, 11, 12, 18, 26, 31, 33, 34, 65, 72, 74, 79, 80, 103, 105, 112, 161, 172, 218, 220, 221, 245, 253, 255, 279, 325, 327, 359, 364, 370, 375, 377, 405, 445, 447, 460, 463, 465, 468, 477, 501, 502, 504, 516, 524, 526, 563, 564, 568, and 571.

In another aspect, a variant comprises a substitution or deletion at eight positions corresponding to any of positions 1, 2, 3, 4, 5, 6, 7, 8, 10, 11, 12, 18, 26, 31, 33, 34, 65, 72, 74, 79, 80, 103, 105, 112, 161, 172, 218, 220, 221, 245, 253, 255, 279, 325, 327, 359, 364, 370, 375, 377, 405, 445, 447, 460, 463, 465, 468, 477, 501, 502, 504, 516, 524, 526, 563, 564, 568, and 571.

In another aspect, a variant comprises a substitution or deletion at nine positions corresponding to any of positions 1, 2, 3, 4, 5, 6, 7, 8, 10, 11, 12, 18, 26, 31, 33, 34, 65, 72, 74, 79, 80, 103, 105, 112, 161, 172, 218, 220, 221, 245, 253, 255, 279, 325, 327, 359, 364, 370, 375, 377, 405, 445, 447, 460, 463, 465, 468, 477, 501, 502, 504, 516, 524, 526, 563, 564, 568, and 571.

In another aspect, a variant comprises a substitution or deletion at ten positions corresponding to any of positions 1, 2, 3, 4, 5, 6, 7, 8, 10, 11, 12, 18, 26, 31, 33, 34, 65, 72, 74, 79, 80, 103, 105, 112, 161, 172, 218, 220, 221, 245, 253, 255, 279, 325, 327, 359, 364, 370, 375, 377, 405, 445, 447, 460, 463, 465, 468, 477, 501, 502, 504, 516, 524, 526, 563, 564, 568, and 571.

In another aspect, a variant comprises a substitution or deletion at eleven positions corresponding to any of positions 1, 2, 3, 4, 5, 6, 7, 8, 10, 11, 12, 18, 26, 31, 33, 34, 65, 72, 74, 79, 80, 103, 105, 112, 161, 172, 218, 220, 221, 245, 253, 255, 279, 325, 327, 359, 364, 370, 375, 377, 405, 445, 447, 460, 463, 465, 468, 477, 501, 502, 504, 516, 524, 526, 563, 564, 568, and 571.

In another aspect, a variant comprises a substitution or deletion at twelve positions corresponding to any of positions 1, 2, 3, 4, 5, 6, 7, 8, 10, 11, 12, 18, 26, 31, 33, 34, 65, 72, 74, 79, 80, 103, 105, 112, 161, 172, 218, 220, 221, 245, 253, 255, 279, 325, 327, 359, 364, 370, 375, 377, 405, 445, 447, 460, 463, 465, 468, 477, 501, 502, 504, 516, 524, 526, 563, 564, 568, and 571.

In another aspect, a variant comprises a substitution or deletion at thirteen positions corresponding to any of positions 1, 2, 3, 4, 5, 6, 7, 8, 10, 11, 12, 18, 26, 31, 33, 34, 65, 72, 74, 79, 80, 103, 105, 112, 161, 172, 218, 220, 221, 245, 253, 255, 279, 325, 327, 359, 364, 370, 375, 377, 405, 445, 447, 460, 463, 465, 468, 477, 501, 502, 504, 516, 524, 526, 563, 564, 568, and 571.

In another aspect, a variant comprises a substitution or deletion at fourteen positions corresponding to any of positions 1, 2, 3, 4, 5, 6, 7, 8, 10, 11, 12, 18, 26, 31, 33, 34, 65, 72, 74, 79, 80, 103, 105, 112, 161, 172, 218, 220, 221, 245, 253, 255, 279, 325, 327, 359, 364, 370, 375, 377, 405, 445, 447, 460, 463, 465, 468, 477, 501, 502, 504, 516, 524, 526, 563, 564, 568, and 571.

In another aspect, a variant comprises a substitution or deletion at fifteen positions corresponding to any of positions 1, 2, 3, 4, 5, 6, 7, 8, 10, 11, 12, 18, 26, 31, 33, 34, 65, 72, 74, 79, 80, 103, 105, 112, 161, 172, 218, 220, 221, 245, 253, 255, 279, 325, 327, 359, 364, 370, 375, 377, 405, 445, 447, 460, 463, 465, 468, 477, 501, 502, 504, 516, 524, 526, 563, 564, 568, and 571.

In another aspect, the variant comprises or consists of a substitution at a position corresponding to position 1. In another aspect, the amino acid at a position corresponding to position 1 is substituted with Ala, Asn, Asp, Cys, Gln, Glu, Gly, His, Ile, Leu, Lys, Met, Phe, Pro, Ser, Thr, Trp, Tyr, or Val, preferably with Lys or Glu. In another aspect, the variant comprises or consists of the substitutions R1K or R1E of the polypeptide of SEQ ID NO: 3.

In another aspect, the variant comprises or consists of a substitution at a position corresponding to position 2. In another aspect, the amino acid at a position corresponding to position 2 is substituted with Ala, Arg, Asn, Asp, Cys, Gln, Glu, Gly, His, Ile, Leu, Lys, Met, Phe, Ser, Thr, Trp, Tyr, or Val, preferably with Asn. In another aspect, the variant comprises or consists of the substitution P2N of the polypeptide of SEQ ID NO: 3.

In another aspect, the variant comprises or consists of a substitution at a position corresponding to position 3. In another aspect, the amino acid at a position corresponding to position 3 is substituted with Ala, Arg, Asn, Cys, Gln, Glu, Gly, His, Ile, Leu, Lys, Met, Phe, Pro, Ser, Thr, Trp, Tyr, or Val, preferably with Trp or Asn. In another aspect, the variant comprises or consists of the substitutions D3W or D3N of the polypeptide of SEQ ID NO: 3.

In another aspect, the variant comprises or consists of a substitution at a position corresponding to position 4. In another aspect, the amino acid at a position corresponding to position 4 is substituted with Ala, Arg, Asn, Asp, Cys, Gln, Glu, Gly, His, Ile, Leu, Lys, Met, Phe, Ser, Thr, Trp, Tyr, or Val, preferably with Ser or Gly. In another aspect, the variant comprises or consists of the substitutions P4S or P4G of the polypeptide of SEQ ID NO: 3.

In another aspect, the variant comprises or consists of a substitution at a position corresponding to position 5. In another aspect, the amino acid at a position corresponding to position 5 is substituted with Ala, Arg, Asn, Asp, Cys, Gln, Glu, Gly, His, Ile, Leu, Met, Phe, Pro, Ser, Thr, Trp, Tyr, or Val, preferably with Ala or Gln. In another aspect, the variant comprises or consists of the substitutions K5A or K5Q of the polypeptide of SEQ ID NO: 3.

In another aspect, the variant comprises or consists of a substitution at a position corresponding to position 6. In another aspect, the amino acid at a position corresponding to position 6 is substituted with Ala, Arg, Asn, Asp, Cys, Gln, Glu, His, Ile, Leu, Lys, Met, Phe, Pro, Ser, Thr, Trp, Tyr, or Val, preferably with Arg. In another aspect, the variant comprises or consists of the substitution G6R of the polypeptide of SEQ ID NO: 3.

In another aspect, the variant comprises or consists of a substitution at a position corresponding to position 7. In another aspect, the amino acid at a position corresponding to position 7 is substituted with Ala, Arg, Asn, Asp, Cys, Gln, Glu, His, Ile, Leu, Lys, Met, Phe, Pro, Ser, Thr, Trp, Tyr, or Val, preferably with Ala or Val. In another aspect, the variant comprises or consists of the substitutions G7A or G7V of the polypeptide of SEQ ID NO: 3.

In another aspect, the variant comprises or consists of a substitution at a position corresponding to position 8. In another aspect, the amino acid at a position corresponding to position 8 is substituted with Ala, Arg, Asp, Cys, Gln, Glu, Gly, His, Ile, Leu, Lys, Met, Phe, Pro, Ser, Thr, Trp, Tyr, or Val, preferably with Ala or Ser. In another aspect, the variant comprises or consists of the substitutions N8A or N8S of the polypeptide of SEQ ID NO: 3.

In another aspect, the variant comprises or consists of a substitution at a position corresponding to position 10. In another aspect, the amino acid at a position corresponding to position 10 is substituted with Ala, Arg, Asn, Asp, Cys, Gln, Glu, Gly, His, Ile, Leu, Lys, Met, Phe, Pro, Ser, Trp, Tyr, or Val, preferably with Asp, Lys, or Glu. In another aspect, the variant comprises or consists of the substitutions T10D, T10K, or T10E of the polypeptide of SEQ ID NO: 3.

In another aspect, the variant comprises or consists of a substitution at a position corresponding to position 11. In another aspect, the amino acid at a position corresponding to position 11 is substituted with Ala, Arg, Asn, Asp, Cys, Gln, Glu, Gly, His, Ile, Leu, Lys, Met, Phe, Ser, Thr, Trp, Tyr, or Val, preferably with Asp, Phe, Ser, or Ala. In another aspect, the variant comprises or consists of the substitutions P11D, P11F, P11S, P11W, P11Y, P11H or P11A of the polypeptide of SEQ ID NO: 3.

In another aspect, the variant comprises or consists of a substitution at a position corresponding to position 12. In another aspect, the amino acid at a position corresponding to position 12 is substituted with Ala, Arg, Asn, Asp, Cys, Gln, Glu, Gly, His, Ile, Leu, Lys, Met, Pro, Ser, Thr, Trp, Tyr, or Val, preferably with Tyr. In another aspect, the variant comprises or consists of the substitution F12Y of the polypeptide of SEQ ID NO: 3.

In another aspect, the variant comprises or consists of a substitution at a position corresponding to position 18. In another aspect, the amino acid at a position corresponding to position 18 is substituted with Ala, Arg, Asn, Asp, Cys, Gln, Gly, His, Ile, Leu, Lys, Met, Phe, Pro, Ser, Thr, Trp, Tyr, or Val, preferably with Asn. In another aspect, the variant comprises or consists of the substitution E18N of the polypeptide of SEQ ID NO: 3.

In another aspect, the variant comprises or consists of a substitution at a position corresponding to position 26. In another aspect, the amino acid at a position corresponding to position 26 is substituted with Ala, Arg, Asn, Cys, Gln, Glu, Gly, His, Ile, Leu, Lys, Met, Phe, Pro, Ser, Thr, Trp, Tyr, or Val, preferably with Cys or Asn. In another aspect, the variant comprises or consists of the substitutions D26C or D26N of the polypeptide of SEQ ID NO: 3.

In another aspect, the variant comprises or consists of a substitution at a position corresponding to position 31. In another aspect, the amino acid at a position corresponding to position 31 is substituted with Ala, Asn, Asp, Cys, Gln, Glu, Gly, His, Ile, Leu, Lys, Met, Phe, Pro, Ser, Thr, Trp, Tyr, or Val, preferably with Ser. In another aspect, the variant comprises or consists of the substitution R31S of the polypeptide of SEQ ID NO: 3.

In another aspect, the variant comprises or consists of a substitution at a position corresponding to position 33. In another aspect, the amino acid at a position corresponding to position 33 is substituted with Ala, Arg, Asn, Asp, Cys, Gln, Glu, Gly, His, Ile, Leu, Met, Phe, Pro, Ser, Thr, Trp, Tyr, or Val, preferably with Cys or Val. In another aspect, the variant comprises or consists of the substitutions K33C or K33V of the polypeptide of SEQ ID NO: 3.

In another aspect, the variant comprises or consists of a substitution at a position corresponding to position 34. In another aspect, the amino acid at a position corresponding to position 34 is substituted with Ala, Arg, Asn, Asp, Cys, Gln, Glu, Gly, His, Ile, Leu, Met, Phe, Pro, Ser, Thr, Trp, Tyr, or Val, preferably with Tyr. In another aspect, the variant comprises or consists of the substitution K34Y of the polypeptide of SEQ ID NO: 3.

In another aspect, the variant comprises or consists of a substitution at a position corresponding to position 65. In another aspect, the amino acid at a position corresponding to position 65 is substituted with Ala, Arg, Asn, Asp, Cys, Gln, Glu, Gly, His, Ile, Leu, Lys, Met, Phe, Pro, Ser, Trp, Tyr, or Val, preferably with Ala. In another aspect, the variant comprises or consists of the substitution T65A of the polypeptide of SEQ ID NO: 3.

In another aspect, the variant comprises or consists of a substitution at a position corresponding to position 72. In another aspect, the amino acid at a position corresponding to position 72 is substituted with Ala, Arg, Asn, Asp, Cys, Gln, Glu, Gly, His, Ile, Lys, Met, Phe, Pro, Ser, Thr, Trp, Tyr, or Val, preferably with Val. In another aspect, the variant comprises or consists of the substitution L72V of the polypeptide of SEQ ID NO: 3.

In another aspect, the variant comprises or consists of a substitution at a position corresponding to position 74. In another aspect, the amino acid at a position corresponding to position 74 is substituted with Ala, Arg, Asn, Asp, Cys, Gln, Gly, His, Ile, Leu, Lys, Met, Phe, Pro, Ser, Thr, Trp, Tyr, or Val, preferably with Asn. In another aspect, the variant comprises or consists of the substitution E74N of the polypeptide of SEQ ID NO: 3.

In another aspect, the variant comprises or consists of a substitution at a position corresponding to position 79. In another aspect, the amino acid at a position corresponding to position 79 is substituted with Ala, Arg, Asn, Asp, Cys, Gln, Glu, Gly, His, Ile, Leu, Lys, Met, Phe, Pro, Ser, Thr, Trp, or Tyr, preferably with Ala, Gly, Ile, Leu, Lys, or Ser. In another aspect, the variant comprises or consists of the substitutions V79A, V79G, V79I, V79L, V79S, or V79K of the polypeptide of SEQ ID NO: 3.

In another aspect, the variant comprises or consists of a deletion at a position corresponding to position 80. In another aspect, the variant comprises or consists of the deletion F80* of the polypeptide of SEQ ID NO: 3.

In another aspect, the variant comprises or consists of a substitution at a position corresponding to position 103. In another aspect, the amino acid at a position corresponding to position 103 is substituted with Ala, Arg, Asn, Asp, Cys, Gln, Glu, Gly, His, Ile, Leu, Lys, Met, Phe, Pro, Thr, Trp, Tyr, or Val, preferably with Asn. In another aspect, the variant comprises or consists of the substitution S103N of the polypeptide of SEQ ID NO: 3.

In another aspect, the variant comprises or consists of a substitution at a position corresponding to position 105. In another aspect, the amino acid at a position corresponding to position 105 is substituted with Ala, Arg, Asn, Asp, Cys, Gln, Glu, Gly, His, Ile, Leu, Lys, Met, Phe, Pro, Thr, Trp, Tyr, or Val, preferably with Pro. In another aspect, the variant comprises or consists of the substitution S105P of the polypeptide of SEQ ID NO: 3.

In another aspect, the variant comprises or consists of a substitution at a position corresponding to position 112. In another aspect, the amino acid at a position corresponding to position 112 is substituted with Ala, Arg, Asn, Asp, Cys, Gln, Glu, Gly, His, Ile, Leu, Met, Phe, Pro, Ser, Thr, Trp, Tyr, or Val, preferably with Ser. In another aspect, the variant comprises or consists of the substitution K112S of the polypeptide of SEQ ID NO: 3.

In another aspect, the variant comprises or consists of a substitution at a position corresponding to position 161. In another aspect, the amino acid at a position corresponding to position 161 is substituted with Ala, Arg, Asn, Asp, Cys, Gln, Glu, Gly, His, Ile, Leu, Met, Phe, Pro, Ser, Thr, Trp, Tyr, or Val, preferably with Ser. In another aspect, the variant comprises or consists of the substitution K161S of the polypeptide of SEQ ID NO: 3.

In another aspect, the variant comprises or consists of a substitution at a position corresponding to position 172. In another aspect, the amino acid at a position corresponding to position 172 is substituted with Ala, Arg, Asn, Asp, Cys, Gln, Glu, Gly, His, Leu, Lys, Met, Phe, Pro, Ser, Thr, Trp, Tyr, or Val, preferably with Val. In another aspect, the variant comprises or consists of the substitution I172V of the polypeptide of SEQ ID NO: 3.

In another aspect, the variant comprises or consists of a substitution at a position corresponding to position 218. In another aspect, the amino acid at a position corresponding to position 218 is substituted with Ala, Arg, Asn, Asp, Cys, Gln, Glu, Gly, His, Ile, Leu, Met, Phe, Pro, Ser, Thr, Trp, Tyr, or Val, preferably with Ala. In another aspect, the variant comprises or consists of the substitution K218A of the polypeptide of SEQ ID NO: 3.

In another aspect, the variant comprises or consists of a substitution at a position corresponding to position 220. In another aspect, the amino acid at a position corresponding to position 220 is substituted with Ala, Arg, Asn, Asp, Cys, Gln, Glu, His, Ile, Leu, Lys, Met, Phe, Pro, Ser, Thr, Trp, Tyr, or Val, preferably with Asn. In another aspect, the variant comprises or consists of the substitution G220N of the polypeptide of SEQ ID NO: 3.

In another aspect, the variant comprises or consists of a substitution at a position corresponding to position 221. In another aspect, the amino acid at a position corresponding to position 221 is substituted with Ala, Arg, Asn, Asp, Cys, Gln, Glu, Gly, His, Ile, Leu, Met, Phe, Pro, Ser, Thr, Trp, Tyr, or Val, preferably with Asp. In another aspect, the variant comprises or consists of the substitution K221D of the polypeptide of SEQ ID NO: 3.

In another aspect, the variant comprises or consists of a substitution at a position corresponding to position 245. In another aspect, the amino acid at a position corresponding to position 245 is substituted with Ala, Arg, Asn, Asp, Cys, Gln, Glu, Gly, His, Ile, Leu, Lys, Met, Phe, Pro, Ser, Thr, Trp, or Val, preferably with Asn. In another aspect, the variant comprises or consists of the substitution Y245N of the polypeptide of SEQ ID NO: 3.

In another aspect, the variant comprises or consists of a substitution at a position corresponding to position 253. In another aspect, the amino acid at a position corresponding to position 253 is substituted with Ala, Arg, Asn, Asp, Cys, Glu, Gly, His, Ile, Leu, Lys, Met, Phe, Pro, Ser, Thr, Trp, Tyr, or Val, preferably with Asn. In another aspect, the variant comprises or consists of the substitution Q253N of the polypeptide of SEQ ID NO: 3.

In another aspect, the variant comprises or consists of a substitution at a position corresponding to position 255. In another aspect, the amino acid at a position corresponding to position 255 is substituted with Ala, Arg, Asn, Asp, Cys, Gln, Glu, Gly, His, Ile, Leu, Lys, Met, Phe, Pro, Thr, Trp, Tyr, or Val, preferably with Asn. In another aspect, the variant comprises or consists of the substitution S255N of the polypeptide of SEQ ID NO: 3.

In another aspect, the variant comprises or consists of a substitution at a position corresponding to position 279. In another aspect, the amino acid at a position corresponding to position 279 is substituted with Ala, Arg, Asn, Cys, Gln, Glu, Gly, His, Ile, Leu, Lys, Met, Phe, Pro, Ser, Thr, Trp, Tyr, or Val, preferably with Asn. In another aspect, the variant comprises or consists of the substitution D279N of the polypeptide of SEQ ID NO: 3.

In another aspect, the variant comprises or consists of a substitution at a position corresponding to position 325. In another aspect, the amino acid at a position corresponding to position 325 is substituted with Ala, Arg, Asn, Asp, Cys, Gln, Glu, Gly, His, Ile, Leu, Lys, Met, Phe, Pro, Ser, Thr, Trp, or Tyr, preferably with Thr. In another aspect, the variant comprises or consists of the substitution V325T of the polypeptide of SEQ ID NO: 3.

In another aspect, the variant comprises or consists of a substitution at a position corresponding to position 327. In another aspect, the amino acid at a position corresponding to position 327 is substituted with Ala, Arg, Asn, Asp, Cys, Glu, Gly, His, Ile, Leu, Lys, Met, Phe, Pro, Ser, Thr, Trp, Tyr, or Val, preferably with Trp, Tyr or Phe. In another aspect, the variant comprises or consists of the substitutions Q327W, Q327Y or Q327F of the polypeptide of SEQ ID NO: 3.

In another aspect, the variant comprises or consists of a substitution at a position corresponding to position 359. In another aspect, the amino acid at a position corresponding to position 359 is substituted with Ala, Arg, Asn, Asp, Cys, Gln, Glu, Gly, His, Ile, Leu, Lys, Met, Phe, Pro, Thr, Trp, Tyr, or Val, preferably with Asn. In another aspect, the variant comprises or consists of the substitution S359N of the polypeptide of SEQ ID NO: 3.

In another aspect, the variant comprises or consists of a substitution at a position corresponding to position 364. In another aspect, the amino acid at a position corresponding to position 364 is substituted with Ala, Arg, Asn, Asp, Cys, Gln, Glu, Gly, His, Ile, Leu, Lys, Met, Phe, Pro, Thr, Trp, Tyr, or Val, preferably with Pro. In another aspect, the variant comprises or consists of the substitution S364P of the polypeptide of SEQ ID NO: 3.

In another aspect, the variant comprises or consists of a substitution at a position corresponding to position 370 In another aspect, the amino acid at a position corresponding to position 370 is substituted with Ala, Arg, Asn, Cys, Gln, Glu, Gly, His, Ile, Leu, Lys, Met, Phe, Pro, Ser, Thr, Trp, Tyr, or Val, preferably with Asn. In another aspect, the variant comprises or consists of the substitution D370N of the polypeptide of SEQ ID NO: 3.

In another aspect, the variant comprises or consists of a substitution at a position corresponding to position 375. In another aspect, the amino acid at a position corresponding to position 375 is substituted with Ala, Arg, Asn, Asp, Cys, Gln, Glu, Gly, His, Leu, Lys, Met, Phe, Pro, Ser, Thr, Trp, Tyr, or Val, preferably with Ala. In another aspect, the variant comprises or consists of the substitution I375A of the polypeptide of SEQ ID NO: 3.

In another aspect, the variant comprises or consists of a substitution at a position corresponding to position 377. In another aspect, the amino acid at a position corresponding to position 377 is substituted with Ala, Arg, Asn, Asp, Cys, Gln, Glu, Gly, His, Ile, Leu, Lys, Met, Phe, Pro, Thr, Trp, Tyr, or Val, preferably with Thr. In another aspect, the variant comprises or consists of the substitution S377T of the polypeptide of SEQ ID NO: 3.

In another aspect, the variant comprises or consists of a substitution at a position corresponding to position 405. In another aspect, the amino acid at a position corresponding to position 405 is substituted with Ala, Arg, Asn, Asp, Cys, Glu, Gly, His, Ile, Leu, Lys, Met, Phe, Pro, Ser, Thr, Trp, Tyr, or Val, preferably with Thr. In another aspect, the variant comprises or consists of the substitution Q405T of the polypeptide of SEQ ID NO: 3.

In another aspect, the variant comprises or consists of a substitution at a position corresponding to position 445. In another aspect, the amino acid at a position corresponding to position 445 is substituted with Ala, Arg, Asn, Cys, Gln, Glu, Gly, His, Ile, Leu, Lys, Met, Phe, Pro, Ser, Thr, Trp, Tyr, or Val, preferably with Asn. In another aspect, the variant comprises or consists of the substitution D445N of the polypeptide of SEQ ID NO: 3.

In another aspect, the variant comprises or consists of a substitution at a position corresponding to position 447. In another aspect, the amino acid at a position corresponding to position 447 is substituted with Ala, Arg, Asn, Asp, Cys, Gln, Glu, Gly, His, Ile, Leu, Lys, Met, Phe, Pro, Ser, Thr, Trp, or Tyr, preferably with Ser. In another aspect, the variant comprises or consists of the substitution V447S of the polypeptide of SEQ ID NO: 3.

In another aspect, the variant comprises or consists of a substitution at a position corresponding to position 460. In another aspect, the amino acid at a position corresponding to position 460 is substituted with Ala, Arg, Asn, Asp, Cys, Gln, Glu, Gly, His, Ile, Leu, Lys, Met, Phe, Pro, Ser, Thr, Trp, or Tyr, preferably with Ser or Thr. In another aspect, the variant comprises or consists of the substitution V460S or V460T of the polypeptide of SEQ ID NO: 3.

In another aspect, the variant comprises or consists of a substitution at a position corresponding to position 463. In another aspect, the amino acid at a position corresponding to position 463 is substituted with Ala, Arg, Asn, Asp, Cys, Gln, Glu, Gly, His, Ile, Leu, Lys, Met, Phe, Pro, Ser, Trp, Tyr, or Val, preferably with Asn. In another aspect, the variant comprises or consists of the substitution T463N of the polypeptide of SEQ ID NO: 3.

In another aspect, the variant comprises or consists of a substitution at a position corresponding to position 465. In another aspect, the amino acid at a position corresponding to position 465 is substituted with Ala, Arg, Asn, Asp, Cys, Gln, Glu, Gly, His, Ile, Leu, Lys, Met, Phe, Pro, Thr, Trp, Tyr, or Val, preferably with Asn. In another aspect, the variant comprises or consists of the substitution S465N of the polypeptide of SEQ ID NO: 3.

In another aspect, the variant comprises or consists of a substitution at a position corresponding to position 468. In another aspect, the amino acid at a position corresponding to position 468 is substituted with Ala, Arg, Asn, Asp, Cys, Gln, Glu, Gly, His, Ile, Leu, Lys, Met, Phe, Ser, Thr, Trp, Tyr, or Val, preferably with Thr. In another aspect, the variant comprises or consists of the substitution P468T of the polypeptide of SEQ ID NO: 3.

In another aspect, the variant comprises or consists of a substitution at a position corresponding to position 477. In another aspect, the amino acid at a position corresponding to position 477 is substituted with Ala, Arg, Asn, Asp, Cys, Gln, Glu, Gly, His, Ile, Leu, Lys, Met, Phe, Pro, Ser, Trp, Tyr, or Val, preferably with Asn. In another aspect, the variant comprises or consists of the substitution T477N of the polypeptide of SEQ ID NO: 3.

In another aspect, the variant comprises or consists of a substitution at a position corresponding to position 501. In another aspect, the amino acid at a position corresponding to position 501 is substituted with Ala, Arg, Asn, Asp, Cys, Gln, Gly, His, Ile, Leu, Lys, Met, Phe, Pro, Ser, Thr, Trp, Tyr, or Val, preferably with Val. In another aspect, the variant comprises or consists of the substitution E501V of the polypeptide of SEQ ID NO: 3.

In another aspect, the variant comprises or consists of a substitution or deletion at a position corresponding to position 502. In another aspect, the amino acid at a position corresponding to position 502 is deleted or substituted with Ala, Arg, Asp, Cys, Gln, Glu, Gly, His, Ile, Leu, Lys, Met, Phe, Pro, Ser, Thr, Trp, Tyr, or Val, preferably with Thr. In another aspect, the variant comprises or consists of the alteration N502* or N502T of the polypeptide of SEQ ID NO: 3.

In another aspect, the variant comprises or consists of a substitution or deletion at a position corresponding to position 504. In another aspect, the amino acid at a position corresponding to position 504 is deleted or substituted with Ala, Arg, Asn, Asp, Cys, Gln, Glu, Gly, His, Ile, Leu, Lys, Met, Phe, Pro, Ser, Thr, Trp, or Val, preferably with Thr. In another aspect, the variant comprises or consists of the alteration Y504* or Y504T of the polypeptide of SEQ ID NO: 3.

In another aspect, the variant comprises or consists of a substitution at a position corresponding to position 516. In another aspect, the amino acid at a position corresponding to position 516 is substituted with Ala, Arg, Asn, Asp, Cys, Gln, Glu, Gly, His, Ile, Leu, Lys, Met, Phe, Pro, Ser, Trp, Tyr, or Val, preferably with Pro. In another aspect, the variant comprises or consists of the substitution T516P of the polypeptide of SEQ ID NO: 3.

In another aspect, the variant comprises or consists of a substitution at a position corresponding to position 524. In another aspect, the amino acid at a position corresponding to position 524 is substituted with Ala, Arg, Asn, Asp, Cys, Gln, Glu, Gly, His, Ile, Leu, Met, Phe, Pro, Ser, Thr, Trp, Tyr, or Val, preferably with Thr. In another aspect, the variant comprises or consists of the substitution K524T of the polypeptide of SEQ ID NO: 3.

In another aspect, the variant comprises or consists of a substitution at a position corresponding to position 526. In another aspect, the amino acid at a position corresponding to position 526 is substituted with Ala, Arg, Asn, Asp, Cys, Gln, Glu, His, Ile, Leu, Lys, Met, Phe, Pro, Ser, Thr, Trp, Tyr, or Val, preferably with Ala. In another aspect, the variant comprises or consists of the substitution G526A of the polypeptide of SEQ ID NO: 3.

In another aspect, the variant comprises or consists of a substitution at a position corresponding to position 563. In another aspect, the amino acid at a position corresponding to position 563 is substituted with Ala, Arg, Asn, Asp, Cys, Gln, Glu, Gly, His, Ile, Leu, Lys, Met, Phe, Ser, Thr, Trp, Tyr, or Val, preferably with Ser. In another aspect, the variant comprises or consists of the substitution P563S of the polypeptide of SEQ ID NO: 3.

In another aspect, the variant comprises or consists of a substitution at a position corresponding to position 564. In another aspect, the amino acid at a position corresponding to position 564 is substituted with Ala, Arg, Asp, Cys, Gln, Glu, Gly, His, Ile, Leu, Lys, Met, Phe, Pro, Ser, Thr, Trp, Tyr, or Val, preferably with Asp. In another aspect, the variant comprises or consists of the substitution N564D of the polypeptide of SEQ ID NO: 3.

In another aspect, the variant comprises or consists of a substitution at a position corresponding to position 568. In another aspect, the amino acid at a position corresponding to position 568 is substituted with Ala, Arg, Asn, Asp, Cys, Gln, Glu, Gly, His, Ile, Leu, Lys, Met, Phe, Pro, Ser, Trp, Tyr, or Val, preferably with Asn. In another aspect, the variant comprises or consists of the substitution T568N of the polypeptide of SEQ ID NO: 3.

In another aspect, the variant comprises or consists of a substitution at a position corresponding to position 571. In another aspect, the amino acid at a position corresponding to position 571 is substituted with Ala, Arg, Asn, Asp, Cys, Gln, Glu, Gly, His, Ile, Leu, Met, Phe, Pro, Ser, Thr, Trp, Tyr, or Val, preferably with Ser or Glu. In another aspect, the variant comprises or consists of the substitutions K571S or K571E of the polypeptide of SEQ ID NO: 3.

In another aspect, the variant comprises or consists of an alteration at positions corresponding to positions 65 and 327, such as those described above.

In another aspect, the variant comprises or consists of alterations at positions corresponding to positions 65 and 501, such as those described above.

In another aspect, the variant comprises or consists of alterations at positions corresponding to positions 65 and 504, such as those described above.

In another aspect, the variant comprises or consists of alterations at positions corresponding to positions 327 and 501, such as those described above.

In another aspect, the variant comprises or consists of alterations at positions corresponding to positions 327 and 504, such as those described above.

In another aspect, the variant comprises or consists of alterations at positions corresponding to positions 501 and 504, such as those described above.

In another aspect, the variant comprises or consists of alterations at positions corresponding to positions 65, 327, and 501, such as those described above.

In another aspect, the variant comprises or consists of alterations at positions corresponding to positions 65, 327, and 504, such as those described above.

In another aspect, the variant comprises or consists of alterations at positions corresponding to positions 65, 501, and 504, such as those described above.

In another aspect, the variant comprises or consists of alterations at positions corresponding to positions 327, 501, and 504, such as those described above.

In another aspect, the variant comprises or consists of alterations at positions corresponding to positions 65, 327, 501, and 504, such as those described above.

In another aspect, the variant comprises or consists of one or more (e.g., several) substitutions selected from the group consisting of T65A, Q327F, E501V, Y504T, Y504*.

In a further specific aspect the variant comprises one of the following substitutions or combinations of substitutions:
T65A; or
Q327F; or
E501V; or
Y504T; or
Y504*; or
T65A+Q327F; or
T65A+E501V; or
T65A+Y504T; or
T65A+Y504*; or
Q327F+E501V; or
Q327F+Y504T; or
Q327F+Y504*; or
E501V+Y504T; or
E501V+Y504*; or
T65A+Q327F+E501V; or
T65A+Q327F+Y504T; or
T65A+E501V+Y504T; or
Q327F+E501V+Y504T; or
T65A+Q327F+Y504*; or
T65A+E501V+Y504*; or
Q327F+E501V+Y504*; or
T65A+Q327F+E501V+Y504T; or
T65A+Q327F+E501V+Y504*

More specifically the variants according to the invention comprises or consist of the below combinations of substitutions or deletions to the polypeptide of SEQ ID NO: 3.
E501V+Y504T;
T65A+K161S;
T65A+Q405T;
T65A+Q327W;
T65A+Q327F;
T65A+Q327Y;
P11F+T65A+Q327F;
R1K+D3W+K5Q+G7V+N8S+T10K+P11S+T65A+Q327F;
P2N+P4S+P11F+T65A+Q327F;

P11F+D26C+K33C+T65A+Q327F;
P2N+P4S+P11F+T65A+Q327W+E501V+Y504T;
R1E+D3N+P4G+G6R+G7A+N8A+T10D+P11D+T65A+Q327F;
P11F+T65A+Q327W;
P2N+P4S+P11F+T65A+Q327F+E501V+Y504T;
P11F+T65A+Q327W+E501V+Y504T;
T65A+Q327F+E501V+Y504T;
T65A+S105P+Q327W;
T65A+S105P+Q327F;
T65A+Q327W+S364P;
T65A+Q327F+S364P;
T65A+S103N+Q327F;
P2N+P4S+P11F+K34Y+T65A+Q327F;
P2N+P4S+P11F+T65A+Q327F+D445N+V447S;
P2N+P4S+P11F+T65A+I172V+Q327F;
P2N+P4S+P11F+T65A+Q327F+N502*;
P2N+P4S+P11F+T65A+Q327F+N502T+P563S+K571E;
P2N+P4S+P11F+R31S+K33V+T65A+Q327F+N564D+K571S;
P2N+P4S+P11F+T65A+Q327F+S377T;
P2N+P4S+P11F+T65A+V325T+Q327W;
P2N+P4S+P11F+T65A+Q327F+D445N+V447S+E501V+Y504T;
P2N+P4S+P11F+T65A+I172V+Q327F+E501V+Y504T;
P2N+P4S+P11F+T65A+Q327F+S377T+E501V+Y504T;
P2N+P4S+P11F+D26N+K34Y+T65A+Q327F;
P2N+P4S+P11F+T65A+Q327F+I375A+E501V+Y504T;
P2N+P4S+P11F+T65A+K218A+K221D+Q327F+E501V+Y504T;
P2N+P4S+P11F+T65A+S103N+Q327F+E501V+Y504T;
P2N+P4S+T10D+T65A+Q327F+E501V+Y504T;
P2N+P4S+F12Y+T65A+Q327F+E501V+Y504T;
K5A+P11F+T65A+Q327F+E501V+Y504T;
P2N+P4S+T10E+E18N+T65A+Q327F+E501V+Y504T;
P2N+T10E+E18N+T65A+Q327F+E501V+Y504T;
P2N+P4S+P11F+T65A+Q327F+E501V+Y504T+T568N;
P2N+P4S+P11F+T65A+Q327F+E501V+Y504T+K524T+G526A;
P2N+P4S+P11F+K34Y+T65A+Q327F+D445N+V447S+E501V+Y504T;
P2N+P4S+P11F+R31S+K33V+T65A+Q327F+D445N+V447S+E501V+Y504T;
P2N+P4S+P11F+D26N+K34Y+T65A+Q327F+E501V+Y504T;
P2N+P4S+P11F+T65A+F80*+Q327F+E501V+Y504T;
P2N+P4S+P11F+T65A+K112S+Q327F+E501V+Y504T;
P2N+P4S+P11F+T65A+Q327F+E501V+Y504T+T516P+K524T+G526A;
P2N+P4S+P11F+T65A+Q327F+E501V+N502T+Y504*;
P2N+P4S+P11F+T65A+Q327F+E501V+Y504T;
P2N+P4S+P11F+T65A+S103N+Q327F+E501V+Y504T;
K5A+P11F+T65A+Q327F+E501V+Y504T;
P2N+P4S+P11F+T65A+Q327F+E501V+Y504T+T516P+K524T+G526A;
P2N+P4S+P11F+T65A+V79A+Q327F+E501V+Y504T;
P2N+P4S+P11F+T65A+V79G+Q327F+E501V+Y504T;
P2N+P4S+P11F+T65A+V79I+Q327F+E501V+Y504T;
P2N+P4S+P11F+T65A+V79L+Q327F+E501V+Y504T;
P2N+P4S+P11F+T65A+V79S+Q327F+E501V+Y504T;
P2N+P4S+P11F+T65A+L72V+Q327F+E501V+Y504T;
S255N+Q327F+E501V+Y504T;
P2N+P4S+P11F+T65A+E74N+V79K+Q327F+E501V+Y504T;
P2N+P4S+P11F+T65A+G220N+Q327F+E501V+Y504T;
P2N+P4S+P11F+T65A+Y245N+Q327F+E501V+Y504T;
P2N+P4S+P11F+T65A+Q253N+Q327F+E501V+Y504T;
P2N+P4S+P11F+T65A+D279N+Q327F+E501V+Y504T;
P2N+P4S+P11F+T65A+Q327F+S359N+E501V+Y504T;
P2N+P4S+P11F+T65A+Q327F+D370N+E501V+Y504T;
P2N+P4S+P11F+T65A+Q327F+V460S+E501V+Y504T;
P2N+P4S+P11F+T65A+Q327F+V460T+P468T+E501V+Y504T;
P2N+P4S+P11F+T65A+Q327F+T463N+E501V+Y504T;
P2N+P4S+P11F+T65A+Q327F+S465N+E501V+Y504T; or
P2N+P4S+P11F+T65A+Q327F+T477N+E501V+Y504T

The variants may further comprise one or more additional substitutions at one or more (e.g., several) other positions.

The amino acid changes may be of a minor nature, that is conservative amino acid substitutions or insertions that do not significantly affect the folding and/or activity of the protein; small deletions, typically of 1-30 amino acids; small amino- or carboxyl-terminal extensions, such as an amino-terminal methionine residue; a small linker peptide of up to 20-25 residues; or a small extension that facilitates purification by changing net charge or another function, such as a poly-histidine tract, an antigenic epitope or a binding domain.

Examples of conservative substitutions are within the groups of basic amino acids (arginine, lysine and histidine), acidic amino acids (glutamic acid and aspartic acid), polar amino acids (glutamine and asparagine), hydrophobic amino acids (leucine, isoleucine and valine), aromatic amino acids (phenylalanine, tryptophan and tyrosine), and small amino acids (glycine, alanine, serine, threonine and methionine). Amino acid substitutions that do not generally alter specific activity are known in the art and are described, for example, by H. Neurath and R. L. Hill, 1979, *In, The Proteins*, Academic Press, New York. Common substitutions are Ala/Ser, Val/Ile, Asp/Glu, Thr/Ser, Ala/Gly, Ala/Thr, Ser/Asn, Ala/Val, Ser/Gly, Tyr/Phe, Ala/Pro, Lys/Arg, Asp/Asn, Leu/Ile, Leu/Val, Ala/Glu, and Asp/Gly.

Alternatively, the amino acid changes are of such a nature that the physico-chemical properties of the polypeptides are altered. For example, amino acid changes may improve the thermal stability of the polypeptide, alter the substrate specificity, change the pH optimum, and the like.

Essential amino acids in a polypeptide can be identified according to procedures known in the art, such as site-directed mutagenesis or alanine-scanning mutagenesis (Cunningham and Wells, 1989, *Science* 244: 1081-1085). In the latter technique, single alanine mutations are introduced at every residue in the molecule, and the resultant mutant molecules are tested for glucoamylase activity to identify amino acid residues that are critical to the activity of the molecule. See also, Hilton et al., 1996, *J. Biol. Chem.* 271: 4699-4708. The active site of the enzyme or other biological interaction can also be determined by physical analysis of structure, as determined by such techniques as nuclear magnetic resonance, crystallography, electron diffraction, or photoaffinity labeling, in conjunction with mutation of putative contact site amino acids. See, for example, de Vos et al., 1992, *Science* 255: 306-312; Smith et al., 1992, *J. Mol. Biol.* 224: 899-904; Wlodaver et al., 1992, *FEBS Lett.* 309: 59-64. The identity of essential amino acids can also be inferred from an alignment with a related polypeptide.

Catalytic Domain Variants

In one embodiment the variants may consist of at least the catalytic domain of 465 amino acids, e.g. amino acids 30 to 494 in the parent glucoamylase shown as SEQ ID NO: 2, having the substitutions and/or deletions as described herein.

A second aspect of the present invention relates to a variant glucoamylase catalytic domain comprising a substitution at one or more positions corresponding to positions 10, 11, 12, 18, 26, 31, 33, 34, 65, 72, 74, 79, 80, 103, 105, 112, 161, 172, 218, 220, 221, 245, 253, 255, 279, 325, 327, 359, 364, 370, 375, 377, 405, 445, 447, 460, 463, 465, 468 of the polypeptide of SEQ ID NO: 3, wherein the variant has glucoamylase activity.

The variant glucoamylase catalytic domain may in one embodiment be selected from the group consisting of:

(a) a catalytic domain having at least 65% sequence identity to amino acids 30 to 494 of SEQ ID NO: 2;

(b) a catalytic domain encoded by a polynucleotide that hybridizes under medium stringency conditions with (i) nucleotides 88 to 1482 of SEQ ID NO: 1 or (ii) the full-length complement of (i);

(c) a catalytic domain encoded by a polynucleotide having at least 65% sequence identity to (i) nucleotides 88 to 1482 of SEQ ID NO: 1; and (d) a variant of amino acids 30 to 494 of SEQ ID NO: 2 comprising a substitution, deletion, and/or insertion at one or more (e.g., several) positions;
and wherein the catalytic domain has glucoamylase activity.

In one embodiment the catalytic domain may be considered to include the linker region from amino acids 495 to 506 of SEQ ID NO: 2. Amino acids 507 to 615 of SEQ ID NO: 2 correspond to a starch binding domain.

In an embodiment, the variant glucoamylase catalytic domain has sequence identity of at least 65%, at least 70%, at least 75%, at least 80%, at least 85%, at least 90%, at least 91%, at least 92%, at least 93%, at least 94%, at least 95%, at least 96%, at least 97%, at least 98%, or at least 99%, but less than 100%, to the amino acid sequence of the parent glucoamylase catalytic domain.

In another embodiment, the variant has at least 65%, at least 70%, at least 75%, at least 80%, at least 85%, at least 90%, at least 91%, at least 92%, at least 93%, at least 94%, at least 95%, such as at least 96%, at least 97%, at least 98%, or at least 99%, but less than 100%, sequence identity to the catalytic domain comprised in SEQ ID NO: 2, e.g. amino acids 30 to 494 of SEQ ID NO: 2.

In another aspect, the varian glucoamylase catalytic domain is encoded by a polynucleotide that hybridizes under very low stringency conditions, low stringency conditions, medium stringency conditions, medium-high stringency conditions, high stringency conditions, or very high stringency conditions with (i) the catalytic domain coding sequence of SEQ ID NO: 1, or (ii) the full-length complement of (i) or (ii) (Sambrook et al., 1989, *Molecular Cloning, A Laboratory Manual*, 2d edition, Cold Spring Harbor, N.Y.).

In an embodiment, the variant glucoamylase polypeptide has improved thermo-stability compared to the parent enzyme.

In one embodiment, the variant catalytic domain has improved thermostability compared to the parent catalytic domain.

Parent Glucoamylases

The parent glucoamylase may be (a) a polypeptide having at least 65% sequence identity to the mature polypeptide of SEQ ID NO: 2; (b) a polypeptide encoded by a polynucleotide that hybridizes under low stringency conditions with (i) the mature polypeptide coding sequence of SEQ ID NO: 1, or (ii) the full-length complement of (i); or (c) a polypeptide encoded by a polynucleotide having at least 65% sequence identity to the mature polypeptide coding sequence of SEQ ID NO: 1.

In an aspect, the parent has a sequence identity to the mature polypeptide of SEQ ID NO: 2 of at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100%, which have glucoamylase activity. In one aspect, the amino acid sequence of the parent differs by no more than 10 amino acids, e.g., 1, 2, 3, 4, 5, 6, 7, 8, or 9, from the mature polypeptide of SEQ ID NO: 2.

In another aspect, the parent comprises or consists of the amino acid sequence of SEQ ID NO: 2. In another aspect, the parent comprises or consists of the mature polypeptide of SEQ ID NO: 2. In another aspect, the parent comprises or consists of amino acids 30 to 494 of SEQ ID NO: 2.

In another aspect, the parent is a fragment of the mature polypeptide of SEQ ID NO: 2 containing at least 465 amino acid residues, e.g., at least 470 and at least 475 amino acid residues.

In another embodiment, the parent is an allelic variant of the mature polypeptide of SEQ ID NO: 2.

In another aspect, the parent is encoded by a polynucleotide that hybridizes under very low stringency conditions, low stringency conditions, medium stringency conditions, medium-high stringency conditions, high stringency conditions, or very high stringency conditions with (i) the mature polypeptide coding sequence of SEQ ID NO: 1, or (ii) the full-length complement of (i) or (ii) (Sambrook et al., 1989, *Molecular Cloning, A Laboratory Manual*, 2d edition, Cold Spring Harbor, N.Y.).

The polynucleotide of SEQ ID NO: 1 or a subsequence thereof, as well as the polypeptide of SEQ ID NO: 2 or a fragment thereof, may be used to design nucleic acid probes to identify and clone DNA encoding a parent from strains of different genera or species according to methods well known in the art. In particular, such probes can be used for hybridization with the genomic DNA or cDNA of a cell of interest, following standard Southern blotting procedures, in order to identify and isolate the corresponding gene therein. Such probes can be considerably shorter than the entire sequence, but should be at least 15, e.g., at least 25, at least 35, or at least 70 nucleotides in length. Preferably, the nucleic acid probe is at least 100 nucleotides in length, e.g., at least 200 nucleotides, at least 300 nucleotides, at least 400 nucleotides, at least 500 nucleotides, at least 600 nucleotides, at least 700 nucleotides, at least 800 nucleotides, or at least 900 nucleotides in length. Both DNA and RNA probes can be used. The probes are typically labeled for detecting the corresponding gene (for example, with $^{32}P$, $^{3}H$, $^{35}S$, biotin, or avidin). Such probes are encompassed by the present invention.

A genomic DNA or cDNA library prepared from such other strains may be screened for DNA that hybridizes with the probes described above and encodes a parent. Genomic or other DNA from such other strains may be separated by agarose or polyacrylamide gel electrophoresis, or other separation techniques. DNA from the libraries or the separated DNA may be transferred to and immobilized on nitrocellulose or other suitable carrier material. In order to identify a clone or DNA that hybridizes with SEQ ID NO: 1 or a subsequence thereof, the carrier material is used in a Southern blot.

For purposes of the present invention, hybridization indicates that the polynucleotide hybridizes to a labeled nucleic acid probe corresponding to (i) SEQ ID NO: 1; (ii) the mature polypeptide coding sequence of SEQ ID NO: 1; (iii) the full-length complement thereof; or (iv) a subsequence thereof; under very low to very high stringency conditions. Molecules to which the nucleic acid probe hybridizes under these conditions can be detected using, for example, X-ray film or any other detection means known in the art.

In one aspect, the nucleic acid probe is the mature polypeptide coding sequence of SEQ ID NO: 1. In another aspect, the nucleic acid probe is nucleotides 64 to 1848 of SEQ ID NO: 1. In another aspect, the nucleic acid probe is a polynucleotide that encodes the polypeptide of SEQ ID NO: 2; the mature polypeptide thereof; or a fragment thereof. In another aspect, the nucleic acid probe is SEQ ID NO: 1.

In another embodiment, the parent is encoded by a polynucleotide having a sequence identity to the mature polypeptide coding sequence of SEQ ID NO: 1 of at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100%.

The polypeptide may be a hybrid polypeptide in which a region of one polypeptide is fused at the N-terminus or the C-terminus of a region of another polypeptide.

The parent may be a fusion polypeptide or cleavable fusion polypeptide in which another polypeptide is fused at the N-terminus or the C-terminus of the polypeptide of the present invention. A fusion polypeptide is produced by fusing a polynucleotide encoding another polypeptide to a polynucleotide of the present invention. Techniques for producing fusion polypeptides are known in the art, and include ligating the coding sequences encoding the polypeptides so that they are in frame and that expression of the fusion polypeptide is under control of the same promoter(s) and terminator. Fusion polypeptides may also be constructed using intein technology in which fusion polypeptides are created post-translationally (Cooper et al., 1993, *EMBO J.* 12: 2575-2583; Dawson et al., 1994, *Science* 266: 776-779).

A fusion polypeptide can further comprise a cleavage site between the two polypeptides. Upon secretion of the fusion protein, the site is cleaved releasing the two polypeptides. Examples of cleavage sites include, but are not limited to, the sites disclosed in Martin et al., 2003, *J. Ind. Microbiol. Biotechnol.* 3: 568-576; Svetina et al., 2000, *J. Biotechnol.* 76: 245-251; Rasmussen-Wilson et al., 1997, *Appl. Environ. Microbiol.* 63: 3488-3493; Ward et al., 1995, *Biotechnology* 13: 498-503; and Contreras et al., 1991, *Biotechnology* 9: 378-381; Eaton et al., 1986, *Biochemistry* 25: 505-512; Collins-Racie et al., 1995, *Biotechnology* 13: 982-987; Carter et al., 1989, *Proteins: Structure, Function, and Genetics* 6: 240-248; and Stevens, 2003, *Drug Discovery World* 4: 35-48.

In one particular embodiment the hybrid polypeptide comprises the variant glucoamylase catalytic domain fused to a linker and a carbohydrate binding domain.

The parent may be obtained from microorganisms of any genus. For purposes of the present invention, the term "obtained from" as used herein in connection with a given source shall mean that the parent encoded by a polynucleotide is produced by the source or by a strain in which the polynucleotide from the source has been inserted. In one aspect, the parent is secreted extracellularly.

The parent may be a fungal glucoamylase. For example, the parent may be a *Penicillium* glucoamylase such as, e.g., a *Penicillium oxalicum* glucoamylase.

In another aspect, the parent is a *Penicillium oxalicum*, e.g., the glucoamylase of SEQ ID NO: 2 or the mature polypeptide thereof.

It will be understood that for the aforementioned species, the invention encompasses both the perfect and imperfect states, and other taxonomic equivalents, e.g., anamorphs, regardless of the species name by which they are known. Those skilled in the art will readily recognize the identity of appropriate equivalents.

Strains of these species are readily accessible to the public in a number of culture collections, such as the American Type Culture Collection (ATCC), Deutsche Sammlung von Mikroorganismen and Zellkulturen GmbH (DSMZ), Centraalbureau Voor Schimmelcultures (CBS), and Agricultural Research Service Patent Culture Collection, Northern Regional Research Center (NRRL).

The parent may be identified and obtained from other sources including microorganisms isolated from nature (e.g., soil, composts, water, etc.) or DNA samples obtained directly from natural materials (e.g., soil, composts, water, etc.) using the above-mentioned probes. Techniques for isolating microorganisms and DNA directly from natural habitats are well known in the art. A polynucleotide encoding a parent may then be obtained by similarly screening a genomic DNA or cDNA library of another microorganism or mixed DNA sample. Once a polynucleotide encoding a parent has been detected with the probe(s), the polynucleotide can be isolated or cloned by utilizing techniques that are known to those of ordinary skill in the art (see, e.g., Sambrook et al., 1989, supra).

Preparation of Variants

The variants can be prepared using any mutagenesis procedure known in the art, such as site-directed mutagenesis, synthetic gene construction, semi-synthetic gene construction, random mutagenesis, shuffling, etc.

Site-directed mutagenesis is a technique in which one or more (e.g., several) mutations are introduced at one or more defined sites in a polynucleotide encoding the parent.

Site-directed mutagenesis can be accomplished in vitro by PCR involving the use of oligonucleotide primers containing the desired mutation. Site-directed mutagenesis can also be performed in vitro by cassette mutagenesis involving the cleavage by a restriction enzyme at a site in the plasmid comprising a polynucleotide encoding the parent and subsequent ligation of an oligonucleotide containing the mutation in the polynucleotide. Usually the restriction enzyme that digests the plasmid and the oligonucleotide is the same, permitting sticky ends of the plasmid and the insert to ligate to one another. See, e.g., Scherer and Davis, 1979, *Proc. Natl. Acad. Sci. USA* 76: 4949-4955; and Barton et al., 1990, *Nucleic Acids Res.* 18: 7349-4966.

Site-directed mutagenesis can also be accomplished in vivo by methods known in the art. See, e.g., U.S. Patent Application Publication No. 2004/0171154; Storici et al., 2001, *Nature Biotechnol.* 19: 773-776; Kren et al., 1998, *Nat. Med.* 4: 285-290; and Calissano and Macino, 1996, *Fungal Genet. Newslett.* 43: 15-16.

Any site-directed mutagenesis procedure can be used in the present invention. There are many commercial kits available that can be used to prepare variants.

Synthetic gene construction entails in vitro synthesis of a designed polynucleotide molecule to encode a polypeptide of interest. Gene synthesis can be performed utilizing a number of techniques, such as the multiplex microchip-based technology described by Tian et al. (2004, *Nature* 432: 1050-1054) and similar technologies wherein oligonucleotides are synthesized and assembled upon photo-programmable microfluidic chips.

Single or multiple amino acid substitutions, deletions, and/or insertions can be made and tested using known methods of mutagenesis, recombination, and/or shuffling, followed by a relevant screening procedure, such as those disclosed by Reidhaar-Olson and Sauer, 1988, *Science* 241:

53-57; Bowie and Sauer, 1989, *Proc. Natl. Acad. Sci. USA* 86: 2152-2156; WO 95/17413; or WO 95/22625. Other methods that can be used include error-prone PCR, phage display (e.g., Lowman et al., 1991, *Biochemistry* 30: 10832-10837; U.S. Pat. No. 5,223,409; WO 92/06204) and region-directed mutagenesis (Derbyshire et al., 1986, *Gene* 46: 145; Ner et al., 1988, *DNA* 7: 127).

Mutagenesis/shuffling methods can be combined with high-throughput, automated screening methods to detect activity of cloned, mutagenized polypeptides expressed by host cells (Ness et al., 1999, *Nature Biotechnology* 17: 893-896). Mutagenized DNA molecules that encode active polypeptides can be recovered from the host cells and rapidly sequenced using standard methods in the art. These methods allow the rapid determination of the importance of individual amino acid residues in a polypeptide.

Semi-synthetic gene construction is accomplished by combining aspects of synthetic gene construction, and/or site-directed mutagenesis, and/or random mutagenesis, and/or shuffling. Semi-synthetic construction is typified by a process utilizing polynucleotide fragments that are synthesized, in combination with PCR techniques. Defined regions of genes may thus be synthesized de novo, while other regions may be amplified using site-specific mutagenic primers, while yet other regions may be subjected to error-prone PCR or non-error prone PCR amplification. Polynucleotide subsequences may then be shuffled.

Polynucleotides

The present invention also relates to isolated polynucleotides encoding a variant of the present invention.

Nucleic Acid Constructs

The present invention also relates to nucleic acid constructs comprising a polynucleotide encoding a variant of the present invention operably linked to one or more control sequences that direct the expression of the coding sequence in a suitable host cell under conditions compatible with the control sequences.

The polynucleotide may be manipulated in a variety of ways to provide for expression of a variant. Manipulation of the polynucleotide prior to its insertion into a vector may be desirable or necessary depending on the expression vector. The techniques for modifying polynucleotides utilizing recombinant DNA methods are well known in the art.

The control sequence may be a promoter, a polynucleotide which is recognized by a host cell for expression of the polynucleotide. The promoter contains transcriptional control sequences that mediate the expression of the variant. The promoter may be any polynucleotide that shows transcriptional activity in the host cell including mutant, truncated, and hybrid promoters, and may be obtained from genes encoding extracellular or intracellular polypeptides either homologous or heterologous to the host cell.

Examples of suitable promoters for directing transcription of the nucleic acid constructs of the present invention in a bacterial host cell are the promoters obtained from the *Bacillus amyloliquefaciens* alpha-amylase gene (amyQ), *Bacillus licheniformis* alpha-amylase gene (amyL), *Bacillus licheniformis* penicillinase gene (penP), *Bacillus stearothermophilus* maltogenic amylase gene (amyM), *Bacillus subtilis* levansucrase gene (sacB), *Bacillus subtilis* xylA and xylB genes, *Bacillus thuringiensis* cryIIIA gene (Agaisse and Lereclus, 1994, *Molecular Microbiology* 13: 97-107), *E. coli* lac operon, *E. coli* trc promoter (Egon et al., 1988, *Gene* 69: 301-315), *Streptomyces coelicolor* agarase gene (dagA), and prokaryotic beta-lactamase gene (Villa-Kamaroff et al., 1978, *Proc. Natl. Acad. Sci. USA* 75: 3727-3731), as well as the tac promoter (DeBoer et al., 1983, *Proc. Natl. Acad. Sci. USA* 80: 21-25). Further promoters are described in "Useful proteins from recombinant bacteria" in Gilbert et al., 1980, *Scientific American* 242: 74-94; and in Sambrook et al., 1989, supra. Examples of tandem promoters are disclosed in WO 99/43835.

Examples of suitable promoters for directing transcription of the nucleic acid constructs of the present invention in a filamentous fungal host cell are promoters obtained from the genes for *Aspergillus nidulans* acetamidase, *Aspergillus niger* neutral alpha-amylase, *Aspergillus niger* acid stable alpha-amylase, *Aspergillus niger* or *Aspergillus awamori* glucoamylase (glaA), *Aspergillus oryzae* TAKA amylase, *Aspergillus oryzae* alkaline protease, *Aspergillus oryzae* triose phosphate isomerase, *Fusarium oxysporum* trypsin-like protease (WO 96/00787), *Fusarium venenatum* amyloglucosidase (WO 00/56900), *Fusarium venenatum* Daria (WO 00/56900), *Fusarium venenatum* Quinn (WO 00/56900), *Rhizomucor miehei* lipase, *Rhizomucor miehei* aspartic proteinase, *Trichoderma reesei* beta-glucosidase, *Trichoderma reesei* cellobiohydrolase I, *Trichoderma reesei* cellobiohydrolase II, *Trichoderma reesei* endoglucanase I, *Trichoderma reesei* endoglucanase II, *Trichoderma reesei* endoglucanase III, *Trichoderma reesei* endoglucanase IV, *Trichoderma reesei* endoglucanase V, *Trichoderma reesei* xylanase I, *Trichoderma reesei* xylanase II, *Trichoderma reesei* beta-xylosidase, as well as the NA2-tpi promoter (a modified promoter from an *Aspergillus* neutral alpha-amylase gene in which the untranslated leader has been replaced by an untranslated leader from an *Aspergillus* triose phosphate isomerase gene; non-limiting examples include modified promoters from an *Aspergillus niger* neutral alpha-amylase gene in which the untranslated leader has been replaced by an untranslated leader from an *Aspergillus nidulans* or *Aspergillus oryzae* triose phosphate isomerase gene); and mutant, truncated, and hybrid promoters thereof.

In a yeast host, useful promoters are obtained from the genes for *Saccharomyces cerevisiae* enolase (ENO-1), *Saccharomyces cerevisiae* galactokinase (GAL1), *Saccharomyces cerevisiae* alcohol dehydrogenase/glyceraldehyde-3-phosphate dehydrogenase (ADH1, ADH2/GAP), *Saccharomyces cerevisiae* triose phosphate isomerase (TPI), *Saccharomyces cerevisiae* metallothionein (CUP1), and *Saccharomyces cerevisiae* 3-phosphoglycerate kinase. Other useful promoters for yeast host cells are described by Romanos et al., 1992, *Yeast* 8: 423-488.

The control sequence may also be a transcription terminator, which is recognized by a host cell to terminate transcription. The terminator sequence is operably linked to the 3'-terminus of the polynucleotide encoding the variant. Any terminator that is functional in the host cell may be used.

Preferred terminators for bacterial host cells are obtained from the genes for *Bacillus clausii* alkaline protease (aprH), *Bacillus licheniformis* alpha-amylase (amyL), and *Escherichia coli* ribosomal RNA (rrnB).

Preferred terminators for filamentous fungal host cells are obtained from the genes for *Aspergillus nidulans* anthranilate synthase, *Aspergillus niger* glucoamylase, *Aspergillus niger* alpha-glucosidase, *Aspergillus oryzae* TAKA amylase, and *Fusarium oxysporum* trypsin-like protease.

Preferred terminators for yeast host cells are obtained from the genes for *Saccharomyces cerevisiae* enolase, *Saccharomyces cerevisiae* cytochrome C (CYC1), and *Saccharomyces cerevisiae* glyceraldehyde-3-phosphate dehydrogenase. Other useful terminators for yeast host cells are described by Romanos et al., 1992, supra.

The control sequence may also be an mRNA stabilizer region downstream of a promoter and upstream of the coding sequence of a gene which increases expression of the gene.

Examples of suitable mRNA stabilizer regions are obtained from a *Bacillus thuringiensis* cryIIIA gene (WO 94/25612) and a *Bacillus subtilis* SP82 gene (Hue et al., 1995, *Journal of Bacteriology* 177: 3465-3471).

The control sequence may also be a leader, a nontranslated region of an mRNA that is important for translation by the host cell. The leader sequence is operably linked to the 5'-terminus of the polynucleotide encoding the variant. Any leader that is functional in the host cell may be used.

Preferred leaders for filamentous fungal host cells are obtained from the genes for *Aspergillus oryzae* TAKA amylase and *Aspergillus nidulans* triose phosphate isomerase.

Suitable leaders for yeast host cells are obtained from the genes for *Saccharomyces cerevisiae* enolase (ENO-1), *Saccharomyces cerevisiae* 3-phosphoglycerate kinase, *Saccharomyces cerevisiae* alpha-factor, and *Saccharomyces cerevisiae* alcohol dehydrogenase/glyceraldehyde-3-phosphate dehydrogenase (ADH2/GAP).

The control sequence may also be a polyadenylation sequence, a sequence operably linked to the 3'-terminus of the variant-encoding sequence and, when transcribed, is recognized by the host cell as a signal to add polyadenosine residues to transcribed mRNA. Any polyadenylation sequence that is functional in the host cell may be used.

Preferred polyadenylation sequences for filamentous fungal host cells are obtained from the genes for *Aspergillus nidulans* anthranilate synthase, *Aspergillus niger* glucoamylase, *Aspergillus niger* alpha-glucosidase, *Aspergillus oryzae* TAKA amylase, and *Fusarium oxysporum* trypsin-like protease.

Useful polyadenylation sequences for yeast host cells are described by Guo and Sherman, 1995, *Mol. Cellular Biol.* 15: 5983-5990.

The control sequence may also be a signal peptide coding region that encodes a signal peptide linked to the N-terminus of a variant and directs the variant into the cell's secretory pathway. The 5'-end of the coding sequence of the polynucleotide may inherently contain a signal peptide coding sequence naturally linked in translation reading frame with the segment of the coding sequence that encodes the variant. Alternatively, the 5'-end of the coding sequence may contain a signal peptide coding sequence that is foreign to the coding sequence. A foreign signal peptide coding sequence may be required where the coding sequence does not naturally contain a signal peptide coding sequence. Alternatively, a foreign signal peptide coding sequence may simply replace the natural signal peptide coding sequence in order to enhance secretion of the variant. However, any signal peptide coding sequence that directs the expressed variant into the secretory pathway of a host cell may be used.

Effective signal peptide coding sequences for bacterial host cells are the signal peptide coding sequences obtained from the genes for *Bacillus* NCIB 11837 maltogenic amylase, *Bacillus licheniformis* subtilisin, *Bacillus licheniformis* beta-lactamase, *Bacillus stearothermophilus* alpha-amylase, *Bacillus stearothermophilus* neutral proteases (nprT, nprS, nprM), and *Bacillus subtilis* prsA. Further signal peptides are described by Simonen and Palva, 1993, *Microbiological Reviews* 57: 109-137.

Effective signal peptide coding sequences for filamentous fungal host cells are the signal peptide coding sequences obtained from the genes for *Aspergillus niger* neutral amylase, *Aspergillus niger* glucoamylase, *Aspergillus oryzae* TAKA amylase, *Humicola insolens* cellulase, *Humicola insolens* endoglucanase V, *Humicola lanuginosa* lipase, and *Rhizomucor miehei* aspartic proteinase.

Useful signal peptides for yeast host cells are obtained from the genes for *Saccharomyces cerevisiae* alpha-factor and *Saccharomyces cerevisiae* invertase. Other useful signal peptide coding sequences are described by Romanos et al., 1992, supra.

The control sequence may also be a propeptide coding sequence that encodes a propeptide positioned at the N-terminus of a variant. The resultant polypeptide is known as a proenzyme or propolypeptide (or a zymogen in some cases). A propolypeptide is generally inactive and can be converted to an active polypeptide by catalytic or autocatalytic cleavage of the propeptide from the propolypeptide. The propeptide coding sequence may be obtained from the genes for *Bacillus subtilis* alkaline protease (aprE), *Bacillus subtilis* neutral protease (nprT), *Myceliophthora thermophila* laccase (WO 95/33836), *Rhizomucor miehei* aspartic proteinase, and *Saccharomyces cerevisiae* alpha-factor.

Where both signal peptide and propeptide sequences are present, the propeptide sequence is positioned next to the N-terminus of the variant and the signal peptide sequence is positioned next to the N-terminus of the propeptide sequence.

It may also be desirable to add regulatory sequences that regulate expression of the variant relative to the growth of the host cell. Examples of regulatory systems are those that cause expression of the gene to be turned on or off in response to a chemical or physical stimulus, including the presence of a regulatory compound. Regulatory systems in prokaryotic systems include the lac, tac, and trp operator systems. In yeast, the ADH2 system or GAL1 system may be used. In filamentous fungi, the *Aspergillus niger* glucoamylase promoter, *Aspergillus oryzae* TAKA alpha-amylase promoter, and *Aspergillus oryzae* glucoamylase promoter may be used. Other examples of regulatory sequences are those that allow for gene amplification. In eukaryotic systems, these regulatory sequences include the dihydrofolate reductase gene that is amplified in the presence of methotrexate, and the metallothionein genes that are amplified with heavy metals. In these cases, the polynucleotide encoding the variant would be operably linked with the regulatory sequence.

Expression Vectors

The present invention also relates to recombinant expression vectors comprising a polynucleotide encoding a variant of the present invention, a promoter, and transcriptional and translational stop signals. The various nucleotide and control sequences may be joined together to produce a recombinant expression vector that may include one or more convenient restriction sites to allow for insertion or substitution of the polynucleotide encoding the variant at such sites. Alternatively, the polynucleotide may be expressed by inserting the polynucleotide or a nucleic acid construct comprising the polynucleotide into an appropriate vector for expression. In creating the expression vector, the coding sequence is located in the vector so that the coding sequence is operably linked with the appropriate control sequences for expression.

The recombinant expression vector may be any vector (e.g., a plasmid or virus) that can be conveniently subjected to recombinant DNA procedures and can bring about expression of the polynucleotide. The choice of the vector will typically depend on the compatibility of the vector with the host cell into which the vector is to be introduced. The vector may be a linear or closed circular plasmid.

The vector may be an autonomously replicating vector, i.e., a vector that exists as an extrachromosomal entity, the replication of which is independent of chromosomal replication, e.g., a plasmid, an extrachromosomal element, a minichromosome, or an artificial chromosome. The vector may contain any means for assuring self-replication. Alternatively, the vector may be one that, when introduced into the host cell, is integrated into the genome and replicated together with the chromosome(s) into which it has been integrated. Furthermore, a single vector or plasmid or two or more vectors or plasmids that together contain the total DNA to be introduced into the genome of the host cell, or a transposon, may be used.

The vector preferably contains one or more selectable markers that permit easy selection of transformed, transfected, transduced, or the like cells. A selectable marker is a gene the product of which provides for biocide or viral resistance, resistance to heavy metals, prototrophy to auxotrophs, and the like.

Examples of bacterial selectable markers are *Bacillus licheniformis* or *Bacillus subtilis* dal genes, or markers that confer antibiotic resistance such as ampicillin, chloramphenicol, kanamycin, neomycin, spectinomycin or tetracycline resistance. Suitable markers for yeast host cells include, but are not limited to, ADE2, HIS3, LEU2, LYS2, MET3, TRP1, and URA3. Selectable markers for use in a filamentous fungal host cell include, but are not limited to, amdS (acetamidase), argB (ornithine carbamoyltransferase), bar (phosphinothricin acetyltransferase), hph (hygromycin phosphotransferase), niaD (nitrate reductase), pyrG (orotidine-5'-phosphate decarboxylase), sC (sulfate adenyltransferase), and trpC (anthranilate synthase), as well as equivalents thereof. Preferred for use in an *Aspergillus* cell are *Aspergillus nidulans* or *Aspergillus oryzae* amdS and pyrG genes and a *Streptomyces hygroscopicus* bar gene.

The vector preferably contains an element(s) that permits integration of the vector into the host cell's genome or autonomous replication of the vector in the cell independent of the genome.

For integration into the host cell genome, the vector may rely on the polynucleotide's sequence encoding the variant or any other element of the vector for integration into the genome by homologous or non-homologous recombination. Alternatively, the vector may contain additional polynucleotides for directing integration by homologous recombination into the genome of the host cell at a precise location(s) in the chromosome(s). To increase the likelihood of integration at a precise location, the integrational elements should contain a sufficient number of nucleic acids, such as 100 to 10,000 base pairs, 400 to 10,000 base pairs, and 800 to 10,000 base pairs, which have a high degree of sequence identity to the corresponding target sequence to enhance the probability of homologous recombination. The integrational elements may be any sequence that is homologous with the target sequence in the genome of the host cell. Furthermore, the integrational elements may be non-encoding or encoding polynucleotides. On the other hand, the vector may be integrated into the genome of the host cell by non-homologous recombination.

For autonomous replication, the vector may further comprise an origin of replication enabling the vector to replicate autonomously in the host cell in question. The origin of replication may be any plasmid replicator mediating autonomous replication that functions in a cell. The term "origin of replication" or "plasmid replicator" means a polynucleotide that enables a plasmid or vector to replicate in vivo.

Examples of bacterial origins of replication are the origins of replication of plasmids pBR322, pUC19, pACYC177, and pACYC184 permitting replication in *E. coli*, and pUB110, pE194, pTA1060, and pAMβ1 permitting replication in *Bacillus*.

Examples of origins of replication for use in a yeast host cell are the 2 micron origin of replication, ARS1, ARS4, the combination of ARS1 and CEN3, and the combination of ARS4 and CEN6.

Examples of origins of replication useful in a filamentous fungal cell are AMA1 and ANSI (Gems et al., 1991, *Gene* 98: 61-67; Cullen et al., 1987, *Nucleic Acids Res.* 15: 9163-9175; WO 00/24883). Isolation of the AMA1 gene and construction of plasmids or vectors comprising the gene can be accomplished according to the methods disclosed in WO 00/24883.

More than one copy of a polynucleotide of the present invention may be inserted into a host cell to increase production of a variant. An increase in the copy number of the polynucleotide can be obtained by integrating at least one additional copy of the sequence into the host cell genome or by including an amplifiable selectable marker gene with the polynucleotide where cells containing amplified copies of the selectable marker gene, and thereby additional copies of the polynucleotide, can be selected for by cultivating the cells in the presence of the appropriate selectable agent.

The procedures used to ligate the elements described above to construct the recombinant expression vectors of the present invention are well known to one skilled in the art (see, e.g., Sambrook et al., 1989, supra).

Host Cells

The present invention also relates to recombinant host cells, comprising a polynucleotide encoding a variant of the present invention operably linked to one or more control sequences that direct the production of a variant of the present invention. A construct or vector comprising a polynucleotide is introduced into a host cell so that the construct or vector is maintained as a chromosomal integrant or as a self-replicating extra-chromosomal vector as described earlier. The term "host cell" encompasses any progeny of a parent cell that is not identical to the parent cell due to mutations that occur during replication. The choice of a host cell will to a large extent depend upon the gene encoding the variant and its source.

The host cell may be any cell useful in the recombinant production of a variant, e.g., a prokaryote or a eukaryote.

The prokaryotic host cell may be any Gram-positive or Gram-negative bacterium. Gram-positive bacteria include, but are not limited to, *Bacillus, Clostridium, Enterococcus, Geobacillus, Lactobacillus, Lactococcus, Oceanobacillus, Staphylococcus, Streptococcus,* and *Streptomyces.* Gram-negative bacteria include, but are not limited to, *Campylobacter, E. coli, Flavobacterium, Fusobacterium, Helicobacter, Ilyobacter, Neisseria, Pseudomonas, Salmonella,* and *Ureaplasma.*

The bacterial host cell may be any *Bacillus* cell including, but not limited to, *Bacillus alkalophilus, Bacillus amyloliquefaciens, Bacillus brevis, Bacillus circulans, Bacillus clausii, Bacillus coagulans, Bacillus firmus, Bacillus lautus, Bacillus lentus, Bacillus licheniformis, Bacillus megaterium, Bacillus pumilus, Bacillus stearothermophilus, Bacillus subtilis,* and *Bacillus thuringiensis* cells.

The bacterial host cell may also be any *Streptococcus* cell including, but not limited to, *Streptococcus equisimilis,*

*Streptococcus pyogenes, Streptococcus uberis*, and *Streptococcus equi* subsp. *Zooepidemicus* cells.

The bacterial host cell may also be any *Streptomyces* cell, including, but not limited to, *Streptomyces achromogenes, Streptomyces avermitilis, Streptomyces coelicolor, Streptomyces griseus*, and *Streptomyces lividans* cells.

The introduction of DNA into a *Bacillus* cell may be effected by protoplast transformation (see, e.g., Chang and Cohen, 1979, *Mol. Gen. Genet.* 168: 111-115), competent cell transformation (see, e.g., Young and Spizizen, 1961, *J. Bacteriol.* 81: 823-829, or Dubnau and Davidoff-Abelson, 1971, *J. Mol. Biol.* 56: 209-221), electroporation (see, e.g., Shigekawa and Dower, 1988, *Biotechniques* 6: 742-751), or conjugation (see, e.g., Koehler and Thorne, 1987, *J. Bacteriol.* 169: 5271-5278). The introduction of DNA into an *E. coli* cell may be effected by protoplast transformation (see, e.g., Hanahan, 1983, *J. Mol. Biol.* 166: 557-580) or electroporation (see, e.g., Dower et al., 1988, *Nucleic Acids Res.* 16: 6127-6145). The introduction of DNA into a *Streptomyces* cell may be effected by protoplast transformation, electroporation (see, e.g., Gong et al., 2004, *Folia Microbiol. (Praha)* 49: 399-405), conjugation (see, e.g., Mazodier et al., 1989, *J. Bacteriol.* 171: 3583-3585), or transduction (see, e.g., Burke et al., 2001, *Proc. Natl. Acad. Sci. USA* 98: 6289-6294). The introduction of DNA into a *Pseudomonas* cell may be effected by electroporation (see, e.g., Choi et al., 2006, *J. Microbiol. Methods* 64: 391-397), or conjugation (see, e.g., Pinedo and Smets, 2005, *Appl. Environ. Microbiol.* 71: 51-57). The introduction of DNA into a *Streptococcus* cell may be effected by natural competence (see, e.g., Perry and Kuramitsu, 1981, *Infect. Immun.* 32: 1295-1297), protoplast transformation (see, e.g., Catt and Jollick, 1991, *Microbios* 68: 189-207), electroporation (see, e.g., Buckley et al., 1999, *Appl. Environ. Microbiol.* 65: 3800-3804) or conjugation (see, e.g., Clewell, 1981, *Microbiol. Rev.* 45: 409-436). However, any method known in the art for introducing DNA into a host cell can be used.

The host cell may also be a eukaryote, such as a mammalian, insect, plant, or fungal cell.

The host cell may be a fungal cell. "Fungi" as used herein includes the phyla Ascomycota, Basidiomycota, Chytridiomycota, and Zygomycota as well as the Oomycota and all mitosporic fungi (as defined by Hawksworth et al., *In, Ainsworth and Bisby's Dictionary of The Fungi*, 8th edition, 1995, CAB International, University Press, Cambridge, UK).

The fungal host cell may be a yeast cell. "Yeast" as used herein includes ascosporogenous yeast (Endomycetales), basidiosporogenous yeast, and yeast belonging to the Fungi Imperfecti (Blastomycetes). Since the classification of yeast may change in the future, for the purposes of this invention, yeast shall be defined as described in *Biology and Activities of Yeast* (Skinner, Passmore, and Davenport, editors, *Soc. App. Bacteriol. Symposium Series No. 9*, 1980).

The yeast host cell may be a *Candida, Hansenula, Kluyveromyces, Pichia, Saccharomyces, Schizosaccharomyces*, or *Yarrowia* cell such as a *Kluyveromyces lactis, Saccharomyces carlsbergensis, Saccharomyces cerevisiae, Saccharomyces diastaticus, Saccharomyces douglasii, Saccharomyces kluyveri, Saccharomyces norbensis, Saccharomyces oviformis*, or *Yarrowia lipolytica* cell.

The fungal host cell may be a filamentous fungal cell. "Filamentous fungi" include all filamentous forms of the subdivision Eumycota and Oomycota (as defined by Hawksworth et al., 1995, supra). The filamentous fungi are generally characterized by a mycelial wall composed of chitin, cellulose, glucan, chitosan, mannan, and other complex polysaccharides. Vegetative growth is by hyphal elongation and carbon catabolism is obligately aerobic. In contrast, vegetative growth by yeasts such as *Saccharomyces cerevisiae* is by budding of a unicellular thallus and carbon catabolism may be fermentative.

The filamentous fungal host cell may be an *Acremonium, Aspergillus, Aureobasidium, Bjerkandera, Ceriporiopsis, Chrysosporium, Coprinus, Coriolus, Cryptococcus, Filibasidium, Fusarium, Humicola, Magnaporthe, Mucor, Myceliophthora, Neocallimastix, Neurospora, Paecilomyces, Penicillium, Phanerochaete, Phiebia, Piromyces, Pleurotus, Schizophyllum, Talaromyces, Thermoascus, Thielavia, Tolypocladium, Trametes*, or *Trichoderma* cell.

For example, the filamentous fungal host cell may be an *Aspergillus awamori, Aspergillus foetidus, Aspergillus fumigatus, Aspergillus japonicus, Aspergillus nidulans, Aspergillus niger, Aspergillus oryzae, Bjerkandera adusta, Ceriporiopsis aneirina, Ceriporiopsis caregiea, Ceriporiopsis gilvescens, Ceriporiopsis pannocinta, Ceriporiopsis rivulosa, Ceriporiopsis subrufa, Ceriporiopsis subvermispora, Chrysosporium inops, Chrysosporium keratinophilum, Chrysosporium lucknowense, Chrysosporium merdarium, Chrysosporium pannicola, Chrysosporium queenslandicum, Chrysosporium tropicum, Chrysosporium zonatum, Coprinus cinereus, Coriolus hirsutus, Fusarium bactridioides, Fusarium cerealis, Fusarium crookwellense, Fusarium culmorum, Fusarium graminearum, Fusarium graminum, Fusarium heterosporum, Fusarium negundi, Fusarium oxysporum, Fusarium reticulatum, Fusarium roseum, Fusarium sambucinum, Fusarium sarcochroum, Fusarium sporotrichioides, Fusarium suiphureum, Fusarium torulosum, Fusarium trichothecioides, Fusarium venenatum, Humicola insolens, Humicola lanuginosa, Mucor miehei, Myceliophthora thermophila, Neurospora crassa, Penicillium purpurogenum, Phanerochaete chrysosporium, Phiebia radiata, Pleurotus eryngii, Thielavia terrestris, Trametes villosa, Trametes versicolor, Trichoderma harzianum, Trichoderma koningii, Trichoderma longibrachiatum, Trichoderma reesei*, or *Trichoderma viride* cell.

Fungal cells may be transformed by a process involving protoplast formation, transformation of the protoplasts, and regeneration of the cell wall in a manner known per se. Suitable procedures for transformation of *Aspergillus* and *Trichoderma* host cells are described in EP 238023, Yelton et al., 1984, *Proc. Natl. Acad. Sci. USA* 81: 1470-1474, and Christensen et al., 1988, *Bio/Technology* 6: 1419-1422. Suitable methods for transforming *Fusarium* species are described by Malardier et al., 1989, *Gene* 78: 147-156, and WO 96/00787. Yeast may be transformed using the procedures described by Becker and Guarente, In Abelson, J. N. and Simon, M. I., editors, *Guide to Yeast Genetics and Molecular Biology, Methods in Enzymology*, Volume 194, pp 182-187, Academic Press, Inc., New York; Ito et al., 1983, *J. Bacteriol.* 153: 163; and Hinnen et al., 1978, *Proc. Natl. Acad. Sci. USA* 75: 1920.

Methods of Production

The present invention also relates to methods of producing a variant, comprising: (a) cultivating a recombinant host cell of the present invention under conditions suitable for expression of the variant; and (b) recovering the variant.

The host cells are cultivated in a nutrient medium suitable for production of the variant using methods known in the art. For example, the cell may be cultivated by shake flask cultivation, or small-scale or large-scale fermentation (including continuous, batch, fed-batch, or solid state fermentations) in laboratory or industrial fermentors performed in a suitable medium and under conditions allowing the variant to be expressed and/or isolated. The cultivation takes place in a suitable nutrient medium comprising carbon and nitrogen sources and inorganic salts, using procedures known in the art. Suitable media are available from commercial suppliers or may be prepared according to published compositions (e.g., in catalogues of the American Type Culture Collection). If the variant is secreted into the nutrient medium, the variant can be recovered directly from the medium. If the variant is not secreted, it can be recovered from cell lysates.

The variant may be detected using methods known in the art that are specific for the variants. These detection methods include, but are not limited to, use of specific antibodies, formation of an enzyme product, or disappearance of an enzyme substrate. For example, an enzyme assay may be used to determine the activity of the variant.

The variant may be recovered using methods known in the art. For example, the variant may be recovered from the nutrient medium by conventional procedures including, but not limited to, collection, centrifugation, filtration, extraction, spray-drying, evaporation, or precipitation.

The variant may be purified by a variety of procedures known in the art including, but not limited to, chromatography (e.g., ion exchange, affinity, hydrophobic, chromatofocusing, and size exclusion), electrophoretic procedures (e.g., preparative isoelectric focusing), differential solubility (e.g., ammonium sulfate precipitation), SDS-PAGE, or extraction (see, e.g., *Protein Purification*, Janson and Ryden, editors, VCH Publishers, New York, 1989) to obtain substantially pure variants.

In an alternative aspect, the variant is not recovered, but rather a host cell of the present invention expressing the variant is used as a source of the variant.

Compositions

The present invention also relates to compositions comprising a polypeptide of the present invention. Preferably the composition also comprises a carrier and/or an excipient. More preferably, the compositions are enriched in such a polypeptide. The term "enriched" indicates that the glucoamylase activity of the composition has been increased, e.g., with an enrichment factor of at least 1.1. Preferably, the compositions are formulated to provide desirable characteristics such as low color, low odor and acceptable storage stability.

The composition may comprise a polypeptide of the present invention as the major enzymatic component, e.g., a mono-component composition. Alternatively, the composition may comprise multiple enzymatic activities, such as an aminopeptidase, amylase, carbohydrase, carboxypeptidase, catalase, cellulase, chitinase, cutinase, cyclodextrin glycosyltransferase, deoxyribonuclease, esterase, alpha-galactosidase, beta-galactosidase, glucoamylase, alpha-glucosidase, beta-glucosidase, haloperoxidase, invertase, laccase, lipase, mannosidase, oxidase, pectinolytic enzyme, peptidoglutaminase, peroxidase, phytase, polyphenoloxidase, proteolytic enzyme, ribonuclease, transglutaminase, or xylanase.

In a particular embodiment the composition comprises an alpha amylase and the polypeptide according to the invention.

In a more particular embodiment the composition further comprises a protease.

The additional enzyme(s) may be produced, for example, by a microorganism belonging to the genus *Aspergillus*, preferably *Aspergillus aculeatus, Aspergillus awamori, Aspergillus fumigatus, Aspergillus foetidus, Aspergillus japonicus, Aspergillus nidulans, Aspergillus niger*, or *Aspergillus oryzae; Fusarium*, preferably *Fusarium bactridioides, Fusarium cerealis, Fusarium crookwellense, Fusarium culmorum, Fusarium graminearum, Fusarium graminum, Fusarium heterosporum, Fusarium negundi, Fusarium oxysporum, Fusarium reticulatum, Fusarium roseum, Fusarium sambucinum, Fusarium sarcochroum, Fusarium suiphureum, Fusarium toruloseum, Fusarium trichothecioides*, or *Fusarium venenatum; Humicola*, preferably *Humicola insolens* or *Humicola lanuginosa*; or *Trichoderma*, preferably *Trichoderma harzianum, Trichoderma koningii, Trichoderma longibrachiatum, Trichoderma reesei*, or *Trichoderma viride*.

The polypeptide compositions may be prepared in accordance with methods known in the art and may be in the form of a liquid or a dry composition. For instance, the polypeptide composition may be in the form of a granulate or a microgranulate. The polypeptide to be included in the composition may be stabilized in accordance with methods known in the art.

Examples are given below of preferred uses of the polypeptide or polypeptide compositions of the invention. The dosage of the polypeptide composition of the invention and other conditions under which the composition is used may be determined on the basis of methods known in the art.

Combination of Glucoamylase and Alpha-Amylase

According to this aspect of the invention a glucoamylase of the invention may be combined with an alpha-amylase. Preferably, the ratio of acid alpha-amylase to glucoamylase is between 0.05 and 5.0 AFAU/AGU. More preferably the ratio between acid alpha-amylase activity and glucoamylase activity is at least 0.10, at least 0.15, at least 0.20, at least 0.25, at least 0.30, at least 0.35, at least 0.40, at least 0.45, at least 0.50, at least 0.55, at least 0.60, at least 0.65, at least 0.70, at least 0.75, at least 0.80, at least 0.85, at least 0.90, at least 0.95, at least 1.00, at least 1.05, at least 1.10, at least 1.20, at least 1.30, at least 1.40, at least 1.50, at least 1.60, at least 1.70, at least 1.80, at least 1.85, or even at least 1.90 AFAU/AGU. However, the ratio between acid alpha-amylase activity and glucoamylase activity should preferably be less than 4.50, less than 4.00, less than 3.50, less than 3.00, less than 2.50, or even less than 2.25 AFAU/AGU.

Above composition is suitable for use in liquefaction, saccharification, and/or fermentation process, preferably in starch conversion, especially for producing syrup and fermentation products, such as ethanol.

Examples are given below of preferred uses of the polypeptide compositions of the present invention. The dosage of the polypeptide composition of the invention and other conditions under which the composition is used may be determined on the basis of methods known in the art.

Uses

The present invention is also directed to use of a polypeptide of the present invention in a liquefaction, a saccharification and/or a fermentation process. The polypeptide may be used in a single process, for example, in a liquefaction process, a saccharification process, or a fermentation process. The polypeptide may also be used in a combination of processes for example in a liquefaction and saccharification process, in a liquefaction and fermentation process, or in a saccharification and fermentation process, preferably in relation to starch conversion.

In a preferred aspect of the present invention, the liquefaction, saccharification and/or fermentation process includes sequentially or simultaneously performed liquefaction and saccharification processes.

In conventional enzymatic liquefaction process, thermostable alpha-amylase is added and the long chained starch is degraded into branched and linear shorter units (maltodextrins), but glucoamylase is not added. The glucoamylase of the present invention is highly thermostable, so it is advantageous to add the glucoamylase in the liquefaction process. The glucoamylase of the present invention has a synergistic effect when combined with an alpha-amylase in the liquefaction process. During conventional saccharification, the dextrins generated during the liquefaction process are further hydrolyzed to produce low molecular sugars DP1-3 that can be metabolized by fermenting organism. The hydrolysis is typically accomplished using glucoamylases; alternatively in addition to glucoamylases, alpha-glucosidases and/or acid alpha-amylases can be used.

When applying the glucoamylase of the present invention, potentially in combination with an alpha-amylase in a liquefaction and/or saccharification process, especially in a simultaneous liquefaction and saccharification process, the process can be conducted at a higher temperature. By conducting the liquefaction and/or saccharification process at higher temperatures the process can be carried out in a shorter period of time or alternatively the process can be carried out using lower enzyme dosage. Furthermore, the risk of microbial contamination is reduced when carrying the liquefaction and/or saccharification process at higher temperature.

Conversion of Starch-Containing Material

The present invention provides a use of the glucoamylase of the invention for producing glucoses and the like from starch. Generally, the method includes the steps of partially hydrolyzing precursor starch using glucoamylase of the present invention either alone or in the presence of an alpha-amylase.

The glucoamylase of the invention may also be used in combination with an enzyme that hydrolyzes only alpha-(1, 6)-glucosidic bonds in molecules comprising at least four glucosyl residues.

In a further aspect the invention relates to the use of a glucoamylase of the invention in starch conversion. Furthermore, the glucoamylase of the invention may be used in a continuous starch conversion process including a continuous saccharification process.

Production of Syrup, Beverage and/or Fermentation Product

Uses of the glucoamylase of the invention include conversion of starch to e.g., syrup beverage, and/or a fermentation product, including ethanol.

The present invention also provides a process of using a glucoamylase of the invention for producing syrup, such as glucose and the like, from starch-containing material. Suitable starting materials are exemplified in the "Starch-containing materials"-section. Generally, the process comprises the steps of partially or totally hydrolyzing starch-containing material (liquefaction and/or saccharification) in the presence of the glucoamylase of the present invention alone or in combination with alpha-amylase to release glucose from the non-reducing ends of the starch or related oligo- and poly-saccharide molecules.

The glucoamylase of the invention may also be used in immobilized form. This is suitable and often used for producing specialty syrups, such as maltose syrups as well as in the raffinate stream of oligosaccharides in connection with the production of fructose syrups, e.g., high fructose syrup (HFS).

The glucoamylase of the present invention can also be used for producing various beverages, such as, but not limited to, the beverage of tomato, potato, Chinese potato, sweet potato, and/or pumpkin.

Fermentation Products

The term "fermentation product" means a product produced by a process including a fermentation process using a fermenting organism. Fermentation products contemplated according to the invention include alcohols (e.g., arabinitol, butanol, ethanol, glycerol, methanol, ethylene glycol, 1,3-propanediol [propylene glycol], butanediol, glycerin, sorbitol, and xylitol); organic acids (e.g., acetic acid, acetonic acid, adipic acid, ascorbic acid, citric acid, 2,5-diketo-D-gluconic acid, formic acid, fumaric acid, glucaric acid, gluconic acid, glucuronic acid, glutaric acid, 3-hydroxypropionic acid, itaconic acid, lactic acid, malic acid, malonic acid, oxalic acid, oxaloacetic acid, propionic acid, succinic acid, and xylonic acid); ketones (e.g., acetone); amino acids (e.g., aspartic acid, glutamic acid, glycine, lysine, serine, and threonine); an alkane (e.g., pentane, hexane, heptane, octane, nonane, decane, undecane, and dodecane); a cycloalkane (e.g., cyclopentane, cyclohexane, cycloheptane, and cyclooctane); an alkene (e.g. pentene, hexene, heptene, and octene); gases (e.g., methane, hydrogen ($H_2$), carbon dioxide ($CO_2$), and carbon monoxide (CO)); antibiotics (e.g., penicillin and tetracycline); enzymes; vitamins (e.g., riboflavin, $B_{12}$, beta-carotene); and hormones. In a preferred aspect the fermentation product is ethanol, e.g., fuel ethanol; drinking ethanol, i.e., potable neutral spirits; or industrial ethanol or products used in the consumable alcohol industry (e.g., beer and wine), dairy industry (e.g., fermented dairy products), leather industry and tobacco industry. Preferred beer types comprise ales, stouts, porters, lagers, bitters, malt liquors, happoushu, high-alcohol beer, low-alcohol beer, low-calorie beer or light beer. Preferred fermentation processes used include alcohol fermentation processes, which are well known in the art. Preferred fermentation processes are anaerobic fermentation processes, which are well known in the art.

Brewing

The glucoamylases of the present invention are highly thermostable and therefore they can be used in an industry which needs starch hydrolysis at high temperature. For example, glucoamylases of the invention can be used in a brewing industry. The glucoamylases of the invention is added in effective amounts which can be easily determined by the skilled person in the art.

Production of a Liquefaction, Saccharification and/or Fermentation Product

In this aspect the present invention relates to a process for producing a liquefaction, saccharification and/or fermentation product from starch-containing material, comprising the step of: treating starch-containing material with a polypeptide of the present invention.

Suitable starch-containing starting materials are listed in the "Starch-containing materials"-section below. Contemplated enzymes are listed in the "Enzymes"—section below. Preferably the process of present invention comprises treating starch-containing material with a polypeptide of the present invention alone or together with an alpha-amylase. The liquefaction and/or saccharification product of the present invention are dextrin, or low molecular sugars, for example DP1-3. In the liquefaction process the conversion of starch into glucose, dextrin and/or low molecular weight sugars is enhanced by the addition of a glucoamylase of the present invention. The fermentation product, such as ethanol, may optionally be recovered after fermentation, e.g., by distillation. The fermentation is preferably carried out in the presence of yeast, preferably a strain of *Saccharomyces*. Suitable fermenting organisms are listed in the "Fermenting Organisms"-section below.

Process for Producing Fermentation Products from Gelatinized Starch Containing Material In this aspect the present invention relates to a process for producing a fermentation product, especially ethanol, from starch-containing material, which process includes a liquefaction step and sequentially or simultaneously performed saccharification and fermentation steps.

The invention relates to a process for producing a fermentation product from starch-containing material comprising the steps of:

(a) liquefying starch-containing material; using an alpha amylase;

(b) saccharifying the liquefied material obtained in step (a) using a glucoamylase; and (c) fermenting the saccharified material using a fermenting organism.

Preferably step (a) includes also using the glucoamylase of the invention. In one embodiment the glucoamylase of the invention is also present/added in step (b).

The fermentation product, such as especially ethanol, may optionally be recovered after fermentation, e.g., by distillation. Suitable starch-containing starting materials are listed in the section "Starch-containing materials"-section below. Contemplated enzymes are listed in the "Enzymes"-section below. The liquefaction is preferably carried out in the presence of an alpha-amylase. The fermentation is preferably carried out in the presence of yeast, preferably a strain of *Saccharomyces*. Suitable fermenting organisms are listed in the "Fermenting Organisms"-section below. In preferred embodiments step (b) and (c) are carried out sequentially or simultaneously (i.e., as SSF process).

In a particular embodiment, the process of the invention further comprises, prior to the step (a), the steps of:

x) reducing the particle size of the starch-containing material, preferably by milling; and y) forming a slurry comprising the starch-containing material and water.

The aqueous slurry may contain from 10-40 wt. %, preferably 25-35 wt. % starch-containing material. The slurry is heated to above the gelatinization temperature and alpha-amylase, preferably bacterial and/or acid fungal alpha-amylase, may be added to initiate liquefaction (thinning). The slurry may in an embodiment be jet-cooked to further gelatinize the slurry before being subjected to an alpha-amylase in step (a) of the invention.

More specifically liquefaction may be carried out as a three-step hot slurry process. The slurry is heated to between 60-95° C., preferably 80-85° C., and alpha-amylase is added to initiate liquefaction (thinning). Then the slurry may be jet-cooked at a temperature between 95-140° C., preferably 105-125° C., for 1-15 minutes, preferably for 3-10 minute, especially around 5 minutes. The slurry is cooled to 60-95° C. and more alpha-amylase is added to finalize hydrolysis (secondary liquefaction). The liquefaction process is usually carried out at pH 4.5-6.5, in particular at a pH between 5 and 6. Milled and liquefied whole grains are known as mash.

The saccharification in step (b) may be carried out using conditions well know in the art. For instance, a full saccharification process may last up to from about 24 to about 72 hours, however, it is common only to do a pre-saccharification of typically 40-90 minutes at a temperature between 30-65° C., typically about 60° C., followed by complete saccharification during fermentation in a simultaneous saccharification and fermentation process (SSF process). Saccharification is typically carried out at temperatures from 30-65° C., typically around 60° C., and at a pH between 4 and 5, normally at about pH 4.5.

The most widely used process in fermentation product, especially ethanol, production is the simultaneous saccharification and fermentation (SSF) process, in which there is no holding stage for the saccharification, meaning that fermenting organism, such as yeast, and enzyme(s) may be added together. SSF may typically be carried out at a temperature between 25° C. and 40° C., such as between 29° C. and 35° C., such as between 30° C. and 34° C., such as around 32° C. According to the invention the temperature may be adjusted up or down during fermentation.

In accordance with the present invention the fermentation step (c) includes, without limitation, fermentation processes used to produce alcohols (e.g., ethanol, methanol, butanol); organic acids (e.g., citric acid, acetic acid, itaconic acid, lactic acid, gluconic acid); ketones (e.g., acetone); amino acids (e.g., glutamic acid); gases (e.g., $H_2$ and $CO_2$); antibiotics (e.g., penicillin and tetracycline); enzymes; vitamins (e.g., riboflavin, $B_{12}$, beta-carotene); and hormones. Preferred fermentation processes include alcohol fermentation processes, as are well known in the art. Preferred fermentation processes are anaerobic fermentation processes, as are well known in the art.

Processes for Producing Fermentation Products from Un-Gelatinized Starch-Containing In this aspect the invention relates to processes for producing a fermentation product from starch-containing material without gelatinization of the starch-containing material (i.e., uncooked starch-containing material). According to the invention the desired fermentation product, such as ethanol, can be produced without liquefying the aqueous slurry containing the starch-containing material. In one embodiment a process of the invention includes saccharifying (milled) starch-containing material, e.g., granular starch, below the gelatinization temperature in the presence of an alpha amylase to produce sugars that can be fermented into the desired fermentation product by a suitable fermenting organism. In another embodiment a glucoamylase of the invention and an alpha amylase are used during saccharification and fermentation. In one aspect the invention relates to a process for producing a fermentation product from starch-containing material comprising:

(a) saccharifying starch-containing material with a mature glucoamylase according to the invention, preferably having the sequence shown as amino acids 22 to 616 in SEQ ID NO: 2, at a temperature below the initial gelatinization temperature of said starch-containing material, (b) fermenting using a fermenting organism.

Steps (a) and (b) of the process of the invention may be carried out sequentially or simultaneously. In an embodiment, a slurry comprising water and starch-containing material, is prepared before step (a).

In a preferred embodiment step (a) includes addition of an alpha amylase.

The fermentation process may be carried out for a period of 1 to 250 hours, preferably is from 25 to 190 hours, more preferably from 30 to 180 hours, more preferably from 40 to 170 hours, even more preferably from 50 to 160 hours, yet more preferably from 60 to 150 hours, even yet more preferably from 70 to 140 hours, and most preferably from 80 to 130 hours.

The term "initial gelatinization temperature" means the lowest temperature at which gelatinization of the starch commences. Starch heated in water begins to gelatinize between 50° C. and 75° C.; the exact temperature of gelatinization depends on the specific starch, and can readily be determined by the skilled artisan. Thus, the initial gelatinization temperature may vary according to the plant species, to the particular variety of the plant species as well as with the growth conditions. In the context of this invention the initial gelatinization temperature of a given starch-containing material is the temperature at which birefringence is lost in 5% of the starch granules using the method described by Gorinstein and Lii, 1992, *Starch/Stärke* 44(12): 461-466.

Before step (a) a slurry of starch-containing material, such as granular starch, having 10-55 wt. % dry solids, preferably 25-40 wt. % dry solids, more preferably 30-35 wt. % dry solids of starch-containing material may be prepared. The slurry may include water and/or process waters, such as stillage (backset), scrubber water, evaporator condensate or distillate, side stripper water from distillation, or other fermentation product plant process water. Because the process of the invention is carried out below the gelatinization temperature and thus no significant viscosity increase takes place, high levels of stillage may be used if desired. In an embodiment the aqueous slurry contains from about 1 to about 70 vol. % stillage, preferably 15-60% vol. % stillage, especially from about 30 to 50 vol. % stillage.

The starch-containing material may be prepared by reducing the particle size, preferably by dry or wet milling, to 0.05 to 3.0 mm, preferably 0.1-0.5 mm. After being subjected to a process of the invention at least 85%, at least 86%, at least 87%, at least 88%, at least 89%, at least 90%, at least 91%, at least 92%, at least 93%, at least 94%, at least 95%, at least 96%, at least 97%, at least 98%, or preferably at least 99% of the dry solids of the starch-containing material is converted into a soluble starch hydrolysate.

The process of the invention is conducted at a temperature below the initial gelatinization temperature. Preferably the temperature at which step (a) is carried out is between 30-75° C., preferably between 45-60° C.

In a preferred embodiment step (a) and step (b) are carried out as a sequential or simultaneous saccharification and fermentation process. In such preferred embodiment the process is typically carried at a temperature between 25° C. and 40° C., such as between 29° C. and 35° C., such as between 30° C. and 34° C., such as around 32° C. According to the invention the temperature may be adjusted up or down during fermentation.

In an embodiment simultaneous saccharification and fermentation is carried out so that the sugar level, such as glucose level, is kept at a low level such as below 6 wt. %, preferably below about 3 wt. %, preferably below about 2 wt. %, more preferred below about 1 wt. %, even more preferred below about 0.5 wt. %, or even more preferred 0.25 wt. %, such as below about 0.1 wt. %. Such low levels of sugar can be accomplished by simply employing adjusted quantities of enzyme and fermenting organism. A skilled person in the art can easily determine which quantities of enzyme and fermenting organism to use. The employed quantities of enzyme and fermenting organism may also be selected to maintain low concentrations of maltose in the fermentation broth. For instance, the maltose level may be kept below about 0.5 wt. % or below about 0.2 wt. %.

The process may be carried out at a pH in the range between 3 and 7, preferably from pH 3.5 to 6, or more preferably from pH 4 to 5.

The glucoamylase of the present invention is highly thermostable, so the pre-saccharification and/or saccharification of the present invention can be carried at a higher temperature than the conventional pre-saccharification and/or saccharification. In one embodiment a process of the invention includes pre-saccharifying starch-containing material before simultaneous saccharification and fermentation (SSF) process. The pre-saccharification can be carried out at a high temperature (for example, 50-85° C., preferably 60-75° C.) before moving into SSF.

Starch-Containing Materials

Any suitable starch-containing starting material, including granular starch, may be used according to the present invention. The starting material is generally selected based on the desired fermentation product. Examples of starch-containing starting materials, suitable for use in a process of present invention, include tubers, roots, stems, whole grains, corns, cobs, wheat, barley, rye, milo, sago, cassava, tapioca, sorghum, rice peas, beans, or sweet potatoes, or mixtures thereof, or cereals, sugar-containing raw materials, such as molasses, fruit materials, sugar cane or sugar beet, potatoes, and cellulose-containing materials, such as wood or plant residues, or mixtures thereof. Contemplated are both waxy and non-waxy types of corn and barley.

Fermenting Organisms

"Fermenting organism" refers to any organism, including bacterial and fungal organisms, suitable for use in a fermentation process and capable of producing desired a fermentation product. Especially suitable fermenting organisms are able to ferment, i.e., convert, sugars, such as glucose or maltose, directly or indirectly into the desired fermentation product. Examples of fermenting organisms include fungal organisms, such as yeast. Preferred yeast includes strains of *Saccharomyces* spp., in particular, *Saccharomyces cerevisiae*. Commercially available yeast include, e.g., Red Star™/Lesaffre Ethanol Red (available from Red Star/Lesaffre, USA) FALI (available from Fleischmann's Yeast, a division of Burns Philp Food Inc., USA), SUPERSTART (available from Alltech), GERT STRAND (available from Gert Strand AB, Sweden) and FERMIOL (available from DSM Specialties).

Enzymes

Glucoamylase

The glucoamylase is preferably a glucoamylase of the invention. However, as mentioned above a glucoamylase of the invention may also be combined with other glucoamylases.

The glucoamylase may added in an amount of 0.001 to 10 AGU/g DS, preferably from 0.01 to 5 AGU/g DS, such as around 0.05, 0.1, 0.3, 0.5, 1 or 2 AGU/g DS, especially 0.05 to 0.5 AGU/g DS; or 0.02-20 AGU/g DS, preferably 0.1-10 AGU/g DS.

Alpha-Amylase

The alpha-amylase may according to the invention be of any origin. Preferred are alpha-amylases of fungal or bacterial origin.

In a preferred aspect the alpha-amylase is an acid alpha-amylase, e.g., fungal acid alpha-amylase or bacterial acid alpha-amylase. The term "acid alpha-amylase" means an alpha-amylase (E.C. 3.2.1.1) which added in an effective amount has activity optimum at a pH in the range of 3 to 7, preferably from 3.5 to 6, or more preferably from 4-5.

Bacterial Alpha-Amylases

According to the invention a bacterial alpha-amylase may preferably be derived from the genus *Bacillus*.

In a preferred aspect the *Bacillus* alpha-amylase is derived from a strain of *B. licheniformis, B. amyloliquefaciens, B. subtilis* or *B. stearothermophilus*, but may also be derived from other *Bacillus* sp. Specific examples of contemplated alpha-amylases include the *Bacillus licheniformis* alpha-amylase (BLA) shown in SEQ ID NO: 4 in WO 99/19467, the *Bacillus amyloliquefaciens* alpha-amylase (BAN) shown in SEQ ID NO: 5 in WO 99/19467, and the *Bacillus stearothermophilus* alpha-amylase (BSG) shown in SEQ ID NO: 3 in WO 99/19467. In an embodiment of the invention the alpha-amylase is an enzyme having a degree of identity of at least 60%, preferably at least 70%, more preferred at least 80%, even more preferred at least 90%, such as at least 95%, at least 96%, at least 97%, at least 98% or at least 99% identity to any of the sequences shown as SEQ ID NOS: 1, 2, 3, 4, or 5, respectively, in WO 99/19467.

The *Bacillus* alpha-amylase may also be a variant and/or hybrid, especially one described in any of WO 96/23873, WO 96/23874, WO 97/41213, WO 99/19467, WO 00/60059, and WO 02/10355 (all documents hereby incorporated by reference). Specifically contemplated alpha-amylase variants are disclosed in U.S. Pat. Nos. 6,093,562, 6,297,038 or U.S. Pat. No. 6,187,576 (hereby incorporated by reference) and include *Bacillus stearothermophilus* alpha-amylase (BSG alpha-amylase) variants having a deletion of one or two amino acid in position 179 to 182, preferably a double deletion disclosed in WO 1996/023873—see e.g., page 20, lines 1-10 (hereby incorporated by reference), preferably corresponding to delta (181-182) compared to the wild-type BSG alpha-amylase amino acid sequence set forth in SEQ ID NO: 3 disclosed in WO 99/19467 or deletion of amino acids 179 and 180 using SEQ ID NO: 3 in WO 99/19467 for numbering (which reference is hereby incorporated by reference). Even more preferred are *Bacillus* alpha-amylases, especially *Bacillus stearothermophilus* alpha-amylase, which have a double deletion corresponding to delta (181-182) and further comprise a N193F substitution (also denoted 1181*+G182*+N193F) compared to the wild-type BSG alpha-amylase amino acid sequence set forth in SEQ ID NO: 3 disclosed in WO 99/19467.

The alpha-amylase may also be a maltogenic alpha-amylase. A "maltogenic alpha-amylase" (glucan 1,4-alpha-maltohydrolase, E.C. 3.2.1.133) is able to hydrolyze amylose and amylopectin to maltose in the alpha-configuration. A maltogenic alpha-amylase from *Bacillus stearothermophilus* strain NCIB 11837 is commercially available from Novozymes A/S, Denmark. The maltogenic alpha-amylase is described in U.S. Pat. Nos. 4,598,048, 4,604,355 and 6,162,628, which are hereby incorporated by reference.

Bacterial Hybrid Alpha-Amylases

A hybrid alpha-amylase specifically contemplated comprises 445 C-terminal amino acid residues of the *Bacillus licheniformis* alpha-amylase (shown as SEQ ID NO: 4 in WO 99/19467) and the 37 N-terminal amino acid residues of the alpha-amylase derived from *Bacillus amyloliquefaciens* (shown as SEQ ID NO: 3 in WO 99/194676), with one or more, especially all, of the following substitutions: G48A+T49I+G107A+H156Y+A181T+N190F+I201F+A209V+Q264S (using the *Bacillus licheniformis* numbering). Also preferred are variants having one or more of the following mutations (or corresponding mutations in other *Bacillus* alpha-amylase backbones): H154Y, A181T, N190F, A209V and Q264S and/or deletion of two residues between positions 176 and 179, preferably deletion of E178 and G179 (using the SEQ ID NO: 5 numbering of WO 99/19467).

Fungal Alpha-Amylases

Fungal acid alpha-amylases include acid alpha-amylases derived from a strain of the genus *Aspergillus*, such as *Aspergillus oryzae*, *Aspergillus niger*, or *Aspergillus kawachii* alpha-amylases.

A preferred acid fungal alpha-amylase is a Fungamyl-like alpha-amylase which is preferably derived from a strain of *Aspergillus oryzae*. In the present disclosure, the term "Fungamyl-like alpha-amylase" indicates an alpha-amylase which exhibits a high identity, i.e. more than 70%, more than 75%, more than 80%, more than 85% more than 90%, more than 95%, more than 96%, more than 97%, more than 98%, more than 99% or even 100% identity to the mature part of the amino acid sequence shown in SEQ ID NO: 10 in WO 96/23874.

Another preferred acid alpha-amylase is derived from a strain *Aspergillus niger*. In a preferred aspect the acid fungal alpha-amylase is the one from *A. niger* disclosed as "AMYA_ASPNG" in the Swiss-prot/TeEMBL database under the primary accession no. P56271 and described in more detail in WO 89/01969 (Example 3). The acid *Aspergillus niger* acid alpha-amylase is also shown as SEQ ID NO: 1 in WO 2004/080923 (Novozymes) which is hereby incorporated by reference. Also variants of said acid fungal amylase having at least 70% identity, such as at least 80% or even at least 90% identity, such as at least 95%, at least 96%, at least 97%, at least 98%, or at least 99% identity to SEQ ID NO: 1 in WO 2004/080923 are contemplated.

In a preferred aspect the alpha-amylase is derived from *Aspergillus kawachii* and disclosed by Kaneko et al. J. Ferment. Bioeng. 81:292-298 (1996) "Molecular-cloning and determination of the nucleotide-sequence of a gene encoding an acid-stable alpha-amylase from *Aspergillus kawachii*"; and further as EMBL: #AB008370.

The fungal acid alpha-amylase may also be a wild-type enzyme comprising a carbohydrate-binding module (CBM) and an alpha-amylase catalytic domain (i.e., a none-hybrid), or a variant thereof. In an embodiment the wild-type acid alpha-amylase is derived from a strain of *Aspergillus kawachii*.

An acid alpha-amylases may according to the invention be added in an amount of 0.01 to 10 AFAU/g DS, preferably 0.01 to 5 AFAU/g DS, especially 0.02 to 2 AFAU/g DS.

Fungal Hybrid Alpha-Amylases

In a preferred aspect the fungal acid alpha-amylase is a hybrid alpha-amylase. Preferred examples of fungal hybrid alpha-amylases include the ones disclosed in WO 2005/003311 or U.S. Patent Publication no. 2005/0054071 (Novozymes) or US patent application No. 2006/0148054 (Novozymes) which is hereby incorporated by reference. A hybrid alpha-amylase may comprise an alpha-amylase catalytic domain (CD) and a carbohydrate-binding domain/module (CBM) and optional a linker.

Specific examples of contemplated hybrid alpha-amylases include, but not limited to those disclosed in U.S. patent application No. 2006/0148054 including Fungamyl variant with catalytic domain JA118 and *Athelia rolfsii* SBD (SEQ ID NO: 100 in U.S. application No. 2006/0148054), *Rhizomucor pusillus* alpha-amylase with *Athelia rolfsii* AMG linker and SBD (SEQ ID NO: 101 in U.S. application No. 2006/0148054) and *Meripilus giganteus* alpha-amylase with *Athelia rolfsii* glucoamylase linker and SBD (SEQ ID NO: 102 in U.S. application No. 2006/0148054); and *Rhizomucor pusillus* alpha-amylase with *Aspergillus niger* glucoamylase linker and CBM (SEQ ID NO 2 in international publication No. WO2007/144424).

Other specific examples of contemplated hybrid alpha-amylases include, but not limited to those disclosed in U.S. Patent Publication no. 2005/0054071, including those disclosed in Table 3 on page 15, such as *Aspergillus niger* alpha-amylase with *Aspergillus kawachii* linker and starch binding domain.

Commercial Alpha-Amylase Products

Preferred commercial compositions comprising alpha-amylase include MYCOLASE from DSM (Gist Brocades), BAN™, TERMAMYL™ SC, FUNGAMYL™, LIQUOZYME™ SC, LIQUOZYME™ SC DS, and SAN™

SUPER, SAN™ EXTRA L (Novozymes A/S) and CLARASE™ L-40,000, DEX-LO™, SPEZYME™ FRED, SPEZYME™ AA, SPEZYME™ Ethyl, and SPEZYME™ DELTA AA (Genencor Int.)

The present invention is further described by the following examples that should not be construed as limiting the scope of the invention.

EXAMPLES

Materials and Methods

Glucoamylase Activity

Glucoamylase activity may be measured in AGU Units.
Glucoamylase Activity (AGU)

The Glucoamylase Unit (AGU) is defined as the amount of enzyme, which hydrolyzes 1 micromole maltose per minute under the standard conditions (37° C., pH 4.3, substrate: maltose 100 mM, buffer: acetate 0.1 M, reaction time 6 minutes as set out in the glucoamylase incubation below), thereby generating glucose.

| glucoamylase incubation: | |
|---|---|
| Substrate: | maltose 100 mM |
| Buffer: | acetate 0.1M |
| pH: | 4.30 ± 0.05 |
| Incubation temperature: | 37° C. ± 1 |
| Reaction time: | 6 minutes |
| Enzyme working range: | 0.5-4.0 AGU/mL |

The analysis principle is described by 3 reaction steps:
Step 1 is an enzyme reaction:

Glucoamylase (AMG), EC 3.2.1.3 (exo-alpha-1,4-glucan-glucohydrolase), hydrolyzes maltose to form alpha-D-glucose. After incubation, the reaction is stopped with NaOH.

Steps 2 and 3 result in an endpoint reaction:

Glucose is phosphorylated by ATP, in a reaction catalyzed by hexokinase. The glucose-6-phosphate formed is oxidized to 6-phosphogluconate by glucose-6-phosphate dehydrogenase. In this same reaction, an equimolar amount of NAD+ is reduced to NADH with a resulting increase in absorbance at 340 nm. An autoanalyzer system such as Konelab 30 Analyzer (Thermo Fisher Scientific) may be used.

| Colour reaction | |
|---|---|
| Tris | approx. 35 mM |
| ATP | 0.7 mM |
| NAD+ | 0.7 mM |
| $Mg^{2+}$ | 1.8 mM |
| Hexokinase | >850 U/L |
| Glucose-6-P-DH | >850 U/L |
| pH | approx. 7.8 |
| Temperature | 37.0° C. ± 1.0° C. |
| Reaction time | 420 sec |
| Wavelength | 340 nm |

Acid Alpha-Amylase Activity

When used according to the present invention the activity of any acid alpha-amylase may be measured in AFAU (Acid Fungal Alpha-amylase Units). Alternatively activity of acid alpha-amylase may be measured in KNU-s (Kilo Novozymes Units (Termamyl SC)).
Acid Alpha-Amylase Activity (AFAU)

Acid alpha-amylase activity may be measured in AFAU (Acid Fungal Alpha-amylase Units). 1 AFAU is defined as the amount of enzyme which degrades 5.260 mg starch dry matter per hour under the below mentioned standard conditions.

Acid alpha-amylase, an endo-alpha-amylase (1,4-alpha-D-glucan-glucanohydrolase, E.C. 3.2.1.1) hydrolyzes alpha-1,4-glucosidic bonds in the inner regions of the starch molecule to form dextrins and oligosaccharides with different chain lengths. The intensity of color formed with iodine is directly proportional to the concentration of starch. Amylase activity is determined using reverse colorimetry as a reduction in the concentration of starch under the specified analytical conditions.

$$STARCH + IODINE \xrightarrow[40°, pH\,2,5]{ALPHA-AMYLASE} DEXTRINS + OLIGOSACCHARIDES$$

$\lambda = 590$ nm blue/violet $\quad t = 23$ sec. $\quad$ color less

Standard Conditions/Reaction Conditions:
Substrate: Soluble starch, approx. 0.17 g/L
Buffer: Citrate, approx. 0.03 M
Iodine ($I_2$): 0.03 g/L
$CaCl_2$: 1.85 mM
pH: 2.50±0.05
Incubation temperature: 40° C.
Reaction time: 23 seconds
Wavelength: 590 nm
Enzyme concentration: 0.025 AFAU/mL
Enzyme working range: 0.01-0.04 AFAU/mL
DNA Manipulations Unless otherwise stated, DNA manipulations and transformations were performed using standard methods of molecular biology as described in Sambrook et al. (1989) Molecular cloning: A laboratory manual, Cold Spring Harbor lab. Cold Spring Harbor, N.Y.; Ausubel, F. M. et al. (eds.) "Current protocols in Molecular Biology", John Wiley and Sons, 1995; Harwood, C. R. and Cutting, S. M. (eds.).
DNA Sequencing

*E. coli* transformation for DNA sequencing was carried out by electroporation (BIO-RAD Gene Pulser) or chemically. DNA Plasmids were prepared by alkaline method (Molecular Cloning, Cold Spring Harbor) or with the Qiagen® Plasmid Kit. DNA fragments were recovered from agarose gel by the Qiagen gel extraction Kit. PCR was performed using a PTC-200 DNA Engine. The ABI PRISM™ 310 Genetic Analyzer was used for determination of all DNA sequences.
Media YP-2% Maltose was composed of 10 g/L yeast extract, 20 g/L pepton and 20 g/L maltose.

MLC medium was composed of 40 g/L Glucose, 50 g/L Soybean powder, 4 g/L Citric acid, pH 5.0.

M410 medium was composed of 50 g/L maltose-$1H_2O$, 8 g/L Yeast extract, 2 g/L $MgSO_4.7H_2O$, 4 g/L Citric acid-$1H_2O$, 50 g/L glucose, 2 g/L $K_2HPO_4$, 0.5 ml/L AMG trace metal solution, and 2 g/L urea, pH4.5. AMG trace metal solution was composed of 13.9 g/L $FeSO_4.7H_2O$, 13.5 g/L $MnSO_4.1H_2O$, 6.8 g/L $ZnCl_2$, 2.5 g/L $CuSO_4.5H_2O$, 0.24 g/L $NiCl_2.6H_2O$, and 3 g/L citric acid.

Unless otherwise stated, media are prepared according to Sambrook et al. (1989) *Molecular cloning: A laboratory manual*, Cold Spring Harbor lab., Cold Spring Harbor, N.Y. Chemicals used as buffers and substrates were commercial products of at least reagent grade.

FT X-14 medium was composed as shown below.

| Magnesiumsulfat | MgSO$_4$, 7H$_2$O | 0.3 g |
|---|---|---|
| Kaliumsulfat | K$_2$SO$_4$ | 0.3 g |
| Natriumchlorid | NaCl | 1 g |
| Kaliumdihydrogenphosphat | KH$_2$PO$_4$ | 1 g |
| Maltose | C$_{12}$H$_{22}$O$_{11}$•H$_2$O | 10 g |
| Yeast Extract | | 1.4 g |
| Dimethylmalonic acid | C$_5$H$_8$O$_4$ | 10 g |
| Trace metals MSA-SUB-FS-0044 | | 0.25 ml |
| Water ad | | 1000 ml |

Enzymes

Glucoamylases:

*Penicillium oxalicum* glycoamylase as disclosed in SEQ ID NO: 2 of WO2011/127802.

*Talaromyces emersonii* glucoamylase (which is disclosed in international publication WO 99/28448 as SEQ ID NO: 7)

*Aspergillus niger* glucoamylase (uniprot:P69328) (which is disclosed in Svensson, B. Larsen, K. Gunnarsson, A.; "Characterization of a glucoamylase G2 from *Aspergillus niger*."; Eur. J. Biochem. 154:497-502 (1986))

*Trametes cingulata* glucoamylase as disclosed in SEQ ID NO: 2 in WO 2006/069289 and available from Novozymes A/S.

Alpha-Amylases:

Acid alpha-amylase disclosed as Variant JA001 in international publication WO 2005/003311

Alpha-amylase produced from *Bacillus licheniformis*, e.g Termamyl™ SC (commercially available alpha-amylase from Novozymes A/S, Bagsvaerd, Denmark)

Hybrid alpha-amylase consisting of *Rhizomucor pusillus* alpha-amylase with *Aspergillus niger* glucoamylase linker and SBD disclosed as V039 in Table 5 in WO 2006/069290 (Novozymes A/S)

Alpha-Amylase A: *Bacillus stearothermophilus* alpha-amylase (SEQ ID NO: 3 in EP1023439B1) with the mutations I181*+G182*+N193F truncated to 491 amino acids shown as SEQ ID NO: 6 in WO2011/082425.

Alpha amylase 1407: *Bacillus stearothermophilus* alpha-amylase (SEQ ID NO: 3 in EP1023439B1) with the mutations I181*+G182*+N193F+V59A+Q89R+E129V+K177L+R179E+H208Y+K220P+N224L+Q254S truncated to 491 amino acids (see also WO2011/082425).

Proteases:

Protease 196: Metallo protease derived from *Thermoascus aurantiacus* CGMCC No. 0670 disclosed as amino acids 1-177 in SEQ ID NO: 2 in WO 2003/048353 with the following mutations: A27K+D79L+Y82F+S87G+D104P+A112P+A126V+D142L (see also WO2011/072191).

Example 1: Cloning of *Penicillium oxalicum* Strain Glucoamylase Gene

Preparation of *Penicillium oxalicum* Strain cDNA.

The cDNA was synthesized by following the instruction of 3' Rapid Amplification of cDNA End System (Invitrogen Corp., Carlsbad, Calif., USA).

Cloning of *Penicillium oxalicum* Strain Glucoamylase Gene.

The *Penicillium oxalicum* glucoamylase gene was cloned using the oligonucleotide primer shown below designed to amplify the glucoamylase gene from 5' end.

```
Sense primer:
                             (SEQ ID NO: 4)
5'-ATGCGTCTCACTCTATTATCAGGTG-3'
```

The full length gene was amplified by PCR with Sense primer and AUAP (supplied by 3' Rapid Amplifiction of cDNA End System) by using Platinum HIFI Taq DNA polymerase (Invitrogen Corp., Carlsbad, Calif., USA). The amplification reaction was composed of 5 µl of 10×PCR buffer, 2 µl of 25 mM MgCl$_2$, 1 µl of 10 mM dNTP, 1 µl of 10 uM Sense primer, 1 µl of 10 uM AUAP, 2 µl of the first strand cDNA, 0.5 µl of HIFI Taq, and 37.5 µl of deionized water. The PCR program was: 94° C., 3 mins; 10 cycles of 94° C. for 40 secs, 60° C. 40 secs with 1° C. decrease per cycle, 68° C. for 2 min; 25 cycles of 94° C. for 40 secs, 50° C. for 40 secs, 68° C. for 2 min; final extension at 68° C. for 10 mins.

The obtained PCR fragment was cloned into pGEM-T vector (Promega Corporation, Madison, Wis., USA) using a pGEM-T Vector System (Promega Corporation, Madison, Wis., USA) to generate plasmid AMG 1. The glucoamylase gene inserted in the plasmid AMG 1 was sequencing confirmed. *E. coli* strain TOP10 containing plasmid AMG 1 (designated NN059173), was deposited with the Deutsche Sammlung von Mikroorganismen and Zellkulturen GmbH (DSMZ) on Nov. 23, 2009, and assigned accession number as DSM 23123.

Example 2: Expression of Cloned *Penicillium oxalicum* Glucoamylase

The *Penicillium oxalicum* glucoamylase gene was re-cloned from the plasmid AMG 1 into an *Aspergillus* expression vector by PCR using two cloning primer F and primer R shown below, which were designed based on the known sequence and added tags for direct cloning by IN-FUSION™ strategy.

```
Primer F:
                             (SEQ ID NO: 5)
5' ACACAACTGGGGATCCACCATGCGTCTCACTCTATTATC Primer R:
                             (SEQ ID NO: 6)
5' AGATCTCGAGAAGCTTAAAACTGCCACACGTCGTTGG
```

A PCR reaction was performed with plasmid AMG 1 in order to amplify the full-length gene. The PCR reaction was composed of 40 µg of the plasmid AMG 1 DNA, 1 µl of each primer (100 µM); 12.5 µl of 2× Extensor Hi-Fidelity master mix (Extensor Hi-Fidelity Master Mix, ABgene, United Kingdom), and 9.5 µl of PCR-grade water. The PCR reaction was performed using a DYAD PCR machine (Bio-Rad Laboratories, Inc., Hercules, Calif., USA) programmed for 2 minutes at 94° C. followed by a 25 cycles of 94° C. for 15 seconds, 50° C. for 30 seconds, and 72° C. for 1 minute; and then 10 minutes at 72° C.

The reaction products were isolated by 1.0% agarose gel electrophoresis using 1×TAE buffer where an approximately 1.9 kb PCR product band was excised from the gel and purified using a GFX® PCR DNA and Gel Band Purification Kit (GE Healthcare, United Kingdom) according to manufacturer's instructions. DNA corresponding to the *Penicillium oxalicum* glucoamylase gene was cloned into an *Aspergillus* expression vector linearized with BamHI and HindIII, using an IN-FUSION™ Dry-Down PCR Cloning Kit (BD Biosciences, Palo Alto, Calif., USA) according to the manufacturer's instructions. The linearized vector construction is as described in WO 2005/042735 A1.

A 2 μl volume of the ligation mixture was used to transform 25 μl of Fusion Blue *E. coli* cells (included in the INFUSION™ Dry-Down PCR Cloning Kit). After a heat shock at 42° C. for 45 sec, and chilling on ice, 250 μl of SOC medium was added, and the cells were incubated at 37° C. at 225 rpm for 90 min before being plated out on LB agar plates containing 50 μg of ampicillin per ml, and cultivated overnight at 37° C. Selected colonies were inoculated in 3 ml of LB medium supplemented with 50 μg of ampicillin per ml and incubated at 37° C. at 225 rpm overnight. Plasmid DNA from the selected colonies was purified using Mini JETSTAR (Genomed, Germany) according to the manufacturer's instructions. *Penicillium oxalicum* glucoamylase gene sequence was verified by Sanger sequencing before heterologous expression. One of the plasmids was selected for further expression, and was named XYZ XYZ1471-4.

Protoplasts of *Aspergillus niger* MBin118 were prepared as described in WO 95/02043. One hundred μl of protoplast suspension were mixed with 2.5 μg of the XYZ1471-4 plasmid and 250 microliters of 60% PEG 4000 (Applichem) (polyethylene glycol, molecular weight 4,000), 10 mM $CaCl_2$, and 10 mM Tris-HCl pH 7.5 were added and gently mixed. The mixture was incubated at 37° C. for 30 minutes and the protoplasts were mixed with 6% low melting agarose (Biowhittaker Molecular Applications) in COVE sucrose (Cove, 1996, Biochim. Biophys. Acta 133:51-56) (1M) plates supplemented with 10 mM acetamid and 15 mM CsCl and added as a top layer on COVE sucrose (1M) plates supplemented with 10 mM acetamid and 15 mM CsCl for transformants selection (4 ml topagar per plate). After incubation for 5 days at 37° C. spores of sixteen transformants were picked up and seed on 750 μl YP-2% Maltose medium in 96 deepwell MT plates. After 5 days of stationary cultivation at 30° C., 10 μl of the culture-broth from each well was analyzed on a SDS-PAGE (Sodium dodecyl sulfate-polyacrylamide gel electrophoresis) gel, Griton XT Precast gel (BioRad, CA, USA) in order to identify the best transformants based on the ability to produce large amount of glucoamylase. A selected transformant was identified on the original transformation plate and was preserved as spores in a 20% glycerol stock and stored frozen (−80° C.).

Cultivation.

The selected transformant was inoculated in 100 ml of MLC media and cultivated at 30° C. for 2 days in 500 ml shake flasks on a rotary shaker. 3 ml of the culture broth was inoculated to 100 ml of M410 medium and cultivated at 30° C. for 3 days. The culture broth was centrifugated and the supernatant was filtrated using 0.2 μm membrane filters.

Alpha-Cyclodextrin Affinity Gel.

Ten grams of Epoxy-activated Sepharose 6B (GE Healthcare, Chalfont St. Giles, U.K) powder was suspended in and washed with distilled water on a sintered glass filter. The gel was suspended in coupling solution (100 ml of 12.5 mg/ml alpha-cyclodextrin, 0.5 M NaOH) and incubated at room temperature for one day with gentle shaking. The gel was washed with distilled water on a sintered glass filter, suspended in 100 ml of 1 M ethanolamine, pH 10, and incubated at 50° C. for 4 hours for blocking. The gel was then washed several times using 50 mM Tris-HCl, pH 8 and 50 mM NaOAc, pH 4.0 alternatively. The gel was finally packed in a 35-40 ml column using equilibration buffer (50 mM NaOAc, 150 mM NaCl, pH 4.5).

Purification of Glucoamylase from Culture Broth.

Culture broth from fermentation of *A. niger* MBin118 harboring the glucoamylase gene was filtrated through a 0.22 μm PES filter, and applied on a alpha-cyclodextrin affinity gel column previously equilibrated in 50 mM NaOAc, 150 mM NaCl, pH 4.5 buffer. Unbound material was washed off the column with equilibration buffer and the glucoamylase was eluted using the same buffer containing 10 mM beta-cyclodextrin over 3 column volumes.

The glucoamylase activity of the eluent was checked to see, if the glucoamylase had bound to the alpha-cyclodextrin affinity gel. The purified glucoamylase sample was then dialyzed against 20 mM NaOAc, pH 5.0. The purity was finally checked by SDS-PAGE, and only a single band was found.

Example 3: Construction and Expression of a Site-Directed Variant of *Penicillium oxalicum* Glucoamylase Two PCR reactions were performed with plasmid XYZ1471-4, described in Example 2, using primers K79V F and K79VR shown below, which were designed to substitute lysine K at position 79 from the mature sequence to varin V and primers F-NP003940 and R-NP003940 shown below, which were designed based on the known sequence and added tags for direct cloning by IN-FUSION™ strategy.

```
Primer K79V F 18 mer
                                          (SEQ ID NO: 7)
GCAGTCTTTCCAATTGAC Primer K79V R 18 mer
                                          (SEQ ID NO: 8)
AATTGGAAAGACTGCCCG Primer F-NP003940:
                                          (SEQ ID NO: 9)
5' ACACAACTGGGGATCCACCATGCGTCTCACTCTATTATC Primer R-NP003940:
                                          (SEQ ID NO: 10)
5' AGATCTCGAGAAGCTTAAAACTGCCACACGTCGTTGG
```

The PCR was performed using a PTC-200 DNA Engine under the conditions described below.

| PCR reaction system: | | Conditions: |
|---|---|---|
| 48.5 micro L H2O | 1 | 94° C. 2 min |
| 2 beads puRe Taq Ready-To- | 2 | 94° C. 30 sec |
| Go PCR Beads (Amersham bioscineces) | 3 | 55° C. 30 sec |
| 0.5 micro L X 2 100 pmole/micro L Primers | 4 | 72° C. 90 sec |
| (K79V F + Primer R-NP003940, K79V R + | 2-4 | 25 cycles |
| Primer F-NP003940) | 5 | 72° C. 10 min |
| 0.5 micro L Template DNA | | |

DNA fragments were recovered from agarose gel by the Qiagen gel extraction Kit according to the manufacturer's instruction. The resulting purified two fragments were cloned into an *Aspergillus* expression vector linearized with BamHI and HindIII, using an IN-FUSION™ Dry-Down PCR Cloning Kit (BD Biosciences, Palo Alto, Calif., USA) according to the manufacturer's instructions. The linearized vector construction is as described in WO 2005/042735 A1.

The ligation mixture was used to transform *E. coli* DH5α cells (TOYOBO). Selected colonies were inoculated in 3 ml of LB medium supplemented with 50 μg of ampicillin per ml and incubated at 37° C. at 225 rpm overnight. Plasmid DNA from the selected colonies was purified using Qiagen plasmid mini kit (Qiagen) according to the manufacturer's instructions. The sequence of *Penicillium oxalicum* glucoamylase site-directed variant gene sequence was verified before heterologous expression and one of the plasmids was selected for further expression, and was named pPoPE001.

Protoplasts of *Aspergillus niger* MBin118 were prepared as described in WO 95/02043. One hundred μl of protoplast suspension were mixed with 2.5 μg of the pPoPE001 plasmid and 250 microliters of 60% PEG 4000 (Applichem) (polyethylene glycol, molecular weight 4,000), 10 mM CaCl$_2$, and 10 mM Tris-HCl pH 7.5 were added and gently mixed. The mixture was incubated at 37° C. for 30 minutes and the protoplasts were mixed with 1% agarose L (Nippon Gene) in COVE sucrose (Cove, 1996, Biochim. Biophys. Acta 133:51-56) supplemented with 10 mM acetamid and 15 mM CsCl and added as a top layer on COVE sucrose plates supplemented with 10 mM acetamid and 15 mM CsCl for transformants selection (4 ml topagar per plate). After incubation for 5 days at 37° C. spores of sixteen transformants were picked up and seed on 750 μl YP-2% Maltose medium in 96 deepwell MT plates. After 5 days of stationary cultivation at 30° C., 10 μl of the culture-broth from each well was analyzed on a SDS-PAGE gel in order to identify the best transformants based on the ability to produce large amount of the glucoamylase.

Example 4: Purification of Site-Directed Po AMG Variant PE001

The selected transformant of the variant and the strain expressing the wild type *Penicillium oxalicum* glucoamylase described in Example 1 was cultivated in 100 ml of YP-2% maltose medium and the culture was filtrated through a 0.22 μm PES filter, and applied on a alpha-cyclodextrin affinity gel column previously equilibrated in 50 mM NaOAc, 150 mM NaCl, pH 4.5 buffer. Unbound materials was washed off the column with equilibration buffer and the glucoamylase was eluted using the same buffer containing 10 mM beta-cyclodextrin over 3 column volumes.

The glucoamylase activity of the eluent was checked to see, if the glucoamylase had bound to the alpha-cyclodextrin affinity gel. The purified glucoamylase samples were then dialyzed against 20 mM NaOAc, pH 5.0.

Example 5: Characterization of PE001

Protease Stability

40 μl enzyme solutions (1 mg/ml) in 50 mM sodium acetate buffer, pH 4.5, was mixed with 1/10 volume of 1 mg/ml protease solutions such as aspergillopepsinI described in Biochem J. 1975 April; 147(1):45-53. or the commercially available product from Sigma and aorsin described in Biochemical journal [0264-6021] Ichishima yr: 2003 vol: 371 iss: Pt 2 μg: 541 and incubated at 4 or 32° C. overnight. As a control experiment, H$_2$O was added to the sample instead of proteases. The samples were loaded on SDS-PAGE to see if the glucoamylases are cleaved by proteases.

In SDS-PAGE, PE001 only showed one band corresponding to the intact molecule, while the wild type glucoamylase was degraded by proteases and showed a band at lower molecular size at 60 kCa.

TABLE 1

The result of SDS-PAGE after protease treatment

| | Protease | | | | | | | | |
|---|---|---|---|---|---|---|---|---|---|
| | Wild type glucoamylase | | | | PE001 | | | | |
| | aspergillopepsin I | | aorsin | | aspergillopepsin I | | aorsin | | control |
| Incubation temperature (° C.) | 4 | 32 | 4 | 32 | 4 | 32 | 4 | 32 | 4 |
| intact glucoamylase (ca. 70 kDa) | 100% | 90% | 40% | 10% | 100% | 100% | 100% | 100% | 100% |
| cleaved glucoamylase (ca. 60 kDa) | N.D. | 10% | 60% | 90% | N.D. | N.D. | N.D | N.D. | N.D. |

N.D.: not detected.

Example 6: Less Cleavage During Cultivation

*Aspergillus* transformant of the variant and the wild type *Penicillium oxalicum* glucoamylase were cultivated in 6-well MT plates containing 4× diluted YP-2% maltose medium supplemented with 10 mM sodium acetate buffer, pH4.5, at 32° C. for 1 week.

The culture supernatants were loaded on SDS-PAGE.

TABLE 2

The result of SDS-PAGE of the culture supernatants

| | Wild type glucoamylase | PE001 |
|---|---|---|
| intact glucoamylase(ca. 70 kDa) | 90% | 100% |
| cleaved glucoamylase (ca. 60 kDa) | 10% | N.D. |

N.D.: not detected.

The wild type glucoamylase was cleaved by host proteases during fermentation, while the variant yielded only intact molecule.

Example 7: Glucoamylase Activity of Variant Compared to Parent

The glucoamylase activity measures as AGU as described above was checked for the purified enzymes of the wild type *Penicillium oxalicum* and the variant glucoamylase.

The Glucoamylase Unit (AGU) was defined as the amount of enzyme, which hydrolyzes 1 micromole maltose per minute under the standard conditions (37° C., pH 4.3, substrate: maltose 100 mM, buffer: acetate 0.1 M, reaction time 6 minutes).

TABLE 3

| Relative specific activity | AGU/mg |
|---|---|
| *Penicillium oxalicum* wt | 100% |
| *Penicillium oxalicum* PE001 (SEQ ID NO: 3) | 102% |

Example 8: Purification of Glycoamylase Variants Having Increased Thermostability The variants of the invention showing increased thermostability may be constructed and expressed similar to the procedure described in Example 3. All variants according to the present invention were derived from the PE001 as the parent glucoamylase, and disclosed in SEQ ID NO: 3. After expression in YPM medium, variants comprising the T65A or Q327F substitution was micro-purified as follows:

Mycelium was removed by filtration through a 0.22 µm filter. 50 µl column material (alpha-cyclodextrin coupled to Mini-Leak divinylsulfone-activated agarose medium according to manufacturers recommendations) was added to the wells of a filter plate (Whatman, Unifilter 800 µl, 25-30 µm MBPP). The column material was equilibrated with binding buffer (200 mM sodium acetate pH 4.5) by two times addition of 200 µl buffer, vigorous shaking for 10 min (Heidolph, Titramax 101, 1000 rpm) and removal of buffer by vacuum (Whatman, UniVac 3). Subsequently, 400 µl culture supernatant and 100 µl binding buffer was added and the plate incubated 30 min with vigorous shaking. Unbound material was removed by vacuum and the binding step was repeated. Normally 4 wells were used per variant. Three washing steps were then performed with 200 µl buffer of decreasing ionic strength added (50/10/5 mM sodium acetate, pH 4.5), shaking for 15 min and removal of buffer by vacuum. Elution of the bound AMG was achieved by two times addition of 100 µl elution buffer (250 mM sodium acetate, 0.1% alpha-cyclodextrin, pH 6.0), shaking for 15 min and collection of eluted material in a microtiter plate by vacuum. Pooled eluates were concentrated and buffer changed to 50 mM sodium acetate pH 4.5 using centrifugal filter units with 10 kDa cut-off (Millipore Microcon Ultracel YM-10). Micropurified samples were stored at −18° C. until testing of thermostability.

Example 9: Protein Thermal Unfolding Analysis (TSA, Thermal Shift Assay)

Protein thermal unfolding of the T65A and Q327F variants, was monitored using Sypro Orange (In-vitrogen, S-6650) and was performed using a real-time PCR instrument (Applied Biosystems; Step-One-Plus).

In a 96-well plate, 25 microliter micropurified sample in 50 mM Acetate pH4.5 at approx. 100 microgram/ml was mixed (5:1) with Sypro Orange (resulting conc.=5×; stock solution from supplier=5000×). The plate was sealed with an optical PCR seal. The PCR instrument was set at a scan-rate of 76 degrees C. pr. hr, starting at 25° C. and finishing at 96° C.

Protein thermal unfolding of the E501V+Y504T variant, was monitored using Sypro Orange (In-vitrogen, S-6650) and was performed using a real-time PCR instrument (Applied Biosystems; Step-One-Plus).

In a 96-well plate, 15 microliter purified sample in 50 mM Acetate pH4.5 at approx. 50 microgram/ml was mixed (1:1) with Sypro Orange (resulting conc.=5×; stock solution from supplier=5000×) with or without 200 ppm Acarbose (Sigma A8980). The plate was sealed with an optical PCR seal. The PCR instrument was set at a scan-rate of 76 degrees C. pr. hr, starting at 25° C. and finishing at 96° C.

Fluorescence was monitored every 20 seconds using in-built LED blue light for excitation and ROX-filter (610 nm, emission).

Tm-values were calculated as the maximum value of the first derivative (dF/dK) (ref.: Gregory et al; *J Biomol Screen* 2009 14: 700)

TABLE 4a

| Sample | Tm (Deg. Celsius) +/− 0.4 |
|---|---|
| PO-AMG (PE001) | 80.3 |
| Variant Q327F | 82.3 |
| Variant T65A | 81.9 |

TABLE 4b

| Sample | Tm (Deg. Celsius) +/− 0.4 | |
|---|---|---|
| Acarbose: | − | + |
| PO-AMG (PE001) | 79.5 | 86.9 |
| Variant E501V Y504T | 79.5 | 95.2 |

Example 10: Thermostability Analysis by Differential Scanning Calorimetry (DSC)

Additional site specific variants having substitutions and/or deletions at specific positions were constructed basically as described in Example 3 and purified as described in Example 4.

The thermostability of the purified Po-AMG PE001 derived variants were determined at pH 4.0 or 4.8 (50 mM Sodium Acetate) by Differential Scanning calorimetry (DSC) using a VP-Capillary Differential Scanning calorimeter (MicroCal Inc., Piscataway, N.J., USA). The thermal denaturation temperature, Td (° C.), was taken as the top of the denaturation peak (major endothermic peak) in thermograms (Cp vs. T) obtained after heating enzyme solutions in selected buffers (50 mM Sodium Acetate, pH 4.0 or 4.8) at a constant programmed heating rate of 200 K/hr.

Sample- and reference-solutions (approximately 0.3 ml) were loaded into the calorimeter (reference: buffer without enzyme) from storage conditions at 10° C. and thermally pre-equilibrated for 10 minutes at 20° C. prior to DSC scan from 20° C. to 110° C. Denaturation temperatures were determined with an accuracy of approximately +/−1° C.

The isolated variants and the DSC data are disclosed in Table 5 below.

TABLE 5

| Po-AMG name | Mutations | DSC Td (° C.) @ pH 4.0 | DSC Td (° C.) @ pH 4.8 |
|---|---|---|---|
| PE001 (SEQ ID NO: 3) | | 82.1 | 83.4 |
| PE167 | E501V Y504T | 82.1 | |
| PE481 | T65A K161S | 84.1 | 86.0 |
| PE487 | T65A Q405T | 83.2 | |
| PE490 | T65A Q327W | 87.3 | |
| PE491 | T65A Q327F | 87.7 | |
| PE492 | T65A Q327Y | 87.3 | |
| PE493 | P11F T65A Q327F | 87.8 | 88.5 |
| PE497 | R1K D3W K5Q G7V N8S T10K P11S T65A Q327F | 87.8 | 88.0 |
| PE498 | P2N P4S P11F T65A Q327F | 88.3 | 88.4 |
| PE003 | P11F D26C K33C T65A Q327F | 83.3 | 84.0 |
| PE009 | P2N P4S P11F T65A Q327W E501V Y504T | 88.8 | |
| PE002 | R1E D3N P4G G6R G7A N8A T10D P11D T65A Q327F | 87.5 | 88.2 |
| PE005 | P11F T65A Q327W | 87.4 | 88.0 |
| PE008 | P2N P4S P11F T65A Q327F E501V Y504T | 89.4 | 90.2 |
| PE010 | P11F T65A Q327W E501V Y504T | | 89.7 |

TABLE 5-continued

| Po-AMG name | Mutations | DSC Td (° C.) @ pH 4.0 | DSC Td (° C.) @ pH 4.8 |
|---|---|---|---|
| PE507 | T65A Q327F E501V Y504T | | 89.3 |
| PE513 | T65A S105P Q327W | | 87.0 |
| PE514 | T65A S105P Q327F | | 87.4 |
| PE515 | T65A Q327W S364P | | 87.8 |
| PE516 | T65A Q327F S364P | | 88.0 |
| PE517 | T65A S103N Q327F | | 88.9 |
| PE022 | P2N P4S P11F K34Y T65A Q327F | | 89.7 |
| PE023 | P2N P4S P11F T65A Q327F D445N V447S | | 89.9 |
| PE032 | P2N P4S P11F T65A I172V Q327F | | 88.7 |
| PE049 | P2N P4S P11F T65A Q327F N502* | | 88.4 |
| PE055 | P2N P4S P11F T65A Q327F N502T P563S K571E | | 88.0 |
| PE057 | P2N P4S P11F R31S K33V T65A Q327F N564D K571S | | 89.5 |
| PE058 | P2N P4S P11F T65A Q327F S377T | | 88.6 |
| PE064 | P2N P4S P11F T65A V325T Q327W | | 88.0 |
| PE068 | P2N P4S P11F T65A Q327F D445N V447S E501V Y504T | | 90.2 |
| PE069 | P2N P4S P11F T65A I172V Q327F E501V Y504T | | 90.2 |
| PE073 | P2N P4S P11F T65A Q327F S377T E501V Y504T | | 90.1 |
| PE074 | P2N P4S P11F D26N K34Y T65A Q327F | | 89.1 |
| PE076 | P2N P4S P11F T65A Q327F I375A E501V Y504T | | 90.2 |
| PE079 | P2N P4S P11F T65A K218A K221D Q327F E501V Y504T | | 90.9 |
| PE085 | P2N P4S P11F T65A S103N Q327F E501V Y504T | | 91.3 |
| PE086 | P2N P4S T10D T65A Q327F E501V Y504T | | 90.4 |
| PE088 | P2N P4S F12Y T65A Q327F E501V Y504T | | 90.4 |
| PE097 | K5A P11F T65A Q327F E501V Y504T | | 90.0 |
| PE101 | P2N P4S T10E E18N T65A Q327F E501V Y504T | | 89.9 |
| PE102 | P2N T10E E18N T65A Q327F E501V Y504T | | 89.8 |
| PE084 | P2N P4S P11F T65A Q327F E501V Y504T T568N | | 90.5 |
| PE108 | P2N P4S P11F T65A Q327F E501V Y504T K524T G526A | | 88.6 |
| PE126 | P2N P4S P11F K34Y T65A Q327F D445N V447S E501V Y504T | | 91.8 |
| PE129 | P2N P4S P11F R31S K33V T65A Q327F D445N V447S E501V Y504T | | 91.7 |
| PE087 | P2N P4S P11F D26N K34Y T65A Q327F E501V Y504T | | 89.8 |
| PE091 | P2N P4S P11F T65A F80* Q327F E501V Y504T | | 89.9 |
| PE100 | P2N P4S P11F T65A K112S Q327F E501V Y504T | | 89.8 |
| PE107 | P2N P4S P11F T65A Q327F E501V Y504T T516P K524T G526A | | 90.3 |
| PE110 | P2N P4S P11F T65A Q327F E501V N502T Y504* | | 90.6 |

Example 11: Thermostability Analysis by Thermo-Stress Test and pNPG Assay

Starting from one of the identified substitution variants from example 10, identified as PE008, additional variants were tested by a thermo-stress assay in which the supernatant from growth cultures were assayed for glucoamylase (AMG) activity after a heat shock at 83° C. for 5 min.

After the heat-shock the residual activity of the variant was measured as well as in a non-stressed sample.

Description of Po-AMG pNPG Activity Assay:

The *Penicillium oxalicum* glucoamylase pNPG activity assay is a spectrometric endpoint assay where the samples are split in two and measured thermo-stressed and non-thermo-stressed. The data output is therefore a measurement of residual activity in the stressed samples.

Growth:

A sterile micro titer plate (MTP) was added 200 μL rich growth media (FT X-14 without Dowfax) to each well. The strains of interest were inoculated in triplicates directly from frozen stocks to the MTP. Benchmark was inoculated in 20 wells. Non-inoculated wells with media were used as assay blanks. The MTP was placed in a plastic box containing wet tissue to prevent evaporation from the wells during incubation. The plastic box was placed at 34° C. for 4 days.

Assay:

50 μL supernatant was transferred to 50 μL 0.5M NaAc pH 4.8 to obtain correct sample pH.

50 μL dilution was transferred to a PCR plate and thermo-stressed at 83° C. for 5 minutes in a PCR machine. The remaining half of the dilution was kept at RT.

20 μL of both stressed and unstressed samples was transferred to a standard MTP. 20 μL pNPG-substrate was added to start the reaction. The plate was incubated at RT for 1 h.

The reaction was stopped and the colour developed by adding 50 μL 0.5M $Na_2CO_3$. The yellow colour was measured on a plate reader (Molecular Devices) at 405 nm.

Buffers:

0.5M NaAc pH 4.8

0.25M NaAc pH 4.8

Substrate, 6 mM pNPG:

15 mg 4-nitrophenyl D-glucopyranoside in 10 mL 0.25 NaAc pH 4.8

Stop/Developing Solution:

0.5M $Na_2CO_3$

Data Treatment:

In Excel the raw Abs405 data from both stressed and unstressed samples were blank subtracted with their respective blanks. The residual activity (% res. act.=$(Abs_{unstressed}-(Abs_{unstressed}-Abs_{stressed}))/Abs_{unstressed}*100\%$) was calculated and plotted relative to benchmark, Po-amg0008.

TABLE 6

| Po-AMG name | Mutations | % residual activity |
|---|---|---|
| PE008 | P2N P4S P11F T65A Q327F E501V Y504T | 100 |
| PE085 | P2N P4S P11F T65A S103N Q327F E501V Y504T | 127 |
| PE097 | K5A P11F T65A Q327F E501V Y504T | 106 |
| PE107 | P2N P4S P11F T65A Q327F E501V Y504T T516P K524T G526A | 109 |
| PE130 | P2N P4S P11F T65A V79A Q327F E501V Y504T | 111 |
| PE131 | P2N P4S P11F T65A V79G Q327F E501V Y504T | 112 |
| PE132 | P2N P4S P11F T65A V79I Q327F E501V Y504T | 101 |
| PE133 | P2N P4S P11F T65A V79L Q327F E501V Y504T | 102 |

TABLE 6-continued

| Po-AMG name | Mutations | % residual activity |
|---|---|---|
| PE134 | P2N P4S P11F T65A V79S Q327F E501V Y504T | 104 |
| PE150 | P2N P4S P11F T65A L72V Q327F E501V Y504T | 101 |
| PE155 | S255N Q327F E501V Y504T | 105 |

TABLE 7

| Po-AMG name | Mutations | % residual activity |
|---|---|---|
| PE008 | P2N P4S P11F T65A Q327F E501V Y504T | 100 |
| PE179 | P2N P4S P11F T65A E74N V79K Q327F E501V Y504T | 108 |
| PE180 | P2N P4S P11F T65A G220N Q327F E501V Y504T | 108 |
| PE181 | P2N P4S P11F T65A Y245N Q327F E501V Y504T | 102 |
| PE184 | P2N P4S P11F T65A Q253N Q327F E501V Y504T | 110 |
| PE185 | P2N P4S P11F T65A D279N Q327F E501V Y504T | 108 |
| PE186 | P2N P4S P11F T65A Q327F S359N E501V Y504T | 108 |
| PE187 | P2N P4S P11F T65A Q327F D370N E501V Y504T | 102 |
| PE192 | P2N P4S P11F T65A Q327F V460S E501V Y504T | 102 |
| PE193 | P2N P4S P11F T65A Q327F V460T P468T E501V Y504T | 102 |
| PE195 | P2N P4S P11F T65A Q327F T463N E501V Y504T | 103 |
| PE196 | P2N P4S P11F T65A Q327F S465N E501V Y504T | 106 |
| PE198 | P2N P4S P11F T65A Q327F T477N E501V Y504T | 106 |

Example 12: Test for Glucoamylase Activity of Thermo-Stable Variants According to the Invention All of the above described variants disclosed in tables 5, 6, and 7 have been verified for Glucoamylase activity on culture supernatants using the pNPG assay described in Example 11.

The invention described and claimed herein is not to be limited in scope by the specific aspects herein disclosed, since these aspects are intended as illustrations of several aspects of the invention. Any equivalent aspects are intended to be within the scope of this invention. Indeed, various modifications of the invention in addition to those shown and described herein will become apparent to those skilled in the art from the foregoing description. Such modifications are also intended to fall within the scope of the appended claims. In the case of conflict, the present disclosure including definitions will control.

The present invention is further described by the following numbered paragraphs.

[1] A glucoamylase variant, comprising a substitution or deletion at one or more positions corresponding to positions 1, 2, 3, 4, 5, 6, 7, 8, 10, 11, 12, 18, 26, 31, 33, 34, 65, 72, 74, 79, 80, 103, 105, 112, 161, 172, 218, 220, 221, 245, 253, 255, 279, 325, 327, 359, 364, 370, 375, 377, 405, 445, 447, 460, 463, 465, 468, 477, 501, 502, 504, 516, 524, 526, 563, 564, 568, 571 of the polypeptide of SEQ ID NO: 3, wherein the variant has glucoamylase activity.

[2] The variant of paragraphs 1, selected from the group consisting of:
a) a polypeptide having at least 65% sequence identity to the polypeptide of SEQ ID NO: 3;
b) a polypeptide encoded by a polynucleotide that hybridizes under low stringency conditions with (i) the mature polypeptide coding sequence of SEQ ID NO: 1, or (ii) the full-length complement of (i);
c) a polypeptide encoded by a polynucleotide having at least 65% identity to the mature polypeptide coding sequence of SEQ ID NO: 1; and
d) a fragment of the polypeptide of SEQ ID NO: 3, which has glucoamylase activity.

[3] The variant of any of paragraphs 1-2, wherein the variant has at least at least 65%, at least 70%, at least 75%, at least 80%, at least 85%, at least 90%, at least 95%, at least 96%, at least 97%, at least 98% or at least 99% sequence identity to the polypeptide of SEQ ID NO: 3.

[4] The variant of any of paragraphs 1-2, wherein the variant is encoded by a polynucleotide that hybridizes under low stringency conditions, medium stringency conditions, medium-high stringency conditions, high stringency conditions, or very high stringency conditions with (i) the mature polypeptide coding sequence of SEQ ID NO: 1, or (ii) the full-length complement of (i).

[5] The variant of any of paragraphs 1-2, wherein the variant is encoded by a polynucleotide having at least 65%, at least 70%, at least 75%, at least 80%, at least 85%, at least 90%, at least 95%, at least 96%, at least 97%, at least 98%, at least 99% sequence identity to the mature polypeptide coding sequence of SEQ ID NO: 1.

[6] The variant of any of paragraphs 1-5, which is a variant of a parent glucoamylase selected from the group consisting of:
a) a polypeptide having at least 65% sequence identity to the polypeptide of SEQ ID NO: 3;
b) a polypeptide encoded by a polynucleotide that hybridizes under low stringency conditions with (i) the mature polypeptide coding sequence of SEQ ID NO: 1, or (ii) the full-length complement of (i);
c) a polypeptide encoded by a polynucleotide having at least 65% identity to the mature polypeptide coding sequence of SEQ ID NO: 1; and
d) a fragment of the mature polypeptide of SEQ ID NO: 3, which has glucoamylase activity.

[7] The variant of paragraph 6, wherein the parent glucoamylase has at least 65%, at least 70%, at least 75%, at least 80%, at least 85%, at least 90%, at least 95%, at least 96%, at least 97%, at least 98%, at least 99% or 100% sequence identity to the polypeptide of SEQ ID NO: 3.

[8] The variant of paragraph 6 or 7, wherein the parent glucoamylase is encoded by a polynucleotide that hybridizes under low stringency conditions, medium stringency conditions, medium-high stringency conditions, high stringency conditions, or very high stringency conditions with (i) the mature polypeptide coding sequence of SEQ ID NO: 1 or (ii) the full-length complement of (i).

[9] The variant of any of paragraphs 6-8, wherein the parent glucoamylase is encoded by a polynucleotide having at least 65%, at least 70%, at least 75%, at least 80%, at least 85%, at least 90%, at least 95%, at least 96%, at least 97%, at least 98%, at least 99%, or 100% sequence identity to the mature polypeptide coding sequence of SEQ ID NO: 1.

[10] The variant of any of paragraphs 1-9, wherein the number of substitutions is 1-20, e.g., 1-10 and 1-5, such as 1, 2, 3, 4, 5, 6, 7, 8, 9 or 10 substitutions.

[11] The variant of any of the preceding paragraphs, comprising a substitution or deletion in at least one position selected from position 65, 327, 501, 504 of SEQ ID NO: 3.

[12] The variant of any of the preceding paragraphs, wherein the variant comprises or consists of one or more substitutions selected from the group consisting of T65A, Q327F, E501V, Y504T, Y504*.

[13] The variant of any of the preceding paragraphs, wherein the variant comprises at least one of the following substitutions or combinations of substitutions:
T65A; or
Q327F; or
E501V; or
Y504T; or
Y504*; or
T65A+Q327F; or
T65A+E501V; or
T65A+Y504T; or
T65A+Y504*; or
Q327F+E501V; or
Q327F+Y504T; or
Q327F+Y504*; or
E501V+Y504T; or
E501V+Y504*; or
T65A+Q327F+E501V; or
T65A+Q327F+Y504T; or
T65A+E501V+Y504T; or
Q327F+E501V+Y504T; or
T65A+Q327F+Y504*; or
T65A+E501V+Y504*; or
Q327F+E501V+Y504*; or
T65A+Q327F+E501V+Y504T; or
T65A+Q327F+E501V+Y504*.

14. The variant of any of the paragraphs 1-13, wherein the variant comprises at least one of the following combinations of substitutions:
E501V+Y504T;
T65A+K161S;
T65A+Q405T;
T65A+Q327W;
T65A+Q327F;
T65A+Q327Y;
P11F+T65A+Q327F;
R1K+D3W+K5Q+G7V+N8S+T10K+P11S+T65A+Q327F;
P2N+P4S+P11F+T65A+Q327F;
P11F+D26C+K33C+T65A+Q327F;
P2N+P4S+P11F+T65A+Q327W+E501V+Y504T;
R1E+D3N+P4G+G6R+G7A+N8A+T10D+P11D+T65A+Q327F;
P11F+T65A+Q327W;
P2N+P4S+P11F+T65A+Q327F+E501V+Y504T;
P11F+T65A+Q327W+E501V+Y504T;
T65A+Q327F+E501V+Y504T;
T65A+S105P+Q327W;
T65A+S105P+Q327F;
T65A+Q327W+S364P;
T65A+Q327F+S364P;
T65A+S103N+Q327F;
P2N+P4S+P11F+K34Y+T65A+Q327F;
P2N+P4S+P11F+T65A+Q327F+D445N+V447S;
P2N+P4S+P11F+T65A+I172V+Q327F;
P2N+P4S+P11F+T65A+Q327F+N502*;
P2N+P4S+P11F+T65A+Q327F+N502T+P563S+K571E;
P2N+P4S+P11F+R31S+K33V+T65A+Q327F+N564D+K571S;
P2N+P4S+P11F+T65A+Q327F+S377T;
P2N+P4S+P11F+T65A+V325T+Q327W;
P2N+P4S+P11F+T65A+Q327F+D445N+V447S+E501V+Y504T;
P2N+P4S+P11F+T65A+I172V+Q327F+E501V+Y504T;
P2N+P4S+P11F+T65A+Q327F+S377T+E501V+Y504T;
P2N+P4S+P11F+D26N+K34Y+T65A+Q327F;
P2N+P4S+P11F+T65A+Q327F+I375A+E501V+Y504T;
P2N+P4S+P11F+T65A+K218A+K221D+Q327F+E501V+Y504T;
P2N+P4S+P11F+T65A+S103N+Q327F+E501V+Y504T;
P2N+P4S+T10D+T65A+Q327F+E501V+Y504T;
P2N+P4S+F12Y+T65A+Q327F+E501V+Y504T;
K5A+P11F+T65A+Q327F+E501V+Y504T;
P2N+P4S+T10E+E18N+T65A+Q327F+E501V+Y504T;
P2N+T10E+E18N+T65A+Q327F+E501V+Y504T;
P2N+P4S+P11F+T65A+Q327F+E501V+Y504T+T568N;
P2N+P4S+P11F+T65A+Q327F+E501V+Y504T+K524T+G526A;
P2N+P4S+P11F+K34Y+T65A+Q327F+D445N+V447S+E501V+Y504T;
P2N+P4S+P11F+R31S+K33V+T65A+Q327F+D445N+V447S+E501V+Y504T;
P2N+P4S+P11F+D26N+K34Y+T65A+Q327F+E501V+Y504T;
P2N+P4S+P11F+T65A+F80*+Q327F+E501V+Y504T;
P2N+P4S+P11F+T65A+K112S+Q327F+E501V+Y504T;
P2N+P4S+P11F+T65A+Q327F+E501V+Y504T+T516P+K524T+G526A;
P2N+P4S+P11F+T65A+Q327F+E501V+N502T+Y504*;
P2N+P4S+P11F+T65A+Q327F+E501V+Y504T;
P2N+P4S+P11F+T65A+S103N+Q327F+E501V+Y504T;
K5A+P11F+T65A+Q327F+E501V+Y504T;
P2N+P4S+P11F+T65A+Q327F+E501V+Y504T+T516P+K524T+G526A;
P2N+P4S+P11F+T65A+V79A+Q327F+E501V+Y504T;
P2N+P4S+P11F+T65A+V79G+Q327F+E501V+Y504T;
P2N+P4S+P11F+T65A+V79I+Q327F+E501V+Y504T;
P2N+P4S+P11F+T65A+V79L+Q327F+E501V+Y504T;
P2N+P4S+P11F+T65A+V79S+Q327F+E501V+Y504T;
P2N+P4S+P11F+T65A+L72V+Q327F+E501V+Y504T;
S255N+Q327F+E501V+Y504T;
P2N+P4S+P11F+T65A+E74N+V79K+Q327F+E501V+Y504T;
P2N+P4S+P11F+T65A+G220N+Q327F+E501V+Y504T;
P2N+P4S+P11F+T65A+Y245N+Q327F+E501V+Y504T;
P2N+P4S+P11F+T65A+Q253N+Q327F+E501V+Y504T;
P2N+P4S+P11F+T65A+D279N+Q327F+E501V+Y504T;
P2N+P4S+P11F+T65A+Q327F+S359N+E501V+Y504T;
P2N+P4S+P11F+T65A+Q327F+D370N+E501V+Y504T;
P2N+P4S+P11F+T65A+Q327F+V460S+E501V+Y504T;
P2N+P4S+P11F+T65A+Q327F+V460T+P468T+E501V+Y504T;
P2N+P4S+P11F+T65A+Q327F+T463N+E501V+Y504T;
P2N+P4S+P11F+T65A+Q327F+S465N+E501V+Y504T; or
P2N+P4S+P11F+T65A+Q327F+T477N+E501V+Y504T.

[15] The variant of any of paragraphs 1-14, which has an improved property relative to the parent, wherein the improved property is reduced sensitivity to protease degradation.

[16] The variant of any of paragraphs, 1-15, which has an improved property relative to the parent, wherein the improved property is improved thermostability.

[17] A variant glucoamylase catalytic domain comprising a substitution at one or more positions corresponding to positions 10, 11, 12, 18, 26, 31, 33, 34, 65, 72, 74, 79, 80, 103, 105, 112, 161, 172, 218, 220, 221, 245, 253, 255, 279, 325, 327, 359, 364, 370, 375, 377, 405, 445, 447, 460, 463, 465, 468 of the polypeptide of SEQ ID NO: 3, wherein the variant has glucoamylase activity.

[18] The variant glucoamylase catalytic domain of paragraph 17 selected from the group consisting of:
(a) a catalytic domain having at least 65% sequence identity to amino acids 30 to 494 of SEQ ID NO: 2;
(b) a catalytic domain encoded by a polynucleotide that hybridizes under medium stringency conditions with (i) nucleotides 88 to 1482 of SEQ ID NO: 1 or (ii) the full-length complement of (i);
(c) a catalytic domain encoded by a polynucleotide having at least 65% sequence identity to (i) nucleotides 88 to 1482 of SEQ ID NO: 1; and wherein the catalytic domain has glucoamylase activity.

[19] The polypeptide of paragraph 18, further comprising a linker and a carbohydrate binding domain.

[20] A composition comprising the polypeptide of any of paragraphs 1-19.

[21] A composition according to paragraph 20, comprising an alpha-amylase and a polypeptide of any of paragraphs 1-19.

[22] A use of a polypeptide of any of paragraphs 1-19 for production of syrup and/or a fermentation product.

[23] The use according to paragraph 22, wherein the starting material is gelatinized or un-gelatinized starch-containing material.

[24] A use of a polypeptide of any of paragraphs 1-19 for brewing.

[25] A process of producing a fermentation product from starch-containing material comprising the steps of:
(a) liquefying starch-containing material in the presence of an alpha amylase;
(b) saccharifying the liquefied material; and
(c) fermenting with a fermenting organism;
wherein step (a) and/or step (b) is carried out using at least a glucoamylase of any of paragraphs 1-19.

[26] A process of producing a fermentation product from starch-containing material, comprising the steps of:
(a) saccharifying starch-containing material at a temperature below the initial gelatinization temperature of said starch-containing material; and
(b) fermenting with a fermenting organism,
wherein step (a) is carried out using at least a glucoamylase of any of paragraphs 1-19.

[27] An isolated polynucleotide encoding the polypeptide of any of paragraphs 1-19.

[28] A nucleic acid construct or expression vector comprising the polynucleotide of paragraph 27 operably linked to one or more control sequences that direct the production of the polypeptide in an expression host.

[29] A recombinant host cell comprising the polynucleotide of paragraph 27 operably linked to one or more control sequences that direct the production of the polypeptide.

[30] A method of producing the polypeptide of any of paragraphs 1-19, comprising:
(a) cultivating a cell, which in its wild-type form produces the polypeptide, under conditions conducive for production of the polypeptide; and
(b) recovering the polypeptide.

[31] A method of producing a polypeptide of any of paragraphs 1-19, comprising:
(a) cultivating the host cell of paragraph 29 under conditions conducive for production of the polypeptide; and
(b) recovering the polypeptide.

[32] A nucleic acid construct comprising the polynucleotide of paragraph 27.

[33] An expression vector comprising the polynucleotide of paragraph 27.

[34] A host cell comprising the polynucleotide of paragraph 27.

The invention claimed is:

1. A glucoamylase variant having improved thermostability, comprising a substitution at a position corresponding to position 2 of the polypeptide of SEQ ID NO: 3, wherein the variant has glucoamylase activity and wherein the variant has at least 90% sequence identity to the polypeptide of SEQ ID NO: 3.

2. The variant of claim 1, wherein the variant has at least 95% sequence identity to SEQ ID NO: 3.

3. The variant of claim 1, wherein the variant has at least 97% sequence identity to the polypeptide of SEQ ID NO: 3.

4. The variant of claim 1, wherein the variant has at least 98% sequence identity to SEQ ID NO:3.

5. The variant of claim 1, wherein the variant has at least 99% sequence identity to SEQ ID NO: 3.

6. The variant of claim 1, wherein the number of substitutions is 1-20.

7. The variant of claim 1, comprising a substitution or deletion in at least one position selected from the group consisting of 65, 327, 501, and 504 of SEQ ID NO: 3.

8. The variant of claim 1, wherein the variant comprises or consists of one or more alterations selected from the group consisting of T65A, Q327F, E501V, Y504T, and Y504*.

9. The variant of claim 1, wherein the variant comprises at least one of the following substitutions or combinations of substitutions:
T65A; or
Q327F; or
E501V; or
Y504T; or
Y504*; or
T65A+Q327F; or
T65A+E501V; or
T65A+Y504T; or
T65A+Y504*; or
Q327F+E501V; or
Q327F+Y504T; or
Q327F+Y504*; or
E501V+Y504T; or
E501V+Y504*; or T65A+Q327F+E501V; or
T65A+Q327F+Y504T; or
T65A+E501V+Y504T; or
Q327F+E501V+Y504T; or
T65A+Q327F+Y504*; or
T65A+E501V+Y504*; or
Q327F+E501V+Y504*; or
T65A+Q327F+E501V+Y504T; or
T65A+Q327F+E501V+Y504*.

10. The variant of claim 1, wherein the variant comprises at least one of the following combinations of substitutions:
E501V+Y504T;
T65A+K161S;
T65A+Q405T;
T65A+Q327W;
T65A+Q327F;
T65A+Q327Y;
P11F+T65A+Q327F;
R1K+D3W+K5Q+G7V+N8S+T10K+P11S+T65A+ Q327F;
P2N+P4S+P11F+T65A+Q327F;
P11F+D26C+K330+T65A+Q327F;
P2N+P4S+P11F+T65A+Q327W+E501V+Y504T;
R1E+D3N+P4G+G6R+G7A+N8A+T10D+P11D+ T65A+Q327F;
P11F+T65A+Q327W;
P2N+P4S+P11F+T65A+Q327F+E501V+Y504T;
P11F+T65A+Q327W+E501V+Y504T;
T65A+Q327F+E501V+Y504T;
T65A+S105P+Q327W;
T65A+S105P+Q327F;
T65A+Q327W+S364P;
T65A+Q327F+S364P;
T65A+S103N+Q327F;
P2N+P4S+P11F+K34Y+T65A+Q327F;
P2N+P4S+P11F+T65A+Q327F+D445N+V447S;
P2N+P4S+P11F+T65A+I172V+Q327F;
P2N+P4S+P11F+T65A+Q327F+N502*;
P2N+P4S+P11F+T65A+Q327F+N502T+P563S+K571E;
P2N+P4S+P11F+R31S+K33V+T65A+Q327F+N564D+ K571S;
P2N+P4S+P11F+T65A+Q327F+S377T;
P2N+P4S+P11F+T65A+V325T+Q327W;
P2N+P4S+P11F+T65A+Q327F+D445N+V447S+ E501V+Y504T;
P2N+P4S+P11F+T65A+I172V+Q327F+E501V+Y504T;
P2N+P4S+P11F+T65A+Q327F+S377T+E501V+Y504T;
P2N+P4S+P11F+D26N+K34Y+T65A+Q327F;
P2N+P4S+P11F+T65A+Q327F+I375A+E501V+Y504T;
P2N+P4S+P11F+T65A+K218A+K221D+Q327F+ E501V+Y504T;
P2N+P4S+P11F+T65A+S103N+Q327F+E501V+ Y504T;
P2N+P4S+T10D+T65A+Q327F+E501V+Y504T;
P2N+P4S+F12Y+T65A+Q327F+E501V+Y504T;
K5A+P11F+T65A+Q327F+E501V+Y504T;
P2N+P4S+T10E+E18N+T65A+Q327F+E501V+Y504T;
P2N+T10E+E18N+T65A+Q327F+E501V+Y504T;
P2N+P4S+P11F+T65A+Q327F+E501V+Y504T+ T568N;
P2N+P4S+P11F+T65A+Q327F+E501V+Y504T+ K524T+G526A;
P2N+P4S+P11F+K34Y+T65A+Q327F+D445N+ V447S+E501V+Y504T;
P2N+P4S+P11F+R31S+K33V+T65A+Q327F+D445N+ V447S+E501V+Y504T;
P2N+P4S+P11F+D26N+K34Y+T65A+Q327F+E501V+ Y504T;
P2N+P4S+P11F+T65A+F80*+Q327F+E501V+Y504T;
P2N+P4S+P11F+T65A+K112S+Q327F+E501V+ Y504T;
P2N+P4S+P11F+T65A+Q327F+E501V+Y504T+ T516P+K524T+G526A;
P2N+P4S+P11F+T65A+Q327F+E501V+N502T+ Y504*;
P2N+P4S+P11F+T65A+Q327F+E501V+Y504T;
P2N+P4S+P11F+T65A+S103N+Q327F+E501V+ Y504T;
K5A+P11F+T65A+Q327F+E501V+Y504T;
P2N+P4S+P11F+T65A+Q327F+E501V+Y504T+ T516P+K524T+G526A;
P2N+P4S+P11F+T65A+V79A+Q327F+E501V+Y504T;
P2N+P4S+P11F+T65A+V79G+Q327F+E501V+Y504T;
P2N+P4S+P11F+T65A+V79I+Q327F+E501V+Y504T;
P2N+P4S+P11F+T65A+V79L+Q327F+E501V+Y504T;
P2N+P4S+P11F+T65A+V79S+Q327F+E501V+Y504T;
P2N+P4S+P11F+T65A+L72V+Q327F+E501V+Y504T;
S255N+Q327F+E501V+Y504T;
P2N+P4S+P11F+T65A+E74N+V79K+Q327F+E501V+ Y504T;
P2N+P4S+P11F+T65A+G220N+Q327F+E501V+ Y504T;
P2N+P4S+P11F+T65A+Y245N+Q327F+E501V+ Y504T;
P2N+P4S+P11F+T65A+Q253N+Q327F+E501V+ Y504T;
P2N+P4S+P11F+T65A+D279N+Q327F+E501V+ Y504T;
P2N+P4S+P11F+T65A+Q327F+S359N+E501V+ Y504T;
P2N+P4S+P11F+T65A+Q327F+D370N+E501V+ Y504T;
P2N+P4S+P11F+T65A+Q327F+V460S+E501V+ Y504T;
P2N+P4S+P11F+T65A+Q327F+V460T+P468T+ E501V+Y504T;
P2N+P4S+P11F+T65A+Q327F+T463N+E501V+ Y504T;
P2N+P4S+P11F+T65A+Q327F+S465N+E501V+ Y504T; or
P2N+P4S+P11F+T65A+Q327F+T477N+E501V+ Y504T.

11. The variant of claim 1, which has reduced sensitivity to protease degradation.

12. A variant glucoamylase catalytic domain having at least 90% sequence identity to amino acids 30 to 494 of SEQ ID NO: 2 and comprising a substitution at a position corresponding to position 2 of the polypeptide of SEQ ID NO: 3, wherein the variant has glucoamylase activity.

13. A composition comprising the polypeptide of claim 1.

14. A composition according to claim 13, comprising an alpha-amylase.

15. A process of producing a fermentation product from starch-containing material comprising the steps of:
(a) liquefying starch-containing material in the presence of an alpha amylase;
(b) saccharifying the liquefied material; and
(c) fermenting with a fermenting organism;
wherein step (a) and/or step (b) is carried out using at least a glucoamylase of claim 1.

16. A process of producing a fermentation product from starch-containing material, comprising the steps of:

(a) saccharifying starch-containing material at a temperature below the initial gelatinization temperature of said starch-containing material; and
(b) fermenting with a fermenting organism, wherein step (a) is carried out using at least a glucoamylase of claim 1.

* * * * *